(12) United States Patent
Gould-Rothberg

(10) Patent No.: US 6,750,012 B1
(45) Date of Patent: Jun. 15, 2004

(54) METHOD OF IDENTIFYING A PSYCHOTROPIC AGENT USING DIFFERENTIAL GENE EXPRESSION

(75) Inventor: Bonnie Gould-Rothberg, Guilford, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/468,253

(22) Filed: Dec. 20, 1999

Related U.S. Application Data
(60) Provisional application No. 60/113,127, filed on Dec. 21, 1998.

(51) Int. Cl.$^7$ .......................... C12Q 1/68; G01N 33/48; C12N 1/38
(52) U.S. Cl. .......................... 435/6; 435/40.52; 435/244
(58) Field of Search .......................... 435/6, 40.52, 244

(56) References Cited

FOREIGN PATENT DOCUMENTS

| WO | WO 95 13369 | 5/1995 |
|----|-------------|--------|
| WO | WO 98 45436 | 10/1998 |

OTHER PUBLICATIONS

Shimkets, R. A. et al., "Gene expression analysis by transcript profiling coupled to a gene database query" *Nature Biotechnology* 17:798–803 Aug. 1999.

Mashreghi, Mohammadi M., "Human DNA Sequence from Clone 51J12 on Chromosome 6q26–27" Database EMBL 'Online! embl AC#AL031781 Sep. 29, 1998.

Altschul, S. F., et al. (1997). "Gapped BLAST and PSI–BLAST: a new generation of protein database search programs." *Nucleic Acids Research* 25 (17): 3389–3402.

Cardoso, F. and Jankovic, J. (1997). "Dystonia and Dyskinesia." *The Psychiatric Clinics of North America* 20 (4): 821–838.

Casey, D. E. (1998). "Effects of Clozapine Therapy in Schizophrenic Individuals at Risk for Tardive Dyskinesia." *J Clin Psychiatry* 59 (Suppl. 3): 31–37.

Chen, T., et al. (1997). "Self–Association of the Single–KH–Domain Family Members Sam68, GRP33, GLD–1, and Qk1: Role of the KH Domain." *Molecular and Cellular Biology* 17 (10): 5707–5718.

de la Fuente–Fernandez, R. (1998). "Tardive Dyskinesia in Dopa–Responsive Dystonia: A Rappraisal of the Dopamine Hypothesis of Tardive Dyskinesia [see comments]." *Neurology* 50 (4): 1134–1135.

Delfs, J. M., et al. (1995). "Expression of Glutamic Acid Decarboxylase mRNA in Striatum and Pallidum in an Animal Model of Tardive Dyskinesia." *Experimental Neurology* 133 (2): 175–188.

Ebersole, T. A., et al. (1996). "The Quaking Gene Product Necessary in Embryogenesis and Myelination Combines Features of RNA Binding and Signal Transduction Proteins [see comments]." *Nature Genetics* 12 (3): 260–265.

Egan, M., et al. (1997). "Treatment of Tardive Dyskinesia." *Schizophrenia Bulletin* 23 (4): 538–609.

Fujigasaki, H., et al. (1996). "Murine Central Neurons Express a Novel Member of the cdc10/SWI6 Motif–Containing Protein Superfamily." *Molecular Brain Research* 40 (2): 203–213.

Fyrberg, C., et al. (1997). "A Drosophila Muscle–Specific Gene Related to the Mouse Quaking Locus." *Gene* 197 (1–2): 315–323.

Gill, H. S., et al. (1997). "Extrapyramidal Symptoms Associated with Cyclic Antidepressant Treatment: A Review of the Literature and Consolidating Hypotheses." *Journal of Clinical Psychopharmacology* 17 (5): 377–389.

Hardy, R. J., et al. (1996). "Neural Cell Type–Specific Expression of QKI Proteins is Altered in Quaking Viable Mutant Mice." *The Journal of Neuroscience* 16 (24): 7941–7949.

Hashimoto, T., et al. (1998). Mixture in the Distribution of Haloperidol–Induced Oral Dyskinesias in the Rat Supports an Animal Model of Tardive Dyskinesia. *Psychopharmacology (Berl)* 137 (2): 107–112.

Kelly, M. A., et al. (1998). "Locomotor Activity in D2 Dopamine Receptor–Deficient Mice is Determined by Gene Dosage, Genetic Background, and Developmental Adaptations." *The Journal of Neuroscience* 18 (9): 3470–3479.

Lauterbach, E. C., et al. (1997). "Clinical Manifestations of Dystonia and Dyskinesia After SSRI Administration [letter; comment]." *J Clin Psychiatry* 58 (9): 403–404.

Lo, P. C. and Frasch, M. (1997). "A Novel KH–Domain Protein Mediates Cell Adhesion Processes in Drosophila." *Developmental Biology* 190 (2): 241–256.

Nakki, R., et al. (1996). "Haloperidol Prevents Ketamine– and Phencyclidine–Induced HSP70 Protein Expression but not Microglial Activation." *Experimental Neurology* 137 (2): 234–241.

Parsons, B., et al. (1995). "Neuroleptics Up–Regulate Adenosine A2a Receptors in Rat Striatum: Implications for the Mechanism and the Treatment of Tardive Dyskinesia." *Journal of Neurochemistry* 65 (5): 2057–2064.

Ritter, L. M. and Meador–Woodruff, J. H. (1997). "Antipsychotic Regulation of Hippocampal Dopamine Receptor Messenger RNA Expression." *Society of Biological Psychiatry* 42 (3): 155–164.

(List continued on next page.)

*Primary Examiner*—Gary Kunz
*Assistant Examiner*—Stephen Gucker
(74) *Attorney, Agent, or Firm*—Mintz Levin Cohn Ferris Glovsky & Popeo, P.C.; Ivor R. Elrifi, Esq.; Cynthia A. Kozakiewicz, Esq.

(57) ABSTRACT

Disclosed are methods of identifying psychotropic agents that do not induce motor side effects using differential gene expression. Also disclosed are novel nucleic acid sequences whose expression is differentially regulated by psychotropic agents.

20 Claims, 14 Drawing Sheets

OTHER PUBLICATIONS

Seth, P. et al. (1998) "Cloning and Functional Characterization of a σ Receptor from Rat Brain." 70: 922–931.

Tanaka, H., et al. (1997). "Cloning and Expression of the Quaking Gene in the Zebrafish Embryo." *Mechanisms of Development* 69 (1–2): 209–13.

Taoka, M., et al. (1992). "A Rate Cerebellar Protein Containing the cdc10/SW16 Motif." *Eur J Biochem* 207 (2): 615–620.

Taoka, M., et al. (1994). "Murine Cerebellar Neurons Express a Novel Gene Encoding a Protein Related to Cell Cycle Control and Cell Fate Determination Proteins." *The Journal of Biological Chemistry* 269 (13): 9946–9951.

Vernet, C. and Artzt, K. (1997). "STAR, a Gene Family Involved in Signal Transduction and Activation of RNA." *Trends Genet* 13 (12): 479–484.

Walters, V. L., et al. (1997). "New Strategies for Old Problems: Tardive Dyskinesia (TD). Review and Report on Severe TD Cases Treated with Clozapine, with 12, 8 and 5 Years of Video Follow–Up." *Schizophrenia Research* 28 (2–3): 231–246.

Zorn, A. M. and Krieg, P. A. (1997). "The KH Domain Protein Encoded by Quaking Functions as a Dimer and is Essential for Notochord Development in Xenopus Embryos." *Genes & Development* 11 (17): 2176–2190.

Human Qk5 (Quaking splice variant 5)

```
   1 GGCGGAGTGAGCTGCGGAGCCTGGAATATGGTCGGGGAAATGGAAACGAAGGAGAAGCCGAAGCCCACCCCAGATTACCT
                                      M  V  G  E  M  E  T  K  E  K  P  K  P  T  P  D  Y  L
  81 GATGCAGCTGATGAACGACAAGAAGCTCATGAGCAGCCTGCCCAACTTCTGCGGGATCTTCAACCACCTCGAGCGGCTGC
      M  Q  L  M  N  D  K  K  L  M  S  S  L  P  N  F  C  G  I  F  N  H  L  E  R  L  L
 161 TGGACGAAGAAATTAGCAGAGTACGGAAAGACATGTACAATGACACATTAAATGGCAGTACAGAGAAAAGGAGTGCAGAA
      D  E  E  I  S  R  V  R  K  D  M  Y  N  D  T  L  N  G  S  T  E  K  R  S  A  E
 241 TTGCCTGATGCTGTGGGACCTATTGTTAAGTTACAAGAGAAACTTTATGTGCCTGTAAAAGAATACCCAGATTTTAATTT
      L  P  D  A  V  G  P  I  V  K  L  Q  E  K  L  Y  V  P  V  K  E  Y  P  D  F  N  F
 321 TGTTGGGAGAATCCTTGGACCTAGAGGACTTACAGCCAAACAACTTGAAGCAGAAACCGGATGTAAAATCATGGTCCGAG
      V  G  R  I  L  G  P  R  G  L  T  A  K  Q  L  E  A  E  T  G  C  K  I  M  V  R  G
 401 GCAAAGGCTCAATGAGGGATAAAAAAAAGGAGGAGCAAAATAGAGGCAAGCCCAATTGGGAGCATCTAAATGAAGATTTA
      K  G  S  M  R  D  K  K  K  E  E  Q  N  R  G  K  P  N  W  E  H  L  N  E  D  L
 481 CATGTACTAATCACTGTGGAAGATGCTCAGAACAGAGCAGAAATCAAATTGAAGAGAGCAGTTGAAGAAGTGAAGAAATT
      H  V  L  I  T  V  E  D  A  Q  N  R  A  E  I  K  L  K  R  A  V  E  E  V  K  K  L
 561 ATTGGTACCTGCAGCAGAAGGAGAAGACAGCCTGAAGAAGATGCAGCTGATGGAGCTTGCGATTCTGAATGGCACCTACA
      L  V  P  A  A  E  G  E  D  S  L  K  K  M  Q  L  M  E  L  A  I  L  N  G  T  Y  R
 641 GAGATGCCAACATTAAATCACCAGCCCTTGCCTTTTCTCTTGCAGCAACAGCCCAGGCTGCTCCAAGGATCATTACTGGG
      D  A  N  I  K  S  P  A  L  A  F  S  L  A  A  T  A  Q  A  A  P  R  I  I  T  G
 721 CCTGCGCCGGTTCTCCCACCAGCTGCCCTGCGTACTCCTACGCCAGCTGGCCCTACCATAATGCCTTTGATCAGACAAAT
      P  A  P  V  L  P  P  A  A  L  R  T  P  T  P  A  G  P  T  I  M  P  L  I  R  Q  I
 801 ACAGACCGCTGTCATGCCAAACGGAACTCCTCACCCAACTGCTGCAATAGTTCCTCCAGGGCCCGAAGCTGGTTTAATCT
      Q  T  A  V  M  P  N  G  T  P  H  P  T  A  A  I  V  P  P  G  P  E  A  G  L  I  Y
 881 ATACACCCTATGAGTACCCCTACACATTGGCACCAGCTACATCAATCCTTGAGTATCCTATTGAACCTAGTGGTGTATTA
      T  P  Y  E  Y  P  Y  T  L  A  P  A  T  S  I  L  E  Y  P  I  E  P  S  G  V  L
 961 GGTGCGGTGGCTACTAAAGTTCGAAGGCACGATATGCGTGTCCATCCTTACCAAAGGATTGTGACCGCAGACCGAGCCGC
      G  A  V  A  T  K  V  R  R  H  D  M  R  V  H  P  Y  Q  R  I  V  T  A  D  R  A  A
1041 CACCGGCAACTAACCTATGACCTTCTGACCTCTGAACTCTTCACCCAATGATGACCTGACCATGCCTGCCTGCTGATCAG
      T  G  N  (SEQ ID NO:14)
1121 TTAACTGGTAATCGCCTTTGCTTGCCTGTCGTCAGTGCAGCGAGCTGAGGCACTTGTCCGTTCGTCTTACCATCTAACCA
1201 AACAAAAGACAAAGAAATTGTTGTCCTCCAACTCAGCTTTTTTTTTTTTTTTCCTGTTTGGGTGAAAGTGGTTCTAGAAA
1281 CTGCACTGAATAGTAGTAAAGCAATAAGGCCCAATTCATCCCACAGCACTGATCATCTTTTAATATCCCACCCTAAGCGA
1361 ACGGTAAGAAGGCCTCTCTTAAGAAGGGGAGACAGATGGTCCTTAACTACTCAATGACAGAGGCAGTTACTGTGAGAGAC
1441 TTCTAGGAATCTTTTTCTTCTCATAGCGAAGTCAAAGCTCTCTCTGAATGTACTGTGTGATGATGCATCATGCATGAACC
1521 TTCGGTCAGGGATATCATTGGTGAAGTGATTTCAAAAAGTATTCAAAATTTGATATGCTGTTTAGTCACTACAGTGCCCT
1601 CAAAGGGCAGAAGTTGCAGCCTTTTTTATATTGCCTGCCAAAATTTGAAGTATTAGAAGAAAGTGTGCCATGAGAGAAAA
1681 ACTTAAGGAGTTTTGAAAAGTAATGCAAATAACAAAACTGCAACACTATTTTTAAAAAGATAAATATCTGAGTTAAAATT
1761 ACTGAATCTTTATTTTACACCTAAAAAAAATATGAGAACAAGGTACATGCATTATGTGTCACATTACTGGGCAAACTGTTC
1841 AAGTATTTTTTTTTAAACCTCCCTGTATAGAAAAAAATCATTAAGGATGTAAAAGCCATGCTTGCCTATTTGCTGTATAC
1921 ATGTAATGAAATTGTAGATAAAGTGTAGTGCATTGAAACAAATGAACCAAAAGTAGATACTTTTACTATACAAGGGTGCT
2001 GGTGCAGAAAAAATATATATATTTTGGGAAATGTAGCATTTTATACTTTCAAGTGTTATAGAAAAAAAAAAAAAAAAAAA
2081 AAAAAAAAAAAA (SEQ ID NO:13)
```

Fig. 1

Human Qk7 (Quaking splice variant 7)

```
   1 GGAATATGGTCGGGGAAATGGAAACGAAGGAGAAGCCGAAGCCCACCCCAGATTACCTGATGCAGCTGATGAACGACAAG
               M  V  G  E  M  E  T  K  E  K  P  K  P  T  P  D  Y  L  M  Q  L  M  N  D  K
  81 AAGCTCATGAGCAGCCTGCCCAACTTCTGCGGGATCTTCAACCACCTCGAGCGGCTGCTGGACGAAGAAATTAGCAGAGT
       K  L  M  S  S  L  P  N  F  C  G  I  F  N  H  L  E  R  L  L  D  E  E  I  S  R  V
 161 ACGGAAAGACATGTACAATGACACATTAAATGGCAGTACAGAGAAAAGGAGTGCAGAATTGCCTGATGCTGTGGGACCTA
       R  K  D  M  Y  N  D  T  L  N  G  S  T  E  K  R  S  A  E  L  P  D  A  V  G  P  I
 241 TTGTTCAGTTACAAGAGAAACTTTATGTGCCTGTAAAAGAATACCCAGATTTTAATTTTGTTGGGAGAATCCTTGGACCT
       V  Q  L  Q  E  K  L  Y  V  P  V  K  E  Y  P  D  F  N  F  V  G  R  I  L  G  P
 321 AGAGGACTTACAGCCAAACAACTTGAAGCAGAAACCGGATGTAAAATCATGGTCCGAGGCAAAGGCTCAATGAGGGATAA
       R  G  L  T  A  K  Q  L  E  A  E  T  G  C  K  I  M  V  R  G  K  G  S  M  R  D  K
 401 AAAAAAGGAGGAGCAAAATAGAGGCAAGCCCAATTGGGAGCATCTAAATGAAGATTTACATGTACTAATCACTGTGGAAG
       K  K  E  Q  N  R  G  K  P  N  W  E  H  L  N  E  D  L  H  V  L  I  T  V  E  D
 481 ATGCTCAGAACAGAGCAGAAATCAAATTGAAGAGAGCAGTTGAAGAAGTGAAGAAATTATTGGTACCTGCAGCAGAAGGA
       A  Q  N  R  A  E  I  K  L  K  R  A  V  E  E  V  K  K  L  L  V  P  A  A  E  G
 561 GAAGACAGCCTGAAGAAGATGCAGCTGATGGAGCTTGCGATTCTGAATGGCACCTACAGAGATGCCAACATTAAATCACC
       E  D  S  L  K  K  M  Q  L  M  E  L  A  I  L  N  G  T  Y  R  D  A  N  I  K  S  P
 641 AGCCCTTGCCTTTTCTCTTGCAGCAACAGCCCCAGGCTGCTCCAAGGATCATTACTGGGCCTGCGCCGGTTCTCCCACCAG
       A  L  A  F  S  L  A  A  T  A  Q  A  A  P  R  I  I  T  G  P  A  P  V  L  P  P  A
 721 CTGCCCTGCGTACTCCTACGCCAGCTGGCCCTACCATAATGCCTTTGATCAGACAAATACAGACCGCTGTCATGCCAAAC
       A  L  R  T  P  T  P  A  G  P  T  I  M  P  L  I  R  Q  I  Q  T  A  V  M  P  N
 801 GGAACTCCTCACCCAACTGCTGCAATAGTTCCTCCAGGGCCCGAAGCTGGTTTAATCTATACACCCTATGAGTACCCCTA
       G  T  P  H  P  T  A  A  I  V  P  P  G  P  E  A  G  L  I  Y  T  P  Y  E  Y  P  Y
 881 CACATTGGCACCAGCTACATCAATCCTTGAGTATCCTATTGAACCTAGTGGTGTATTAGAGTGGATTGAAATGCCAGTCA
       T  L  A  P  A  T  S  I  L  E  Y  P  I  E  P  S  G  V  L  E  W  I  E  M  P  V  M
 961 TGCCTGATATTTCAGCCCATTGACTTGCTGGATGAAGGACTAGAATACAGCAGCTGTTATAACACGACCAGTCAATGTGG
       P  D  I  S  A  H  (SEQ ID NO:16)
1041 AACAAACTGTTTCTGTGCAACCCCTTTGTTTTACCAGACAAAATTTGAATACTTTTTTTCCTGAATTGTATATGACCTTG
1121 GTGCTGCATGCATGCTGTTGACTTTTAGGACTTTGATCTTTTAAGGTTTTTTTCCCCAGCATTAATATTGATTTATAAAG
1201 ATTTGAAAATCTTTTAATGAACTGGAGAACACTAAGATTTAAACTCGAAAATTCGTTGTTCAAGTAAAGAAAGCCATGAT
1281 GCTCTGTATGTTATCTGTGTGTGTGCATGCACTCAGGTGCCCTTTGTTTCATGAACAAATACATTTCATTGTACATGTTT
1361 TCTGTTTAAATCATTGTATAAAGTAATTGCAGGTCAGAATTATACCACAGAACTGTTTATGAGAGGCTTGTGTCTGTTGC
1441 ACATTTCTTGAAGCATTTTTAAAATAACATGTAACCTGTAACCTTGTTGTTTAAGTTTTCTTTTCTATTAATACTCTGTC
1521 CTGTGGTCCCGTGCATGCTCCTTTTCCCAGAACTCCTCTCTGCTGCACCCACAGCATCTGTTCCCGAGGAGTTATGACTC
1601 TTGACTTCCTGCAGGGCTGGGGCTCTTAGCCACCAGCTGCTGTTCCAGCACTTTCAGCGCAAGATCTCCCTGATTTTGCC
1681 ACGTGGAATTGTACTTGTATATGATTACCTTATCTAAAATGAATAAGAGGTGATGGACCAGTTTACTGCTTAGAAATAGC
1761 AAGAGGCACTGCAGTAAAACTTGTTTCTCATTGTAAAGCTTCATGTCTTTTGTTTGTTGGAAAATTTTTACTTATAGAAA
1841 CTTAATTATTAGACTGGTAAAATAAAGACCAAAATATGCAGATTTCTAATTGGCATTCATAAGGTGAATAATAATAAGTG
1921 CCCAATGAAAAAATCTATTATGGTTAATTTCATTTCTTGCTTTGCCACCTAAGCAGTAAAACATGATATTGACCACTTGG
2001 AGAACTCAGAAAATTATTTTAAATTTCTAAGTTATAATAAATTTGCACACAGATAACATGCATGCTATTTATGTCACATC
2081 TCACATTAAATTATTTTAAAATAAGCAGTGCCCTTCAAAACAGATGCAGACATGTGTGTTGGTAGTAGTGAGGAGATTGG
2161 TATTAGCATCAAGTCTTCATTGATGACTAATTTTTAATTCCCTTCCTTTTATCTTTAGGTATGGCTTTCCCAACGAAAGG
2241 CTAAGAATTCAAGAACGGTCTTAACTGAACCCTCATCAGATCTGAATTTAACAAATGCTTAGTCTCAGCAGCCTCCGGGG
2321 GAAAAAGCTTAGCCTAGCAGTCAGTGACTTACTTGCACTTTTTGCACATAGATATAAAGTAAAATTATGTTATTAATTT
2401 GGTTTAGTCTGTAATATTACACAGTAATGGTAATTTATAAAGGAGTGTATAGTAGTATACTGACTGCTAAGTG
    (SEQ ID NO:15)
```

Fig. 2

Blast-N Homology:
>gb:GENBANK-ID:MMU44940 | acc:U44940 Mus musculus quaking type I (QKI) mRNA, complete cds - Mus musculus, 6747 bp (RNA)
Plus Strand HSPs:

Score = 4469 (670.5 bits), Expect = 6.7e-217, Sum P(3) = 6.7e-217
Identities = 947/1005 (94%), Positives = 947/1005 (94%), Strand = Plus / Plus

```
Query:    1 GGCGGAGTGAGCTGCGGAGCCTGGAATATGGTCGGGGAAATGGAAACGAAGGAGAAGCCG 60
            GGCGGAGTGAGCTGCGGAGCCTGGAATATGGTCGGGGAAATGGAAACGAAGGAGAAGCCG
Sbjct:  481 GGCGGAGTGAGCTGCGGAGCCTGGAATATGGTCGGGGAAATGGAAACGAAGGAGAAGCCG 540

Query:   61 AAGCCCACCCCAGATTACCTGATGCAGCTGATGAACGACAAGAAGCTCATGAGCAGCCTG 120
            AAGCCCACCCCAGATTA  TGATGCAGCTGATGAACGACAAGAAGCTCATGAGCAGCCTG
Sbjct:  541 AAGCCCACCCCAGATTATTTGATGCAGCTGATGAACGACAAGAAGCTCATGAGCAGCCTG 600

Query:  121 CCCAACTTCTGCGGGATCTTCAACCACCTCGAGCGGCTGCTGGACGAAGAAATTAGCAGA 180
            CCCAACTTCTGCGGGATCTTCAACCACCTCGAGCGGCTGCTGGACGAAGAAATTAGCAGA
Sbjct:  601 CCCAACTTCTGCGGGATCTTCAACCACCTCGAGCGGCTGCTGGACGAAGAAATTAGCAGA 660

Query:  181 GTACGGAAAGACATGTACAATGACACATTAAATGGCAGTACAGAGAAAAGGAGTGCAGAA 240
            GTACGGAAAGACATGTACAATGACAC TTAAATGGCAGTACAGAGAAAAG AGTGCAGAA
Sbjct:  661 GTACGGAAAGACATGTACAATGACACGTTAAATGGCAGTACAGAGAAAAGAAGTGCAGAA 720

Query:  241 TTGCCTGATGCTGTGGGACCTATTGTTAAGTTACAAGAGAAACTTTATGTGCCTGTAAAA 300
            TTGCCTGA GC GTGGGACC ATTGTT AGTTACAAGAGAAACTTTATGTGCCTGTAAAA
Sbjct:  721 TTGCCTGACGCGGTGGGACCCATTGTTCAGTTACAAGAGAAACTTTATGTGCCTGTAAAA 780

Query:  301 GAATACCCAGATTTTAATTTTGTTGGGAGAATCCTTGGACCTAGAGGACTTACAGCCAAA 360
            GAATACCC GATTTTAATTTTGTTGGGAGAATCCTTGGACCTAGAGGACTTACAGC AAA
Sbjct:  781 GAATACCCTGATTTTAATTTTGTTGGGAGAATCCTTGGACCTAGAGGACTTACAGCTAAA 840

Query:  361 CAACTTGAAGCAGAAACCGGATGTAAAATCATGGTCCGAGGCAAAGGCTCAATGAGGGAT 420
            CAACTTGAAGCAGAAAC GGATGTAAAAT ATGGTCCGAGGCAAAGGCTCAATGAGGGAT
Sbjct:  841 CAACTTGAAGCAGAAACGGGATGTAAAATAATGGTCCGAGGCAAAGGCTCAATGAGGGAT 900

Query:  421 AAAAAAAAGGAGGAGCAAAATAGAGGCAAGCCCAATTGGGAGCATCTAAATGAAGATTTA 480
            AAAAA AAGGAGGAGCAAAATAGAGGCAAGCCCAATTGGGAGCATCTAAATGAAGA TTA
Sbjct:  901 AAAAAGAAGGAGGAGCAAAATAGAGGCAAGCCCAATTGGGAGCATCTAAATGAAGACTTA 960

Query:  481 CATGTACTAATCACTGTGGAAGATGCTCAGAACAGAGCAGAAATCAAATTGAAGAGAGCA 540
            CATGTACTAATCACTGTGGAAGATGCTCAGAACAGAGCAGAAATCAA TGAAGAGAGC
Sbjct:  961 CATGTACTAATCACTGTGGAAGATGCTCAGAACAGAGCAGAAATCAAGCTGAAGAGAGCG 1020

Query:  541 GTTGAAGAAGTGAAGAAATTATTGGTACCTGCAGCAGAAGGAGAAGACAGCCTGAAGAAG 600
            GTTGAAGAAGTGAAGAA TTA TGGTACCTGC GC GAAGG GAAGACAGCCTGAAGAAG
Sbjct: 1021 GTTGAAGAAGTGAAGAAGTTACTGGTACCTGCGGCTGAAGGTGAAGACAGCCTGAAGAAG 1080
```

Fig. 3A-1

```
Query:    601 ATGCAGCTGATGGAGCTTGCGATTCTGAATGGCACCTACAGAGATGCCAACATTAAATCA 660
              ATGCAGCTGATGGAGCTTGC ATTCTGAATGGCACCTACAGAGA GCCAACATTAAATCA
Sbjct:   1081 ATGCAGCTGATGGAGCTTGCAATTCTGAATGGCACCTACAGAGACGCCAACATTAAATCA 1140

Query:    661 CCAGCCCTTGCCTTTTCTCTTGCAGCAACAGCCCAGGCTGCTCCAAGGATCATTACTGGG 720
              CCAGCCCTTGCCTTTTCTCTTGCAGCAAC GCCCAGGCTGCTCCAAGGATCAT ACTGGG
Sbjct:   1141 CCAGCCCTTGCCTTTTCTCTTGCAGCAACTGCCCAGGCTGCTCCAAGGATCATCACTGGG 1200

Query:    721 CCTGCGCCGGTTCTCCCACCAGCTGCCCTGCGTACTCCTACGCCAGCTGGCCCTACCATA 780
              CCTGCGCC GT CTCCCACCAGCTGC CTGCGTAC CCTACGCCAGCTGGCCCTACCATA
Sbjct:   1201 CCTGCGCCTGTCCTCCCACCAGCTGCTCTGCGTACACCTACGCCAGCTGGCCCTACCATA 1260

Query:    781 ATGCCTTTGATCAGACAAATACAGACCGCTGTCATGCCAAACGGAACTCCTCACCCAACT 840
              ATGCCTTTGATCAGACAAATACAGACCGCTGTCATGCCAAACGGAACTCCTCACCCAACT
Sbjct:   1261 ATGCCTTTGATCAGACAAATACAGACCGCTGTCATGCCAAACGGAACTCCTCACCCAACT 1320

Query:    841 GCTGCAATAGTTCCTCCAGGGCCCGAAGCTGGTTTAATCTATACACCCTATGAGTACCCC 900
              GCTGCAATAGT CCTCCAGGGCC GAAGCTGG TTAATCTA ACACCCTATGA TACCCC
Sbjct:   1321 GCTGCAATAGTCCCTCCAGGGCCTGAAGCTGGGTTAATCTACACACCCTATGAATACCCC 1380

Query:    901 TACACATTGGCACCAGCTACATCAATCCTTGAGTATCCTATTGAACCTAGTGGTGTATTA 960
              TACACATTGGCACCAGCTACATCAATCCTTGAGTA CCTATTGAACC AGTGGTGT TTA
Sbjct:   1381 TACACATTGGCACCAGCTACATCAATCCTTGAGTACCCTATTGAACCCAGTGGTGTGTTA 1440

Query:    961 G-GTGCGGTGGCTACTAAAGTTCGAAGGCACGATATGCGTGTCCAT 1005  (SEQ ID NO:51)
                G GTG G T G A    AGT C A G C  GATAT    G CCAT         (SEQ ID NO:52)
Sbjct:   1441 GAGTG-GATTGAAATGCCAGT-C-ATGCCT-GATATTTCAGCCCAT 1482  (SEQ ID NO:53)
```

Fig. 3A-2

Score = 391 (58.7 bits), Expect = 6.7e-217, Sum P(3) = 6.7e-217
Identities = 79/80 (98%), Positives = 79/80 (98%), Strand = Plus / Plus Query:    957 ATTAGGTGCGGTGGCTACTAAAGTTCGAAGGCACGATATGCGTGTCCATCCTTACCAAAG 1016
              |||||||||||||||||||||||||||||||||||||||||||||||||||||||||||
Sbjct:   3477 ACTAGGTGCGGTGGCTACTAAAGTTCGAAGGCACGATATGCGTGTCCATCCTTACCAAAG 3536

Query:   1017 GATTGTGACCGCAGACCGAG 1036   (SEQ ID NO:54)
              ||||||||||||||||||||
Sbjct:   3537 GATTGTGACCGCAGACCGAG 3556   (SEQ ID NO:55)

Fig. 3B

Score = 146 (21.9 bits), Expect = 6.7e-217, Sum P(3) = 6.7e-217
Identities = 56/81 (69%), Positives = 56/81 (69%), Strand = Plus / Plus Query:   2008 AAAAAATATATATATT-TTGGGAAAT-GTAGCATTTTATA--CTTTCAAGTGTTATAGAA 2063
                   AA AAAT T  AT TT TT G AAAT G A  ATT  A A  C  T AA    TTAT GAA
Sbjct:   6667 AAGAAAT-TCCATGTTGTTTGTAAATAGAATAATTGAAAAAGCAATAAACATTTATTGAA 6725

Query:   2064 AAAAAAAAAAAAAAAAAAAAA 2085    (SEQ ID NO:56)
                   AAAA AAAAAAAAAAAAAAA       (SEQ ID NO:57)
Sbjct:   6726 CAAAAGAAAAAAAAAAAAAAA 6747    (SEQ ID NO:58)

Fig. 3C

Blast-X Homology:
>ptnr:TREMBLNEW-ACC:G4099410 RNA BINDING/SIGNAL TRANSDUCTION
PROTEIN QKI-1 - GALLUS GALLUS (CHICKEN), 340 aa.

Plus Strand HSPs:

```
Score = 1735 (610.8 bits), Expect = 5.6e-178, P = 5.6e-178
Identities = 336/341 (98%), Positives = 339/341 (99%), Frame = +1

Query:     28 MVGEMETKEKPKPTPDYLMQLMNDKKLMSSLPNFCGIFNHLERLLDEEISRVRKDMYNDT 207
              MVGEME KEKPKP+PDYLMQLMNDKKLMSSLPNFCGIFNHLERLLDEEISRVRKDMYNDT
Sbjct:      1 MVGEMEAKEKPKPSPDYLMQLMNDKKLMSSLPNFCGIFNHLERLLDEEISRVRKDMYNDT 60

Query:    208 LNGSTEKRSAELPDAVGPIVKLQEKLYVPVKEYPDFNFVGRILGPRGLTAKQLEAETGCK 387
              LNGSTEKRSAELPDAVGPIV+LQEKLYVPVKEYPDFNFVGRILGPRGLTAKQLEAETGCK
Sbjct:     61 LNGSTEKRSAELPDAVGPIVQLQEKLYVPVKEYPDFNFVGRILGPRGLTAKQLEAETGCK 120

Query:    388 IMVRGKGSMRDKKKEEQNRGKPNWEHLNEDLHVLITVEDAQNRAEIKLKRAVEEVKKLLV 567
              IMVRGKGSMRDKKKEEQNRGKPNWEHLNEDLHVLITVEDAQNRAEIKLKRAVEEVKKLL+
Sbjct:    121 IMVRGKGSMRDKKKEEQNRGKPNWEHLNEDLHVLITVEDAQNRAEIKLKRAVEEVKKLLI 180

Query:    568 PAAEGEDSLKKMQLMELAILNGTYRDANIKSPALAFSLAATAQAAPRIITGPAPVLPPAA 747
              PAAEGEDSLKKMQLMELAILNGTYRDANIKSPALAFSLAATAQA PRIITGPAPVLPPAA
Sbjct:    181 PAAEGEDSLKKMQLMELAILNGTYRDANIKSPALAFSLAATAQA-PRIITGPAPVLPPAA 239

Query:    748 LRTPTPAGPTIMPLIRQIQTAVMPNGTPHPTAAIVPPGPEAGLIYTPYEYPYTLAPATSI 927
              LRTPTPAGPTIMPLIRQIQTAVMPNGTPHPTAAIVPPGPEAGLIYTPYEYPYTLAPATSI
Sbjct:    240 LRTPTPAGPTIMPLIRQIQTAVMPNGTPHPTAAIVPPGPEAGLIYTPYEYPYTLAPATSI 299

Query:    928 LEYPIEPSGVLGAVATKVRRHDMRVHPYQRIVTADRAATGN 1050  (SEQ ID NO:14)
              LEYPIEPSGVLGAVATKVRRHDMRVHPYQRIVTADRAATGN        (SEQ ID NO:59)
Sbjct:    300 LEYPIEPSGVLGAVATKVRRHDMRVHPYQRIVTADRAATGN 340   (SEQ ID NO:60)
```

Fig. 3D

Blast-N Homology:
>gb:GENBANK-ID:MMU44940 | acc:U44940 Mus musculus quaking type I (QKI) mRNA, complete cds - Mus musculus, 6747 bp (RNA).

Plus Strand HSPs:

```
Score = 4893 (734.1 bits), Expect = 0.0, Sum P(3) = 0.0
Identities = 1009/1047 (96%), Positives = 1009/1047 (96%), Strand = Plus / Plus Query:    1 GGAATATGGTCGGGGAAATGGAAACGAAGGAGAAGCCGAAGCCCACCCCAGATTACCTGA 60
            |||||||||||||||||||||||||||||||||||||||||||||||||||||||| |||
Sbjct:  503 GGAATATGGTCGGGGAAATGGAAACGAAGGAGAAGCCGAAGCCCACCCCAGATTATTTGA 562

Query:   61 TGCAGCTGATGAACGACAAGAAGCTCATGAGCAGCCTGCCCAACTTCTGCGGGATCTTCA 120
            ||||||||||||||||||||||||||||||||||||||||||||||||||||||||||||
Sbjct:  563 TGCAGCTGATGAACGACAAGAAGCTCATGAGCAGCCTGCCCAACTTCTGCGGGATCTTCA 622

Query:  121 ACCACCTCGAGCGGCTGCTGGACGAAGAAATTAGCAGAGTACGGAAAGACATGTACAATG 180
            ||||||||||||||||||||||||||||||||||||||||||||||||||||||||||||
Sbjct:  623 ACCACCTCGAGCGGCTGCTGGACGAAGAAATTAGCAGAGTACGGAAAGACATGTACAATG 682

Query:  181 ACACATTAAATGGCAGTACAGAGAAAAGGAGTGCAGAATTGCCTGATGCTGTGGGACCTA 240
            |||| ||||||||||||||||||||||||| |||||||||||||||| || |||||||| |
Sbjct:  683 ACACGTTAAATGGCAGTACAGAGAAAAGAAGTGCAGAATTGCCTGACGCGGTGGGACCCA 742

Query:  241 TTGTTCAGTTACAAGAGAAACTTTATGTGCCTGTAAAAGAATACCCAGATTTTAATTTTG 300
            |||||||||||||||||||||||||||||||||||||||||||||||| |||||||||||
Sbjct:  743 TTGTTCAGTTACAAGAGAAACTTTATGTGCCTGTAAAAGAATACCCTGATTTTAATTTTG 802

Query:  301 TTGGGAGAATCCTTGGACCTAGAGGACTTACAGCCAAACAACTTGAAGCAGAAACCGGAT 360
            ||||||||||||||||||||||||||||||||| |||||||||||||||||||| ||||
Sbjct:  803 TTGGGAGAATCCTTGGACCTAGAGGACTTACAGCTAAACAACTTGAAGCAGAAACGGGAT 862

Query:  361 GTAAAATCATGGTCCGAGGCAAAGGCTCAATGAGGGATAAAAAAAGGAGGAGCAAAATA 420
            |||||| |||||||||||||||||||||||||||||||||||| |||||||||||||||
Sbjct:  863 GTAAAATAATGGTCCGAGGCAAAGGCTCAATGAGGGATAAAAAGAAGGAGGAGCAAAATA 922

Query:  421 GAGGCAAGCCCAATTGGGAGCATCTAAATGAAGATTTACATGTACTAATCACTGTGGAAG 480
            ||||||||||||||||||||||||||||||||||| ||||||||||||||||||||||||
Sbjct:  923 GAGGCAAGCCCAATTGGGAGCATCTAAATGAAGACTTACATGTACTAATCACTGTGGAAG 982

Query:  481 ATGCTCAGAACAGAGCAGAAATCAAATTGAAGAGAGCAGTTGAAGAAGTGAAGAAATTAT 540
            |||||||||||||||||||||||||| |||||||||||| |||||||||||||||| |||
Sbjct:  983 ATGCTCAGAACAGAGCAGAAATCAAGCTGAAGAGAGCGGTTGAAGAAGTGAAGAAGTTAC 1042
```

Fig. 4A-1

```
Query:   541 TGGTACCTGCAGCAGAAGGAGAAGACAGCCTGAAGAAGATGCAGCTGATGGAGCTTGCGA 600
             ||||||||| || |||||| ||||||||||||||||||||||||||||||||||||| |
Sbjct:  1043 TGGTACCTGCGGCTGAAGGTGAAGACAGCCTGAAGAAGATGCAGCTGATGGAGCTTGCAA 1102

Query:   601 TTCTGAATGGCACCTACAGAGATGCCAACATTAAATCACCAGCCCTTGCCTTTTCTCTTG 660
             |||||||||||||||||||||| ||||||||||||||||||||||||||||||||||||
Sbjct:  1103 TTCTGAATGGCACCTACAGAGACGCCAACATTAAATCACCAGCCCTTGCCTTTTCTCTTG 1162

Query:   661 CAGCAACAGCCCAGGCTGCTCCAAGGATCATTACTGGGCCTGCGCCGGTTCTCCCACCAG 720
             |||||| ||||||||||||||||||||||||| |||||||||||| || |||||||||
Sbjct:  1163 CAGCAACTGCCCAGGCTGCTCCAAGGATCATCACTGGGCCTGCGCCTGTCCTCCCACCAG 1222

Query:   721 CTGCCCTGCGTACTCCTACGCCAGCTGGCCCTACCATAATGCCTTTGATCAGACAAATAC 780
             |||| ||||||||| |||||||||||||||||||||||||||||||||||||||||||
Sbjct:  1223 CTGCTCTGCGTACACCTACGCCAGCTGGCCCTACCATAATGCCTTTGATCAGACAAATAC 1282

Query:   781 AGACCGCTGTCATGCCAAACGGAACTCCTCACCCAACTGCTGCAATAGTTCCTCCAGGGC 840
             |||||||||||||||||||||||||||||||||||||||||||||||| |||||||||
Sbjct:  1283 AGACCGCTGTCATGCCAAACGGAACTCCTCACCCAACTGCTGCAATAGTCCCTCCAGGGC 1342

Query:   841 CCGAAGCTGGTTTAATCTATACACCCTATGAGTACCCCTACACATTGGCACCAGCTACAT 900
             | |||||||| |||||||||||||||||||| ||||||||||||||||||||||||||
Sbjct:  1343 CTGAAGCTGGGTTAATCTACACACCCTATGAATACCCCTACACATTGGCACCAGCTACAT 1402

Query:   901 CAATCCTTGAGTATCCTATTGAACCTAGTGGTGTATTAGAGTGGATTGAAATGCCAGTCA 960
             |||||||||||||| |||||||||| |||||||| |||||||||||||||||||||||
Sbjct:  1403 CAATCCTTGAGTACCCTATTGAACCCAGTGGTGTGTTAGAGTGGATTGAAATGCCAGTCA 1462

Query:   961 TGCCTGATATTTCAGCCCATTGACTTGCTGGATGAAGGACTAGAATACAGCAGCTGTTAT 1020
             ||||||||||||||||||||||||||||||||||||||||||||||||||||||||||
Sbjct:  1463 TGCCTGATATTTCAGCCCATTGACTTGCTGGATGAAGGACTAGAATACAGCAGCTGTTAT 1522

Query:  1021 AACACGACCAGTCAATGTGGAACAAAC 1047   (SEQ ID NO:61)
             |||||||||||||||||||||  ||||
Sbjct:  1523 AACACGACCAGTCAATGTGGAAAAAAC 1549   (SEQ ID NO:62)
```

Fig. 4A-2

Score = 2281 (342.2 bits), Expect = 0.0, Sum P(3) = 0.0
Identities = 838/1156 (72%), Positives = 839/1156 (72%), Strand = Plus / Plus

```
Query:  1318 TGCCCTTTGTTTCAT--GAACAAATACATTTCATTGTACATGTTTTCTGTTTAAATCATT 1375
             TGC CTT G T C T  G   A A ACATTT ATTGTACATGTTTTCTGT T AA    T
Sbjct:  1827 TGCACTTAGGTGCCTTTGTTTATAAACATTTTATTGTACATGTTTTCTGTCTTAAGTCAT 1886

Query:  1376 GTATAAAGTAATTGCAGGTCAGA-ATTATACCACAGAACT-GT-TTATGAGAG-GCTTGT 1431
             T TA A  AAT         T AG A AT  ACA A  GT TTA  A AG G  TGT
Sbjct:  1887 -TGTATAA-AATAATTA-TAAGTCAGAATTATACAACAGAAGTGTTAGTA-AGAGGCTGT 1942

Query:  1432 GTCTGTTGCACAT-TTCTTGAAGCATTTTTAAAATAACATGTAACCTGTAACCTTGTTGT 1490
               T T    CA TT T A      TTTTAAAA AA A  TAAC TGTAACCT    T T
Sbjct:  1943 AT-TCTATTGCACATTACTTGAAGCATTTTAAAAAAAAAA-TAACATGTAACCTA--TAT 1998

Query:  1491 TTAAGTTTTCTTTTCTATTAATA-CTCTG--TCCTGTGGTCCCGTGCATGCTCCTTTTCC 1547
              TAA TT  TT     T TT T CT T     T CT TG TCC GTG   GC CC T C
Sbjct:  1999 ATAACCTTATTTAAGTTTTCCTTTCTATTAATTCTCTG-TCCTGTG---GCCCCGTGCA 2054

Query:  1548 CAGAACTCCTCTCTGCTGCACCCACAGCATCTGTTCCCGAGGAGTTATGACTCTTGACTT 1607
               G  CTCCT TC  C GAC  C  C TCTG C C   A  A G CTCTTG  TT
Sbjct:  2055 T-G--CTCCT-TCCCCAGAACTC-CT-C-TCTGC-CGCACTCACAGAAG-CTCTTG--TT 2103

Query:  1608 CCTGCAGG-GCTGGGGCTCTTAGCCACCAGCTGCTGTTCCAGCACTTTCAGCGCA-AGAT 1665
             CCTG AGG G T GGGCTCT AGC  CCAGCTGCTG TCC G ACT T AG GC  AG T
Sbjct:  2104 CCTG-AGGAGTTAGGGCTCTCAGCTTCCAGCTGCTGCTCCTG-ACTGTTAGTGCCTAGTT 2161

Query:  1666 CTCCCTGATTTTGCCACGTGGAATTGTACTTGTATATGATTACCT-TA--TCTAAAATGA 1722
              T CC AT    AC  G A T T CTT T TA AT A   TA  TT AA A
Sbjct:  2162 TTGCCAAATAGAATTACTATGCAGTCTGCTTATCTAAAATGAAAAATAGGTTTTCAACCA 2221

Query:  1723 ATA-AGAGGTGATGGAC--CA-GTTT-ACTGCT-TAGAAATAGCAAGAGGCACTGCAGTA 1776
                T   A G T A  GAC CA G    ACTGCT TA AAAT C  A  T AGTA
Sbjct:  2222 GTTTACTGCTTAGAGACAGCAAGAGGCACTGCTGTA-AAATTTCTCCATT-A-TAAAGTA 2278

Query:  1777 AAACTT-GTTTCTCATTGTAAAG-C-TTCATGTCTTTT--GT-TTGTTGGAAAATTTTTA 1830
             A A T GTTT    T GT AG C TT AT TT  T T   G  TTG T GAAA      A
Sbjct:  2279 ACATGTCGTTTGGTTTGGTTAGGACATTTATATATATAAAGAATTGATTGAAACCAAC-A 2337

Query:  1831 CTTATAGAAACTTAATTATT-AGACTGGTAAAATAAAGAC--CAAAATATGCAG-ATTT- 1885
             CT AT   AAC AAT AT AGA T    AAA TAA   C CAA T  CA A T
Sbjct:  2338 CT-ATT--AACAAAAT-ATGCAGA-TACCAAATTAACATCGTCAAGGTTCTCAATAAGTA 2392

Query:  1886 CTAA-TTGGCATTCATAAGGTGAATAATAATAAGTGCCCA-ATGAAAAA-ATCTATTATG 1942
             C AA TT G A T A      AT AT AT A T        AT A A  ATC AT AT
Sbjct:  2393 CCAAGTTAGAAATTATTATCATTATCATCATTATTATTATTATTATTATC-ATCATC 2451
```

Fig. 4B-1

```
Query:  1943 GTTAATTTCATTTCTTGCTTTGCCACCTAAGCAGTAAAACA-TGATATT-GACCACTTGG 2000
              T A   T ATTTCTTGCTTTGCCACCTAAGCAGTAAAACA TGATATT G CC  TTGG
Sbjct:  2452 ATCATCATTATTTCTTGCTTTGCCACCTAAGCAGTAAAACAATGATATTAGTCCT-TTGG 2510

Query:  2001 AGAACTCAGAAAATTATTTTAAATTTCTAAGTTATAATAAATTTGCACACAGATAACATG 2060
              AGAACT AG AAATTA TTTAAATT C AAGTTA A TAAATTTGCACACAGATAACATG
Sbjct:  2511 AGAACTGAGGAAATTACTTTAAATTCCCAAGTTACAGTAAATTTGCACACAGATAACATG 2570

Query:  2061 CATGCTATTTATGTCACATCTCACATTAAATTATTTTAAAATAAGCAGTGCCCTTCAAAA 2120
              CATG TAT TAT   CA T TCACATTA       TTTTAAAATAAGCAGTGCC TTCAAAA
Sbjct:  2571 CATGTTATGTAT--CAAGTTTCACATTA-----TTTTAAAATAAGCAGTGCCTTTCAAAA 2623

Query:  2121 CAGATGCAGACATGTGTGTTGGTAGTAGTGAGGAGATTGGTATTAGCATCAAGTCTTCAT 2180
              CAGATGCAGACAT TGTGTTGGT GTAGTGAGGAGATTGGTATTAGCATCAA TCTTCAT
Sbjct:  2624 CAGATGCAGACATATGTGTTGGTGGTAGTGAGGAGATTGGTATTAGCATCAAATCTTCAT 2683

Query:  2181 TGATGACTAATTTTTAATTCCCTTCCTTTTATCTTTAGGTATGGCTTTCCCAACGAAAGG 2240
              TGATGACTAAT TTTAATTCCCTTCCTTTTATCTTTAGGTATGGCTTTCCCAACGAAAGG
Sbjct:  2684 TGATGACTAATGTTTAATTCCCTTCCTTTTATCTTTAGGTATGGCTTTCCCAACGAAAGG 2743

Query:  2241 CTAAGAATTCAAGAACGGTCTTAACTGAACCCTCATCAGATCTGAATTTAACAAATGCTT 2300
              CTAAGAATTCAAGAACGGTCTTAAC GAACCCTCATCAGATCTGAATTTAACAAAT+CTT
Sbjct:  2744 CTAAGAATTCAAGAACGGTCTTAACCGAACCCTCATCAGATCTGAATTTAACAAATRCTT 2803

Query:  2301 AGTCTCAGCAGCCTCCGGGGGAAAAAAGCTTAGCCTAGCAGTCAGTGACTTACTTGCACT 2360
              AGTCTCAGCAG CTCCGGG  AAAAA  CTTAGCCTAGCAGTCAGTGACTTACTTGCACT
Sbjct:  2804 AGTCTCAGCAGNCTCCGGG--AAAAAC-CTTAGCCTAGCAGTCAGTGACTTACTTGCACT 2860

Query:  2361 TTTTGCACATAGATATAAAGTAAAATTATGTTATTAATTTGGTTTAGTCTGTAATATTAC 2420
              TTTTGCACATAGATATAAAGTAAAT AT   TATTAATTTGG TTAGTCTGTAATA T C
Sbjct:  2861 TTTTGCACATAGATATAAAGTAAATGATACTATTAATTTGGATTAGTCTGTAATACTGC 2920

Query:  2421 ACAGTAATGGTAATTTATAAAGGAGTGTATAGTAGTATACTGACTGCTAAGTG 2473 (SEQ ID NO:63)
                A AG AA   GTAATTTATAAAGGAGTG ATAG AGTA ACTGACTGCTAAGTG      (SEQ ID NO:64)
Sbjct:  2921 AAAGCAACAGTAATTTATAAAGGAGTGNATAGAAGTAAACTGACTGCTAAGTG 2973 (SEQ ID NO:65)
```

Fig. 4B-2

Score = 1551 (232.7 bits), Expect = 1.7e-283, Sum P(2) = 1.7e-283
Identities = 687/988 (69%), Positives = 687/988 (69%), Strand = Plus / Plus

```
Query:  1106 TTGTATATGACCTTGGTGCTGCATGCATGCTGTTGACTTTTAGGACTTTGATCTTTTAA- 1164
             TTGT TATGACCTTGGTGCTG  TGC TGCTGTTGACT  TAGGACTTTGATCTTTTAA
Sbjct:  1631 TTGTGTATGACCTTGGTGCTGTGTGCCTGCTGTTGACTCCTAGGACTTTGATCTTTTAAA 1690

Query:  1165 GGTTTTTTTCCCCAGCATTAATATTGATTTATAAAGATTTGAAAATCTTTTAATGAACTG 1224
             GGTT  T CCCCA C T  A  TT AT T TAA    TTTGAAA TCTTT A TGAACT
Sbjct:  1691 GGTTCCCTCCCCCATCCTCCAC-TTAATAT-TAAT--TTTGAAAGTCTTT-AGTGAACTT 1745

Query:  1225 GAGAACACTAAGATTTAAACTCGAAAATTCGTTGTTCAAGTAAAGAAAGCCATGATGCTC 1284
             G GA CA TAAGATTTAAACT GAAAATTC TTGTTCA TAAAGAAAGCC    GCTC
Sbjct:  1746 G-GA-CATTAAGATTTAAACTTGAAAATTCATTGTTCATTTAAAGAAAGCCGCAGCGCTC 1803

Query:  1285 TGTATGTTATCTGTGTGTGTGCATGCACTCAGGTGCCCTTTGTTTCATGAACAAATACAT 1344
             TGTATGTTATCTGTGTGTGTGCATGCACT AGGTGCC TTTGTTT AT AACA T   T
Sbjct:  1804 TGTATGTTATCTGTGTGTGTGCATGCACTTAGGTGCC-TTTGTTT-ATAAACA--T---T 1856

Query:  1345 TTCATTGTACATGTTTTCTGT-TTAAATCATTGTATAAAGTAATTGCAGGTCAGAATTAT 1403
             TT ATTGTACATGTTTTCTGT TTAA TCATTGTATAAA TAATT A GTCAGAATTAT
Sbjct:  1857 TT-ATTGTACATGTTTTCTGTCTTAAGTCATTGTATAAAATAATTATAAGTCAGAATTAT 1915

Query:  1404 ACCACAGAACTGTTTATGAGAGGCTTGTGT-CTGTTGCACATTTCTTGAAGCATTTTTAA 1462
             AC ACAGAA TGTT T AGAGGCT GT T CT TTGCACATT CTTGAAGCATTT AA
Sbjct:  1916 ACAACAGAAGTGTTAGTAAGAGGCT-GTATTCTATTGCACATTACTTGAAGCATTTTAAA 1974

Query:  1463 AA-----TAACATGTAACCTGTA-ACCTTGTTGTTTAAGTTTTCTTTTCTATTAATACTC 1516
             AA     TAACATGTAACCT TA A   TT TTTAAGTTTTC TTTCTATTAAT CTC
Sbjct:  1975 AAAAAAATAACATGTAACCTATATATAACCTTATTTAAGTTTTCCTTTCTATTAATTCTC 2034

Query:  1517 TGTCCTGTGGTCCC-GTGCATGCTCCTTTTCCCAGAACTCCTCTCTGCTGCACCCACAGC 1575
             TGTCCTGTGG CCC GTGCATGCTCCTT  CCCAGAACTCCTCTCTGC GCAC CACAG
Sbjct:  2035 TGTCCTGTGGCCCCCGTGCATGCTCCTTC-CCCAGAACTCCTCTCTGCCGCACTCACAGA 2093

Query:  1576 A--TCT-GTTCCCGAGGAGTTATGACTCTTGACTTCCTGCAGG-GCTGGGG-CTCTTAGC 1630
             A  TCT GTTCC GAGGAGTTA G CTCT    CTTCC GC G GCT  G CT TTAG
Sbjct:  2094 AGCTCTTGTTCCTGAGGAGTTAGGGCTCTCAGCTTCCAGCTGCTGCTCCTGACTGTTAGT 2153

Query:  1631 CACCAGCTGCTGTTCCAGC-ACTTTCAGCGCAAGATCTCCCTGATTTTGCCACGTGGAAT 1689
                C AG T TG   A TT C  GCA G TCT C T AT T    A  AAT
Sbjct:  2154 GCCTAGTTT-TGCCAAATAGAATTACTATGCA-G-TCTGCTT-ATCTAAA-ATGAAAAAT 2208
```

Fig. 4C-1

```
Query:  1690 TGTACTTGTATATGATTACCTTATCTAAAATGAATAAGAGG---TGATGGACCAGTTTAC 1746
              G   TT A   G TTAC T   T TA A    A AAGAGG    TG TG A  A TTT C
Sbjct:  2209 AGGTTTTCAACCAGTTTAC-TGCT-TAGAGACAGCAAGAGGCACTGCTGTAAAA-TTT-C 2264

Query:  1747 TGC-TTAGAAA-TAGCAAGAGGCACTGCA--GTAAA-ACTTGTTTCTCATTGTAAAGC-T 1800
              T C TTA AAA TA CA G  G    GT A  AC T T T T AT   TAAAG T
Sbjct:  2265 TCCATTATAAAGTAACATGTCGTTTGGTTTGGTTAGGACATTTATAT-ATA-TAAAGAAT 2322

Query:  1801 TCAT-GTCTTTTGTT-TGTTGGAAAATTTTTACTTATAGAAACTTAATTATTAGACT-GG 1857
              T AT G          T TT    AAA T T  C  ATA AA TTAA  AT  G C GG
Sbjct:  2323 TGATTGAAACCAACACTATTAACAAAATATG-CAGATACCAAATTAAC-ATC-GTCAAGG 2379

Query:  1858 TAA--AATAAAGACCAAAATATGCAGAT-TTCTAATTGGCATTCATAAGGTGAATAATAA 1914
              T    AATAA  ACCAA  TA G A  T TT T ATT  CAT CAT A     AT AT A
Sbjct:  2380 TTCTCAATAAGTACCAAGTTA-GAAATTATTATCATTATCAT-CATTATTATTATTATTA 2437

Query:  1915 TAAGTGCCCAATGAAAAA-ATCTATTATGGTTAATTTCATTTCTTGCTTTGCCACCTAAG 1973
              T A T    C A T A  A  ATC ATTAT  TT  TT C    CT GC A    AA
Sbjct:  2438 TTATTATC-A-TCATCATC-ATTAT--TTC-TTGCTTTGCCACCTAAGC-AGTAAAA 2490

Query:  1974 CAGTAAAAC-A-TGATATTGACCACTTGGAGAACTCAGAAAATTATTTAAATTTCTAAG 2031
              CA T A A   A T  T  TGA ACT G GAA T  A  A ATT   AA TT A G
Sbjct:  2491 CAATGATATTAGTCCTTTGGAGAACTGAG-GAAATTACTTTAA-ATTCCCAAGTTACA-G 2547

Query:  2032 TTATAATAAATTTGCACACAGATAA--CATGC-ATGCTATTTA-TGTCACATCTCACATT 2087
              T A AAT   T    CACA A A  A  CATG ATG TAT  A T TCACAT T A  TT
Sbjct:  2548 T-A-AATT--TGCACACAGATAACATGCATGTTATG-TATCAAGTTTCACAT-T-ATTTT 2600

Query:  2088 AAATTA 2093    (SEQ ID NO:66)
              AAA TA         (SEQ ID NO:67)
Sbjct:  2601 AAAATA 2606    (SEQ ID NO:68)
```

Fig. 4C-2

Score = 273 (41.0 bits), Expect = 0.0, Sum P(3) = 0.0
Identities = 137/201 (68%), Positives = 137/201 (68%), Strand = Plus / Plus Query: 1041 AACAAACTGTTTCTGTGCAACCCCTTTGTTTTACCAGACAAAATTTGAATACTTTTTTTC 1100
             AA AAACTGTTTCTGTGCAACCCC  TGTTTTACCAGACA AATTTGAA ACTTTTTT
Sbjct: 1576 AAAAAACTGTTTCTGTGCAACCCCACTGTTTTACCAGACAGAATTTGAA-ACTTTTTTG- 1633

Query: 1101 CTGAATTGTATATGACCTTGGTGC-TGCATGCATG-CTGTT-G-ACTTTTAGGACTTTGA 1156
              TG AT    T  G  CT GTGC TGC TG  TG CT  T G ACTTT A   CTTT A
Sbjct: 1634 -TGTATGACCTTGGTGCTGTGTGCCTGC-TGT-TGACTCCTAGGACTTTGAT--CTTTTA 1688

Query: 1157 TCTTTTAAGGTTTTTTTCC-CCAGCATTAATATTGATTTATAAAGA-TTT-GAAAATCTT 1213
              TT           TCC CCA C TTAATATT ATTT  AAAG TTT G AA CTT
Sbjct: 1689 AAGGTTCCCTCCCCCATCCTCCA-C-TTAATATTAATTTTGAAAGTCTTTAGTGAA-CTT 1745

Query: 1214 TTA-ATGAAC-TGGAGAACACTAAGATTTA 1241   (SEQ ID NO:69)
               A AT AA  T  A AAC   AA ATT A       (SEQ ID NO:70)
Sbjct: 1746 GGACATTAAGATTTA-AACTTGAAAATTCA 1774   (SEQ ID NO:71)

Fig. 4D

Blast-X Homology:
>ptnr:SPTREMBL-ACC:Q61110 QUAKING (QKI-7) - MUS MUSCULUS (MOUSE), 325 aa.
Plus Strand HSPs:
 Score = 1686 (593.5 bits), Expect = 8.7e-173, P = 8.7e-173
 Identities = 325/325 (100%), Positives = 325/325 (100%), Frame = +3

```
Query:      6 MVGEMETKEKPKPTPDYLMQLMNDKKLMSSLPNFCGIFNHLERLLDEEISRVRKDMYNDT 185
              MVGEMETKEKPKPTPDYLMQLMNDKKLMSSLPNFCGIFNHLERLLDEEISRVRKDMYNDT
Sbjct:      1 MVGEMETKEKPKPTPDYLMQLMNDKKLMSSLPNFCGIFNHLERLLDEEISRVRKDMYNDT 60

Query:    186 LNGSTEKRSAELPDAVGPIVQLQEKLYVPVKEYPDFNFVGRILGPRGLTAKQLEAETGCK 365
              LNGSTEKRSAELPDAVGPIVQLQEKLYVPVKEYPDFNFVGRILGPRGLTAKQLEAETGCK
Sbjct:     61 LNGSTEKRSAELPDAVGPIVQLQEKLYVPVKEYPDFNFVGRILGPRGLTAKQLEAETGCK 120

Query:    366 IMVRGKGSMRDKKKEEQNRGKPNWEHLNEDLHVLITVEDAQNRAEIKLKRAVEEVKKLLV 545
              IMVRGKGSMRDKKKEEQNRGKPNWEHLNEDLHVLITVEDAQNRAEIKLKRAVEEVKKLLV
Sbjct:    121 IMVRGKGSMRDKKKEEQNRGKPNWEHLNEDLHVLITVEDAQNRAEIKLKRAVEEVKKLLV 180

Query:    546 PAAEGEDSLKKMQLMELAILNGTYRDANIKSPALAFSLAATAQAAPRIITGPAPVLPPAA 725
              PAAEGEDSLKKMQLMELAILNGTYRDANIKSPALAFSLAATAQAAPRIITGPAPVLPPAA
Sbjct:    181 PAAEGEDSLKKMQLMELAILNGTYRDANIKSPALAFSLAATAQAAPRIITGPAPVLPPAA 240

Query:    726 LRTPTPAGPTIMPLIRQIQTAVMPNGTPHPTAAIVPPGPEAGLIYTPYEYPYTLAPATSI 905
              LRTPTPAGPTIMPLIRQIQTAVMPNGTPHPTAAIVPPGPEAGLIYTPYEYPYTLAPATSI
Sbjct:    241 LRTPTPAGPTIMPLIRQIQTAVMPNGTPHPTAAIVPPGPEAGLIYTPYEYPYTLAPATSI 300

Query:    906 LEYPIEPSGVLEWIEMPVMPDISAH 980    (SEQ ID NO:16)
              LEYPIEPSGVLEWIEMPVMPDISAH        (SEQ ID NO:16)
Sbjct:    301 LEYPIEPSGVLEWIEMPVMPDISAH 325    (SEQ ID NO:16)
```

Fig. 4E

METHOD OF IDENTIFYING A PSYCHOTROPIC AGENT USING DIFFERENTIAL GENE EXPRESSION

RELATED APPLICATIONS

This invention claims priority to U.S. Ser. No. 60/113,127, filed Dec. 21, 1998. The contents of the application are incorporated by reference in their entirety.

FIELD OF THE INVENTION

The invention relates generally to nucleic acids and polypeptides and in particular to the identification of psychotropic agents using differential gene expression.

BACKGROUND OF THE INVENTION

Neuroleptics are agents that are used to treat psychotic disorders such as schizophrenia. They can cause side effects that cause disruptions of the motor system.

In humans, they further reduce initiative and interest in environmental stimuli, and suppress manifestations of emotion. An important neuroleptic agent is haloperidol, a member of the butyrophenone (phenylbutylpiperidine) class of heterocyclic antipsychotic agents used in the treatment of schizophrenia. Other members of the butyrophenone class include droperidol, a short-acting highly sedative compound used for anaesthesia induction and pimozide, a potent neuroleptic with prolonged action used to prevent involuntary vocalizations of Tourette's Syndrome. The butyrophenone antipsychotics have been demonstrated to have selective D2 dopaminergic receptor antagonism. (Goodman & Gilman's The Pharmacological Basis of Therapeutics, Ninth Edition, Hardman, JG et al. (eds), McGraw-Hill, New York, 1996, p.406) Additionally, haloperidol has also been shown to have binding activity with sigma receptors (Seth et al, J Neurochem 70).

In the psychotic patient, following several days of neuroleptic administration, "positive symptoms" such as agitation, hallucinations, delusions, disorganized thought tend to disappear and there are some effects on"negative symptoms" as withdrawn or autistic patients can sometimes become more communicative. Overall, however, haloperidol and its chemical relatives are most noted for their treatment of "positive symptoms" and have little effect on most catatonic patients. (Goodman & Gilman, Ninth Edition, p.407)

Dosing of haloperidol typically requires a 10 mg–16 mg loading dose followed by maintenance therapy of 12 mg–30 mg per day in divided doses. Dosing is individualized to allow patients to take the minimally necessary dose that alleviates symptoms (Harrison's Principles of Internal Medicine, 13$^{th}$ ed., Fauci, AS et al. (eds.), McGraw-Hill, New York, 1994, p.2418). Because psychotic disorders are chronic diseases, and controlled studies have demonstrated relapses within 6 months in 60% of all patients, sustained therapy is recommended.

A prevalent side effect of both butyrophenone and phenothiazine (e.g. chlorpromazine) neuroleptics is the induction of extrapyramidal motor pathology. Extrapyramidal symptoms include parkinsonism, akathisia, dystonia and tardive dyskinesia. Such symptoms are apparent with both acute and chronic administration of neuroleptic drugs (Gill, HS et al., J. Clin. Psychopharm. 17(5):377–389(1997)). Dystonias typically appear within the first few days of therapy. These can manifest as either Parkinsonian-like tremors or as uncontrollable, spastic muscle contractions that produced anormal postures. Dystonic movements are typically slow, writhing movements that are transiently sustained. Ones that affect the eye muscles can be particularly disturbing as the patient loses ability to focus visually. In most patients coadministration of haloperidol with benzotropine or trihexyphenidyl (two anti-muscarinic agents) can reduce or alleviate the dystonic and Parkinsonian manifestations. Sustained, chronic use can induce tardive dyskinesia, a broad spectrum of hyperkinesias associated with exposure to neuroleptic drugs within 6 months of the onset of symptoms (although the patient has probably been on the drug for several years) which persists for 1 month after discontinuation of the neuroleptic agent. The most common movement manifestations of tardive dyskinesia involve repeated tongue protrusions and lip smacking. About 30% of all patients exposed to neuroleptic therapy develop some form of persistent movement disorder.

Development of extrapyramidal symptoms, and especially tardive dyskinesia as a consequence of long-term neuroleptic administration has been recognized for almost 4 decades. Tardive dyskinesia remains the most feared and disconcerting extrapyramidal side-effect of chronic treatment (Walters, VL et al., Schizophrenia Res. 28:231–246 (1997)). At the present time, therefore, prevention is best accomplished by intervening prior to the development of extrapyramidal symptoms (Walters et al. (1997)). Alternatively, although a variety of treatment therapies have been attempted in the treatment of tardive dyskinesia, none has become manifest as being successful in most patients (Egan, MF et al., Schizophrenia Bull. 23(4):583–609 (1997)).

From the above description of the manifestations of tardive dyskinesia and related motor dyskinesias, it is apparent that there is a compelling need for identifying alternative neuroleptic agents whose beneficial effects in the treatment of schizophrenia remain essentially undiminished from those in use currently, but which do not induce the symptoms of tardive dyskinesia. There further is a need for developing methods useful in screening pharmaceutical agents that are potential or candidate neuroleptics for their avoidance of the development of tardive dyskinesia. There is additionally a need for identifying molecular and cell biological bases for carrying out such methods. The present invention recognizes these deficiencies, and addresses their resolution.

SUMMARY OF THE INVENTION

The invention is based in part on the discovery that certain genes are differentially expressed in the brain striatum regions of animals treated with therapeutic levels of the common neuroleptic, haloperidol. These differentially expressed genes include novel and genes that, while previously described, have not heretofore been identified as haloperidol responsive.

Identification of the differentially expressed genes or gene fragments permits their use in identifying patterns of gene expression that produce the effects of tardive dystonia and similar dyskinesias when previously uncharacterized candidate neuroleptics are administered to a test system or to a test animal. Thus, the discovery allows for the identification of psychoactive agents, e.g. neuroleptic agents, which do not produce a pattern of differential gene expression characteristic of tardive dystonia and similar dyskinesias.

In various aspects, the invention includes methods of a method of identifying psychotropic agents, methods of diagnosing movement disorders, and methods of treating movement disorders. For example, in one aspect, the invention provides a method of identifying a psychotropic agent that does not induce a significant motor side effect by providing a test cell population comprising a cell capable of expressing one or more genes responsive to haloperidol, contacting the test cell population with the psychotropic agent; and comparing the expression of the gene in the test cell population to the expression of the gene in a reference cell population. An alteration in expression of the gene in the test cell population compared to the expression of the gene in the reference cell population indicates the psychotropic agent does not induce a significant motor side effect.

The invention in a further aspect includes a method of selecting a psychotropic agent appropriate for a particular subject. The method includes providing from the subject a cell population comprising a cell capable of expressing one or more genes one or more genes responsive to haloperidol, contacting the cell population with the psychotropic agent, and comparing the expression of the gene to the expression of the gene in a reference cell population. An alteration in expression of the gene in the test cell population compared to the expression of the gene in the reference cell population indicates the psychotropic agent is appropriate for the subject.

In a further aspect, the invention provides a method of diagnosing or determining susceptibility to a movement disorder in a subject. The method includes providing from the subject a cell population comprising a cell capable of expressing one or more haloperidol-responsive genes, and comparing the expression of the gene to the expression of the gene in a reference cell population that includes cells from a subject not suffering from a movement disorder. An alteration in expression of the gene in the test cell population compared to the expression of the gene in the reference cell population indicates subject has or is susceptible to a movement disorder.

Also provided are novel nucleic acids, as well as their encoded polypeptides, whose expression is responsive to the effects of haloperidol. Included are nucleic acids encoding two full-length human quaking homologs were identified. They are named human Qk5 and Qk7, for quaking splice variant 5, and human quaking splice variant 7, respectively.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a representation of the nucleic acid sequence (SEQ ID NO:13) and the encoded amino acid sequence (SEQ ID NO:14) of the human Qk5 isoform..

FIG. 2 is a representation of the nucleic acid sequence (SEQ ID NO:15) and the encoded amino acid sequence (SEQ ID NO:16) of the human Qk7 isoform.

FIGS. 3A–3C are representations of regions of sequence homologies between the murine quaking nucleotide sequence and the human Qk5 nucleotide sequence.

FIG. 3D is a representation of sequence homology between the chicken quaking protein sequence and the human Qk5 protein sequence.

FIGS. 4A–4E are representations of regions of sequence homologies between the murine quaking nucleotide sequence and the human Qk7 nucleotide sequence.

DETAILED DESCRIPTION OF THE INVENTION

The present invention is based in part on the discovery of changes in expression patterns of multiple nucleic acid sequences in the striatum of the brain in animals treated with therapeutic levels of the neuroleptic haloperidol. Changes in expression are observed in both heretofore undescribed nucleic acid sequences and previously identified nucleic acids. The discovery provides the basis for methods of screening for pharmacological agents which exhibit antipsychotropic properties but which do not induce the changes in gene expression associated with haloperidol.

Rats treated with haloperidol for 28 days manifest motor disturbances that parallel human pathology, suggesting the usefulness of this treatment as a model for neuroleptic-induced motor disease. Accordingly, the differentially expressed genes were identified by treating Wistar rats with haloperidol (0.041 mg/kg/d for 3 days via continuous infusion Alza pump), or rats treated with vehicle only for 3 days.

Rats were then sacrificed, their brains were removed, and total RNA was recovered from the microdissected striatum. cDNA was prepared and the resulting samples were processed through 140 subsequences of GENECALLING™ differential expression analysis as described in U.S. Pat. No. 5,871,697 and in Shimkets et al., Nature Biotechnology 17:198–803 (1999).

101 gene fragments were initially found to be differentially expressed in rat striatum in response to haloperidol. The differential expression of 50 of the gene fragments was confirmed using a unlabeled oligonucleotide competition assay as described in Shimkets et al., Nature Biotechnology 17:198–803. 32 single copy nucleic acid sequences genes and 5 repetitive copy nucleic acid sequences differentially expressed in haloperidol and vehicle treated striatum were selected for further analysis elements. The 32 single nucleic acid sequences identified herein, as well as 4 sequences previously reported to demonstrate haloperidol-responsive gene expression, are referred to herein as HALOX, to denote that they are haloperidol-responsive sequences.

A summary of the sequences analyzed is presented in Table 1. For five of the nucleic acids, designated (HALO1–5), no homology was found to nucleic acid sequences in public databases. Thus, these represent novel gene fragments in rat.

13 sequences (HALO:6–18) represent novel rat genes for which the sequence identity to sequences found in public databases is either high (i.e., >~85%, observed for 7 fragments), or moderate (i.e., between about 65% and about 80%, observed for 6 genes) suggesting a putative homology.

14 sequences (HALO 19–32) were previously described but have not previously been recognized as being differentially expressed as part of a haloperidol response in the striatum. Of these 14 genes, three genes (quaking, 2'–3' cyclic nucleotide phosphodiesterase II and V-1 protein) have significant relationship to the regulation of myelin formation. Thus, they may be relevant to the onset of dystonic reactions associated with haloperidol. Five genes (neurogranin, Ca+2 ATPase, ankyrin isoform, rab Sc-like protein and synaptophysin) have significant relationship to synaptic vesicle release; and 6 genes (phosphatidyl inositol 3 kinase, inositol 1,4,5 triphosphate 3 kinase, NGFI-A, Jun B, Meis 2 and NGFI-B) are directly involved in signal transduction.

Without wishing to be bound by theory, the present inventor believes that motor dystonias, such as that manifested in Parkinsonism, and presumably that found in tardive dyskinesia as well, is due to a dysfunction in certain areas of the brain. In particular, it is believed that the substantia nigra releases dopamine, which is detected at the synapse by neurons whose axons reach the brain striatum. It is believed that neuroleptics achieve their effects by simulating dopamine reception, which helps alleviate Parkinson-like symptoms. Further without wishing to be bound by theory, the present inventor understands that mice that lack the gene termed quaking exhibit tremor and epileptic-type symptoms. The inventor further hypothesizes that normal mammals such as humans and rats are endowed with the ortholog of the quaking gene in the fetal and neonatal stages of life, and that they may experience down-regulation of this, and related genes, as a result of the administration of neuroleptics such as haloperidol. As a further hypothesis, the present inventor believes that the transient reduction or elimination of expression of genes such as quaking is responsible for development of tardive dyskinesia and related pathologies.

For some of the novel sequences (i.e., HALO 1–18), a cloned sequence is provided along with one or more additional sequence fragments (e.g., ESTs or contigs) which contain sequences substantially identical to, the cloned sequence. Also provided is a consensus sequences which includes a composite sequence assembled from the cloned and additional fragments. For a given HALO sequence, its expression can be measured using any of the associated nucleic acid sequences may be used in the methods described herein. For previously described sequences (HAL019–36) database accession numbers are provided. This information allows for one of ordinary skill in the art to deduce information necessary for detecting and measuring expression of the HALO nucleic acid sequences.

The haloperidol-responsive nucleic acids discussed herein include the following:

TABLE 1

| Description of sequence | Confirmed Bands | Sequence Database Reference | Haloperidol Effect on Transcript Level | HALOX Assignment | SEQ ID NO |
|---|---|---|---|---|---|
| Haloperidol Responsive Novel Nucleic Acid Sequences ||||||
| Novel gene fragment, 86 bp | r0w0__85.5 | — | −2.9 | HALO1 | 1 |
| Novel gene fragment, 121 bp | r0j0__120.6 | — | −2 | HALO2 | 2 |
| Rat novel gene fragment, 495 bp | y0p0__314.6 | — | −2.5 | HALO3 | 3, 4 |
| Novel gene fragment, 649 bp | m1s0321.4 | — | −3 | HALO4 | 5, 6, 7, 8 |
| Novel gene fragment, 539 bp | g1n0__114.5 | — | −1.5 | HALO5 | 9 |
| Novel gene fragment, 262 bp 95% similarity to mouse quaking gene type 1 [U44940] | m1s0__354.3 | U44940 | −2 | HALO6 | 10, 11, 12 |
| Novel gene fragment, 420 bp Nucleotides 266-31 are 86% similar to human U1 snRNP 70 kDa protein [M57936] | s0y0__330.3 | M57936 | −1.7 | HALO7 | 17, 19, 20 |
| Novel gene fragment, 179 bp 91% similar to mouse phosphatidylinositol 3 kinase 1110kD subunit [U03279] | l0t0__177.6 | U03279 | −2 | HALO8 | 21 |
| Novel gene fragment, 94 bp 98% similar to mouse meis2 [U57343] subfamily | i0s0__93.4 | U57343 | +1.6 | HALO9 | 22 |
| Novel gene fragment, 279 bp 89% similar to human rab5c-like protein [U11293] | m0s0__228.7 | U11293 | −2.0 | HALO10 | 23, 24, 25, 26, 27 |
| Novel gene fragment, 516 bp 88% similar to human KIAA0383 gene[AB002381] | i0n0__242 | AB002381 | −2.0 | HALO11 | 28, 29 |
| Rat novel gene fragment, 859 bp 83% homologous to mouse EGF repeat transmembrane protein RJ57368] | s0t0__t218.3 | Y57368 | +3 | HALO12 | 30, 31 |
| Novel gene fragment, 472 bp 80% similar to human suilisol [L26247] | i0s0__93.4 | L26247 | +6.3 | HALO13 | 32, 33 |
| Novel gene fragment, 408 bp 72% simitar to rat repetitive ribosomal DNA II 3' to 45S pre-rRNA [X02822] | w0n0__402.9 | X02822 | −5 | HALO14 | 34, 35, 36, 37, 38 |
| Novel gene fragment, 138 bp 97% similar to mouse gene fragment, 1849 bp with 44% amino acid similarity to human sorting nexin-2 | m0r0__128.4 | TR:G2827434 | +1.0 | HALO15 | 39 |
| Novel gene fragment, 176 bp 70% similar to E. coli putative ATP-dependent RNA helicase RHLB [P24229] | r0t0__371.2 | P24229 | −8 | HALO16 | 40, 41, 42, 43, 44 |
| Novel gene fragment, 600 bp 360 bp region having 65% similarity to 5' region of human NOF1 [U39400] | g1n0__114.5 | U349400 | −10 | HALO17 | 45 |

TABLE 1-continued

| Description of sequence | Confirmed Bands | Sequence Database Reference | Haloperidol Effect on Transcript Level | HALOX Assignment | SEQ ID NO |
|---|---|---|---|---|---|
| Novel gene fragment, 561 bp Encoded polypeptide 80% similar to human predicted protein DJ257A7.1 [AL008729] | s0t0__365.5 | AL008729 | −2.5 | HALO18 | 46, 47, 48, 49, 50 |
| Previously Described Nucleic Acid Sequences Newly Shown To Be HALOperidol Responsive | | | | | |
| Ribosomal protein L18a | s0v0__147.6 | X14181 | +1.8 | HALO19 | |
| Inositol 1.4.5-triphosphate 3-kinase | b1i0__312.0 | M29787 | +2 | HALO20 | |
| 2'-3' cyclic nucleotide 3' phosphodiesterase [CNPII] | b1i0__218.6 | L16532 | −3 | HALO21 | |
| NGFI-B | 10w0__97.2, w0i0__180.8 | U17254 | +2.4 | HALO22 | |
| Neurogranin | gln0__117.5 | L09119 | +1.1 | HALO23 | |
| V-1 protein | d0v0__180.9 | D26179 | −2.0 | HALO24 | |
| 190 kDa ankyrin isoform | m1l0__366.9 | F069525 | −2.0 | HALO25 | |
| Cathepsin S | w0h0__124.3 | L03201 | −1.7 | HALO26 | |
| D-Amino acid oxidase | g1i0__267.4 | B003400 | −2.0 | HALO27 | |
| Stomach nonmuscle Ca$^{+2}$ ATPase | s0v0__133.8, m1y0__132 | J04023 | +2 | HALO28 | |
| L1 retrotransposon ORF2 | i0s0__66.7 h0r0__83.9 d0p0__218.8 h0a0__373.9 r0a0__132.0 h0r0__409 i0n0__250.9 i0n0__65.1 | U83119 | −3.3 | HALO29 | |
| Lone interspersed repetitive DNA sequence LINE3 | d0p0__279.9 m0r0__118.4 d0p0__132 | 13100__5 | −5 | HALO30 | |
| Long interspersed repetitive DNA containing 7 ORFs | i0a0__82.8 d0g0__218.8 | 53581__2 | −3.5 | HALO31 | |
| L1 retrotransposon mIvi2-rn38 | h0r0__120.4 | U87604 | −5.5 | HALO32 | |
| Known Nucleic Acid Sequences Previously Demonstrated To Be Haloperidol Responsive | | | | | |
| NGF1-A | b1i0__218.6 | M18416 | −3 | HALO33 | |
| JunB | g0c0__264.7 | X54686 | +4 | HALO34 | |
| Synaptophysin [p38] | f0k0__242.0 | X068388 | ±1.0 | HALO35 | |
| Phosphatidyl-inositol-3-kinase | | U03279 | | HALO36 | |

Below follows additional discussion of nucleic acid sequences whose expression is differentially regulated in the presence of haloperidol.

HALO1, a novel 86 bp gene fragment

The nucleic acid has the following sequence:

```
  1 gaattcagcc agggatcgcc cgtgctcaat gacctcactg ccatcctgga cttggcttgc   (SEQ ID NO:1)
 61 ctagatctcc tgctccagtt gctgc
```

Its expression is decreased 2.9-fold in haloperidol-treated rats.

HALO2, a novel 121 bp gene fragment

The nucleic acid has the following sequence:

```
  1 gaattcattg gaaagccaaa cgggtcattt gcagttaccc cctccaaccc accccacag   (SEQ ID NO:2)
 61 tcttaaagct gtgctcactg ggatagaaca caaatggcta agcacaggga atgtgcgtac
121 g
```

Its expression is decreased 2-fold in haloperidol-treated rats.

HALO3, a novel rat gene fragment

The nucleic acid was identified in a cloned fragment having the following sequence:

```
  1 actagtaaaa gcttctaact cttcttgttg ttcattttttt ttccttttttc ttctttgttt  (SEQ ID NO:3)
 61 ggattgcagc attctgctct tctgatgatg cgctgtgacc ctgaaagtag cgcaaaggct
121 gcgcaggtta atgcgcattg cgtgcgaatg agcccctgtg aacggttgac tagatgagta
181 atctgattga ctggctctct cagtcctatt ctgtagcctt tttggataaa attgggtttt
241 aacgtaccttt gagtccaact aatctcatta agtaaatatt ctctatgggc ctgtctagta
301 gattaatgga tcy
```

It is also provided assembled into a contig that includes EST AA875524, to provide the consensus sequence:

```
  1 ACTAGTAAAAGCTTCTAACTCTTCTTGTTGTTCATTTTTTTCCTTTTTCTTCTTTGTTTGGATTGCAGCATTCTGCTCT  (SEQ ID NO:4)

81 TCTGATGATGCGCTGTGACCCTGAAAGTAGCGCAAAGGCTGCGCAGCGTTAATGCGCATTGCGTGCGAATGAGCCCCTGT

161 GAACGGTTGACTAGATGAGTAATCTGATTGACTGGCTCTCTCAGTCCTATTCTGTAGCCTTTTTGGATAAAATTGGGTTT

241 TAACGTACCTTGAGTCCAACTAATCTCATTAAGTAAATATTCTCTATGGGCCTGTCTAGTAGATTAATGGATCNTGGTTG

321 GCCGTTTGCTGCGTCTAGGGGTGTTCTATGTAGCGCAGCAGTTCGCAGCGATTGCGCAGTGCGATGCTGTTAGGTGGCGC

401 CAGCGATGTTTGCGCTCGCATTACAGGGACATCAACCTAGGTGCAATCCTGTCATGTGAGGTTTTATTTTCTTCCTCCTC

481 AGAAGAGAAGTGTTATGAATCTGAAACTTAAAGCCTAAAGGATAATGACCGACTTGGCAGAAAGATTTTTTA
```

HALO4, a novel 649 bp new gene fragment

The nucleic acid was initially identified in a cloned fragment having the following sequence:

```
  1 aagcttgtca gtgcacacat agatggtcgg catgtttagc aaactttgtg aaatttaaat  (SEQ ID NO:5)
 61 aagtttgtag ttacatgtga aactctaaat gcatggtaac cgttgatgtc ataacagttt
121 agttatttcg ttctgttctg tcatgtgcca caaaataagt ntcttttttca cctttttttt
181 gttttttttgg ttttttgttt ttttggtttt tcctgttttt tttgcccttt gtanattant
241 tgaggttaaa actggttcat cctgaaaaaa acgacgaaaa aaancgaaaa agtccattca
301 tattttttaa caattg
```

The cloned sequence was assembled onto a contig that includes EST AA891494:

caattgtataagtncccaagtcattcac-
tacaccctcangccttgcntttg-
taatttgacttctgaaatgtcggcgat-
caaagcatgcacctgtaccaatgacaaaagaaaaagcattt
tatattactactcaataaaatgtgcat-
gaacttaaagaatgctcatcctttcact-
gagtctgctgaagggaatgccatgcg-
caccaccacggtgtcctctgggtgctggccctteccacccctgcaca
cttaggataggctgcttcccagggacctcacgatataaggagcggtacc
(SEQ ID NO:6)

The resulting assembled sequence includes:
GGTACCGCTCCTTATATCGTGAGGTC-
CCTGGGAAGCAGCCTATCCTAAGTGTG-
CAGGGTGGGGAAGGGCCAGCACCCAGAG-
GACACCGTGGTGGTGCGCATGGCATTCCCTT or CAAATTACAAAGGCAAGGCTTGAGGGTG-
TAGTGAATGACTTGGGCACTTATACAAT-
TGTTAAAAAATATGAATGGACTTTTCTGCTGTT
TGTCGTCGTTGTTTTCAGAATGAAC-
CAGTTGTAACCTCAACTAATATA-
CAAAGGGCAAAAAAAACAAAAAAAAA-
CAAAAAAAAACAAAAAAACAAAAAACCAAA
AAAACAAAAAAAAAGGTGAAAAAAAG-
TACGTATTTGTGGCACATGACAGAACA-
GAACGAAATAACTAAACTGTTATGACAT-
CAACGGTTACCATGCATTTAGAGTTTCACATG
TAACTACAAACTTAATTAAATTTCA-
CAAAGTTTGCTAAACATGCCGACCATC-
TATGTGTGCACTGACAAGCTTATGT-
TAAAAACTTTTAAGAATACT (SEQ ID NO:7)

```
  1 GGTACCGCTCCTTATATCGTGAGGTCCCTGGGAAGCAGCCTATCCTAAGTGTGCAGGGTGGGGAAGGGCCAGCACCCAGA  (SEQ ID NO:8)
 81 GGACACCGTGGTGGTGCGCATGGCATTCCCTTCAGCAGACTCAGTGAAAGGATGAGCATTTTTTTTCTTTAAGTTCATG
161 CACATTTTATTGAGTAGTAATATAAAATGCTTTTTCTTTTGTCATTGGTACAGGTGCATGCTTTGATCGCCGACATTTCA
241 GAAGTCAAATTACAAAGGCAAGGCTTGAGGGTGTAGTGAATGACTTGGGCACTTATACAATTGTTAAAAAATATGAATGG
321 ACTTTTCTGCTGTTTGTCGTCGTTGTTTTCAGAATGAACCAGTTGTAACCTCAACTAATATACAAAGGGCAAAAAAAACA
401 AAAAAAAACAAAAAAAAACAAAAAAACAAAAAACCAAAAAAACAAAAAAAAGGTGAAAAAAAGTACGTATTTTGTGGCAC
481 ATGACAGAACAGAACGAAATAACTAAACTGTTATGACATCAACGGTTACCATGCATTTAGAGTTTCACATGTAACTACAA
561 ACTTATTTAAATTTCACAAAGTTTGCTAAACATGCCGACCATCTATGTGTGCACTGACAAGCTTATGTTAAAAACTTTTA
641 AGAATACT
```

HALO5, a novel 539 bp gene fragment
The fragment includes the following sequence:

```
 1 tctagattgt ctgggctgga gtattctgta tggcctggta gacgggaatg ttctgcacgt  (SEQ ID NO:9)
61 aaatcatgta tcttcagatg ggacatctct taagtattaa tgttgtgtgt aca
```

HALO6, a novel 363 bp gene fragment similar to mouse quaking gene
The 363 bp sequence is provided as the following sequence:

```
  1 caattgggtt tgcctctatt ttggctcctc cttcttttta tccctcatgg agcctttgcn  (SEQ ID NO:10)
 61 ncggaccatt attttacatc ngtttncgac taaagttgtt tagngtaagt accanaggtc
121 naggattana cccaaaaaat taaaatcagg gtattctttt acaggcacat aaagtttctc
181 ttgtaactga acaatgggtc ccaccgcgtn acgcaattct gcactccttt tctctgtact
241 gccatttaat gtgtcattgt acatgtcttt ccgtactctg ctaatttctt cgtccagcag
301 ccgctcgagg tggttgaaga tcccgcagaa gttgggcagg ctgctcataa gctt
```

The fragment is assembled in a contig that includes the following sequence:

```
  1 CAATTGGGTTTGCCCTCTATTTTGGCTCCTCCTTCTTTTTATCCCTCATGGAGCCTTTGCCTCGGACCATTATTTTACAT  (SEQ ID NO:12)
 81 CCTGTTTNCTGACTACAAGTTGTTTAGCTGTAAGTACCACTAGGTCCAAGGATTATACCCAACAAAATTAAAATCCAGGG
161 TATTCTTTTACAGGCACATAAAGTTTCTCTTGTAACTGAACAATGGGTCCCACCGAGTCACGCAATTCTGCACTCCTTTT
241 CTCTGTACTGCCATTTAATGTGTCATTGTACATGTCTTTCCGTACTCTGCTAATTTCTTCGTCCAGCAGCCGCTCGAGGT
321 GGTTGAAGATCCCGCAGAAGTTGGGCAGGCTGCTCATAAGCTT
``` to provide the consensus sequence:

ctcgagcggctgctggacgaagaaatt-
agcagagtacggnaagacatgtncaat-
gacacattaaatggcagtaca-
gagaaaaggagtgcagaattgcctgactcggtgggacccattgttca
gtnacaagagaaactttatntgcctg-
taaaagaatacccctggattt-
taattttgttgggagaatccttggac-
ctagagggacttacagctaaacaacttgaagcagaaacaggatgtaaa
ataatggtccgaggcaaaggctccat-
gagggataaaaagaaggaggagcaaaatagagggcaaacccaattg
(SEQ ID NO:11)

This sequence is 95% similar to the mouse quaking type 1 gene. Its expression is decreased 2-fold in haloperidol-treated rats. The quaking gene is a member of the STAR (signal transduction and activator of RNA) class of proteins. The protein has a domain with homology to hnRNP K (KH domain) which suggests RNA binding activity. The quaking KH domain is most similar to KH domains from *C. elegans* gld-1, a tumor suppressor gene and to Sam68 from humans, a downstream target of src. A new unique domain, called QUA2, located immediately downstream from KH domain is also common to Sam68 and gld-1.

The quaking gene has been identified in mice as being implicated in the maintenance of normal extent of myelination of nerve cell axons and is therefore essential for both embryogenesis and development of the nervous system (Zorn, AM and Krieg, PA, Genes and Dev. 11:2176–2190 (1997); Hardy, RJ et al., J. Neurosci. 16(24):7941–7949 (1996)). The STAR (signal transduction and activation of RNA) family of proteins has been implicated in a variety of functions in development processes (Vernet, C and Artzt, K, Trends in Gen. 13(12):479–484 (1997)). The cloned mice gene(qkl) is transcribed into three messages of 5, 6 and 7 kb (Hardy et al. (1996); Ebersole, TA et al., Nat. Gen. 12:260–265 (1996). Transcription is detected in brain, lung, heart and testes. The translated protein is localized to myelinating tracts in the cerebellum among other locations.

dicted amino acid sequence (SEQ ID NO:14) of human Qk5 is shown in FIG. 1. The nucleotide (SEQ ID NO:15) and predicted amino acid sequence (SEQ ID NO:16) of human Qk5 is shown in FIG. 2. Homology between human Qk5 and Qk7 and mouse quaking nucleotide and amino acid sequences are shown in FIGS. 3A–C and 4A–D, respectively.

These genes are useful as markers for the onset of tardive dyskinesia/dystonias in human subjects taking neuroleptics.

HALO7, Novel 420 bp gene fragment

The sequence was initially identified in the following sequence fragment:

```
  1 actagtggga gggcacatgg aatcgagatg gagaacctga ccctagtatt gagtgctggg  (SEQ ID NO:17)

61 cctgtaccta gtgaaggtga ttgaggcagt ggtgagcagt aggtgttttt gaggccttga 121 ggccactgtt taggttgggc aggatagata gacccaggtc tcccagccca ggtgcaaatc 181 atccctcaga ttctgaggct ccctttttttc cttcatccat gtgtttctag atgntgcggg 241 aaatgtagtc tttccctctc agggttccct gtagctttag ttgccctaat ggtggtgggt 301 gtggggtctg tatgagtact caggtaagct t
```

The quaking protein has a novel function in that it links signal transduction with some aspect of RNA metabolism. The protein may serve as a role for alternative splicing regulation—has been shown that quaking mice have atypical isoforms of necessary myelin proteins.

Quaking was initially characterized as a phenotypic mouse mutant where the mice exhibited tremors and poor coordination. Mice exhibiting the quaking phenotype were found on histological analysis to have abnormally spliced myelin protein. Down-regulation of rat quaking in the striatum following haloperidol administration may suggest direct impact on striatal myelin integrity and supports a hypothesis that this regimen leads to the onset of dystonias. The sequence of the human ortholog of the mouse quaking gene had not been determined prior to the time of the present invention.

Accordingly, two full-length human quaking homologs were identified. They are named human Qk5 and Qk7, for In this sequence bp 266–331 (SEQ ID NO:18) is 86% similar to the human U1 snRNP 70 kDa protein. Its expression is diminished 1.7-fold in haloperidol-treated rats.

The 70 kDa protein is a member of the pre-mRNA to mRNA spliceosome complex. The protein is the major antigen recognized by many autoimmune antibodies The fragment was assembled to form a contig whose sequence is:

gccggcaactcctgggggcctggcgag-
   gaggcgggcttcccgggggtgggg-
   taggggttgggacacgggactgcttac-
   ctggagaccccaagcttacctgagtactcatacagaccccacacccan
   naccattagggcaactaaagctacagg-
   gaaccctgagagggaaagactacatttcccacatcatctaga (SEQ ID NO:19)

The resulting consensus sequence is:

```
  1 ACTAGTGGGAGGGCACATGGAATCGAGATGGAGAACCTGACCCTAGTATTGAGTGCTGGGCCTGTACCTAGTGAAGGTGA  (SEQ ID NO:20)

81 TTGAGGCAGTGGTGAGCAGTAGGTGTTTTTGAGGCCTTGAGGCCACTGTTTAGGTTGGGCAGGATAGATAGACCCAGGTC

161 TCCCAGCCCAGGTGCAAATCATCCCTCAGATTCTGAGGCTCCCTTTTTTCCTTCATCCATGTGTTTCTAGATGATGCGGG

241 AAATGTAGTCTTTCCCTCTCAGGGTTCCCTGTAGCTTTAGTTGCCCTAATGGTGGTGGGTGTGGGGTCTGTATGAGTACT

321 CAGGTAAGCTTGGGGTCTCCAGGTAAGCAGTCCCGTGTCCCAACCCCTACCCCACCCCCGGGAAGCCCGCCTCCTCGCCA

401 GGCCCCCAGGAGTTGCCGGC
``` quaking splice variant 5, and human quaking splice variant 7, respectively. The nucleotide (SEQ ID NO:13) and pre- HALO8, a novel 179 bp fragment
The cloned sequence is:

```
  1 acgcgtqccg tttqttttga cgcaggattt cttaatagtg attagtaaag gagcacaaga  (SEQ ID NO:21)

61 gtacacaaag accagagagt ttgagaggtt tcagngaatg tgttacaagg cgtacctagc 121 aattcgqcaq catgccaatt ctcttcatca accttttctc catgatgctt ggctccgga
```

Its expression is diminished 2-fold in haloperidol-treated rats. In a 179 base portion of this band, 91% of the bases are similar to mouse phosphatidylinositol 3 kinase 110 kDa subunit, which is the catalytic subunit of the PI-3-kinase gene. This kinase phosphorylates the 3' OH group on inositol lipids. The protein has been implicated as participants in signaling pathways regulating cell growth by virtue of their activation in response to various mitogenic stimuli. PI3Ks are composed of a 110-kDa catalytic subunit and an 85-kDa adaptor subunit.

HALO9, a novel 94 bp gene fragment

The cloned sequence is:

```
  1 agatctgctg tggaattggt attgtatgtc catgggatcc tcttttctca gcacgtgttc  (SEQ ID NO:22)

61 ctcactagaa gaaaatgctg ttacctttaa gctt
```

The expression of this sequence is increased 1.6-fold in haloperidol-treated rats, and is 98% identical to murine homeobox protein Meis2 mRNA The latter protein is also referred to as MRG1, and is a member of pbx-related homeobox genes in mammalian systems. Meis proteins bind DNA as part of a heterodimer. The second half of the heterodimers come from other HOX proteins. Depending which other HOX protein is binding to the meis2 adapter, the heterodimer can determine the set of actively transcribed genes.

HALO10, a novel 279 bp gene fragment

The cloned sequence is:

```
  1 tcatgatgga cccttcccct gccccagtg gtggcccgag ttgttaagtg cgattggtta  (SEQ ID NO:23)

61 gagtagattc cagtcaggtc attctgctgg aggagtgggg gcagtggcag gtaaggggct 121 cagttgctgc agcactggct ccggttggct gggttgctct cctgcagatc cacacctctg 181 tttcggcctg gagcaccagc tgcattctgg ggctcaatct tgggaagctt
```

Its expression is diminished 2-fold in haloperidol-treated rats and is 89% simlar to human rab 5c-like protein.

The human rab 5c-like protein was initially identified as a gene sequenced from the BRCA1 candidate region on chromosome 17. Rab proteins are small GTPases involved in the regulation of membrane traffic. Rab5a, rab5b, rab5c all regulate transport in the early endocytic pathway and stimulate the homotypic fusion between early endosomes in vitro and increase the rate of endocytosis when overexpressed in vivo. Rab5c-like protein, RABL, represents a putative small GTP-binding protein from a human fetal lung cDNA library. RABL encodes 216 amino acids that are 86% identical to members of the RAB5 subfamily, and it shows 94% homology in nucleotide sequence with RAB5C of dog. The gene is expressed ubiquitously in all human tissues examined.

The cloned sequence was assembled into a contig that includes the fragments aagcttcccaagaatgagccccagaatg-
cagctggtgctccaggncgaaacagag-
gtgtggatctgcaggagagcaacccagc-
cagccggagccagtgctgcagcaactgagccccttacctgccact gccccactcctccagcagaatgacct-
gactggaatctactctaaccaatca-
cacttaacaactcggaccac-
cnctgggggcaggggaagggtccatcatgaattctccgcataactttgatc
ctagg (SEQ ID NO:24), fragments aagcttcccaagaatgagccccagaatg-
cagctggtgctccaggccgaaacagag-
gtgtggatctgcaggagagcaacccagc-
cagccggagccagtgctgcagcaactgagccccttacctgccactgcc
ccnnctcctccagcagaatggcct-
gactggaatctactctaaccaatcg-
cacttaacaactcgggccaccat-
tgggggcaggggaagggtccatcatgaattc (SEQ ID NO:25)

and fragment ggatccacacctctgtttcnncctggag-
caccagctgcattctggggctcattct-
tgggaagcttcttagctatcgccatgaaaattt (SEQ ID NO:26)

to give the consensus sequence:

```
  1 CCTAGGATCAAAGTTATGCGGAGAATTCATGATGGACCCTTCCCCTGCCCCCAGTGGTGGCCCGAGTTGTTAAGTGCGAT  (SEQ ID NO:27)

81 TGGTTAGAGTAGATTCCAGTCAGGTCATTCTGCTGGAGGAGTGGGGGCAGTGGCAGGTAAGGGGCTCAGTTGCTGCAGCA

161 CTGGCTCCGGCTGGCTGGGTTGCTCTCCTGCAGATCCACACCTCTGTTTCGGCCTGGAGCACCAGCTGCATTCTGGGGCT

241 CATTCTTGGGAAGCTTCTTAGCTATCGCCATGAAAATTT
```

HALO11, a novel 516 bp gene fragment
The cloned sequence is:

```
  1 agatctctct aactttacat tttcattcca tctgtagatt tttctatctt tataaaatat   (SEQ ID NO:28)
 61 tggagttatt ttttaaggaa aaatagaaaa gtagcttgtg aatagctcaa accaagctta
121 cacatcgccg catgtaaaaa gcaggaaagt tatttgtgtc tgtttatgtt gcttcctttt
181 gtagcctttg taccctggac gggtgacagt aagggccgag caggagaggc gcgaccttgt
241 aca
```

Its expression is increased 4-fold in haloperidol-treated rats.

This fragment was assembled into a contig that includes EST AA942662 and EST AA964602 to provide the consensus sequence:

```
  1 GAAGTAACTGACTAAAAAGAGAACGAGATACACACAAGAGTGCTGCTGGCTCCTGTTTTGTACAAGGTCGCGCCTCTCCT   (SEQ ID NO:29)
 81 GCTCGGCCCTTACTGTCACCCGTCCAGGGTACAAAGGCTACAAAAGGAAGCAACATAAACAGACACAAATAACTTTCCTG
161 CTTTTTACATGCGGCGATGTGTAAGCTTGGTTTGAGCTATTCACAAGCTACTTTTCTATTTTTCCTTAAAAAATAACTCC
241 AATATTTTATAAAGATAGAAAAATCTACAGATGGAATGAAAATGTAAAGTTAGAGAGATCTCCATAAAATAGGGACTTCA
321 CACCACACTCACTGTTCCTTGAATCCTGCTGCGTGTTCCGACATGTATGAAATGCTTCAGAACCTGACAGGCAAACACTG
401 AGATATGCTCATTCAATAAACACAAGTGTGCGCTTATAAAACAGAAAGCTGCCTCTCCCCAAAGGAGCCTGTCGCCAAAA
481 TGGAAAAGGGTCTTCTCAACTTTACACCAAACATTT
```

The contig is 88% similar to human mRNA for the KIAA0383 gene, whose function is unknown.

HALO12, a 859 bp novel rat gene fragment
The cloned sequence is:

```
  1 aagcttttat cacgtaacca gctgaacaac acaccaaaag cagcctaggg atgagcaccg   (SEQ ID NO:30)
 61 cgctttggta gcgattaggt tttattcacc tggtattaaa actattcact atttcaaaaa
121 tccggaactt ttaagaattc atttgcaagg cagcatcaaa aactgaaaag gaagggaaaa
181 aaaacaaca gctaataatc ggcttctccg cacgct
```

Its expression is increased 3-fold in haloperidol-treated rats. The cloned sequence was assembled into a contig including EST AA926216, EST AA685607, EST H35630 and EST AA925503 to provide the consensus sequence:

```
  1 CGTTTTATAAATTTAATCATTTGCTAATGGAAATTTTACCACCTCCCATTTGTGTTACAAATCTTAGCTCCTGGAGCGGC   (SEQ ID NO:31)
 81 ACTACAATTCAGGAGTTGTTTTTTCTCACCTCCTCTGTCATTTGTCACAGGAGGTCCCTGCTTGGCAATGACATTTGTGA
161 GTTAGGATAATGACGTTCCTTCTCTCCTTTTTTTTCCTTTCATACTTCAGATTTAGGAGAAAAAGATTCTGTTTCCACG
241 TGAGAGGAACTGTAAGCTTTTATCACGTAACCAGCTGAACAACACACCAAAAGCAGCCTAGGGATGAGCACCGCGCTTTG
321 GTAGCGATTAGGTTTTATTCACCTGGTATTAAAACTATTCACTATTTCAAAAATCCGGAACTTTTAAGAATTCATTTCAA
401 AGGCAGCATCAAAAACTGAAAAGGAAGGAAAAAAAAACAACAGCTAATAATCGGCTTCTCCGCACGCGTGGAGCTCGCG
481 AAACTGGAGCCCCGGAGAAGTGGCTCTGCTCAGCCGCCCGCCCACGCCGCGGCGGTCCTTGCTTTCCCCGCATGCGCCCG
561 CAGGCAGCGTGCAGTCCTAAGCCCGGCTGTGGAGAAGCTCACTCTCTCTTGTTCTGAATGGTGTTTGTGTCGGTCTGC
641 CTCTGTGTATGGTATTATGTCTTATAATCCTGCATCACTTCCATCCTATCCAGTCATATCTAATGTAGAAAAATTAGTTT
```

-continued

```
721 CCAGTGAAAGTAATATGTAGTGCTTTTATGGTATTTGTGTGCAATATCCCCTCTTCTATTGAGGATATTTGATGTAAAGG

801 AAAAAAAAAAGAAAAAAGAAACTGAGTTCCACAATAAAATACAAAGTGGCAAAAGTTC
```

This fragment exhibits 83% similarity to mouse EGF repeat transmembrane protein, whose function is unknown but which is regulated by the IGF-1 receptor.

HALO13, a novel 472 bp gene fragment
  The cloned sequence is:

```
  1 aagcttggta tttgttccct tgtcgtaagt ttaactgata ccaggctggc cttacccttc  (SEQ ID NO:32)

61 atgtttcaac atcccttggc taggagagat ct
```

Its expression is increased 6.3-fold in haloperidol-treated rats. This novel gene fragment of 472 bp is 80% similar to human suilisol (L26247), which is a homolog of the yeast sui1 translation factor.

The fragment was assembled into a contig that includes EST H35427, EST AA848657, EST AA900144 and EST AA875574 to provide the consensus sequence:

```
  1 CACAGTCCCCAGCCCTAGAAGAGTGTCACCATTTGAACAGCCCAGGTGACTGAGAGTATGGGTAACTGCCCCAGCTATAT  (SEQ ID NO:33)

81 CATTAGAGTTGAGTCTCTCTGGCTGTAAAAAGAACCCTTGGTGTCTGACCAGGTAGGCAGAATCCAGAAAGGGCTACCTT

161 TCCAGAGAAGTCATGGACATTAGCTCACCACCAGGGCAGTCTTTTTTAGGCAGATCTCTCCTAGCCAAGGGATGTTGAAA

241 CATGAAGGGTAAGGCCAGCCTGGTATCAGTTAAACTTACGACAAGGGAACAAATACCAAGCTGGTGCTGTTGGTCTTATG

321 GCTAGCTATAAAGGCTTCAACACAATACAAGCCACTGCCCAGTGCCATGTGAAGGAACAAACTGGTCTTTTGGTTTTCTT

401 TTCCCTTCCAGTTTTAATGTTATGTAATGTATTTAAATCCTTATTTAAATAAAGCTTGTTTTCAGAAATAAT
```

HALO14, a novel 408 bp gene fragment
  The cloned sequence is:

```
  1 gctagctgag aggggtggg gtggggcggg gctggagaat atgcaggttc ctgaaggtca  (SEQ ID NO:34)

61 gtcggggaag tactgctgct gccctagcac gcttcagtgc ctctttagag tttagagttt 121 tctaaagttt tctgcctgaa atcagcgagt gatgatttca ctgtgaaatg atgtctgatc 181 atcgctctcg ctgtcctgtc agggctccgg ctcctggcaa atgtctgact gaaggaaacc 241 ttagttagac tcncacccag ctgtttggaa atggtaatgg agttgatagc acaccctggg 301 ggaaaaaggc aaactccctt tttgcnnant ctcaattccc agcctcgcct gcanctcggg 361 gatttnaag
```

Its expression is diminished 5-fold in haloperidol-treated rats.

The cloned fragment was assembled into a contig that includes:
  gctagct-
    gagaggggtggggtggggcggggctg-
    gagaatatgcaggtccctgaaggt-
    cagtcggggaagtactgctgctgccctagcacgcttcagtgcctctttag
    agtttagagttttctaaagttttctgc-
    ctgaaatcagcgagtgatgatttcact-
    gtgaaatgatgtctgat-
    catcgctctcgctgtcctgtcagggctccggctcctggcaaatgtctgact
    gaaggaaaccttagttagactcacac-
    ccagctgtttggaaatggtaatggagt-
    tgatagcacaccctgggggaaagaggca-
    gactccctttttgctcactctcaattcccagcctcgccctgccagttcggg
    gatttctaagtaagggtgaatctggaccanatatgtacttcggaga (SEQ ID NO:35),
  gctagct-
    gagangggggtgggggtggggcggggctg-
    gagaatatgcaggttcctgaaggt-
    cagtcggggaagtactgctgctgccctagcacgcttcagtgcctctttag
    agtttagagttttctaaagttttctgcctgaaatcagcgag tgatgatttcact-
    gtgaaatgatgtctgatca (SEQ ID NO:36), and tgatcatcgctctcgctgtcctgt-
    cagggctccggctcctggcaaatgngt-
    gactgaaggaaaccttagttagactca-
    cacccagctgtttggaaatggtaatggagttgatagcacaccctggggg
    aaagaggcagactccctttttgct-
    cactctcaattcccagcctcgccctgc-
    cagctcggggatttctaagtaagggtgaatctggaccatatatgtaca (SEQ ID NO:37),
``` to provide the consensus sequence:

```
  1 GCTAGCTGAGAGGGGGTGGGGTGGGGCGGGGCTGGAGAATATGCAGGTCCCTGAAGGTCAGTCGGGGAAGTACTGCTGCT  (SEQ ID NO:38)
 81 GCCCTAGCACGCTTCAGTGCCTCTTTAGAGTTTAGAGTTTTCTAAAGTTTTCTGCCTGAAATCAGCGAGTGATGATTTCA
161 CTGTGAAATGATGTCTGATCATCGCTCTCGCTGTCCTGTCAGGGCTCCGGCTCCTGGCAAATGTCTGACTGAAGGAAACC
241 TTAGTTAGACTCACACCCAGCTGTTTGGAAATGGTAATGGAGTTGATAGCACACCCTGGGGGAAAGAGGCAGACTCCCTT
321 TTTGCTCACTCTCAATTCCCAGCCTCGCCCTGCCAGCTCGGGGATTTCTAAGTAAGGGTGAATCTGGACCATATATGTAC
401 ATTCGGAGA
```

In this sequence, 151 bases have 72% similarity to rat repetitive ribosomal DNA II 3' to 45S pre-rRNA [X028222].

HALO15, a 138 bp novel gene fragment

The sequence is 97% similar to a mouse gene fragment 1849 bp in length which has 44% simolarity to human sorting nexin-2 [TR:62827434]. Sorting nexins are a class of moles that target ligand-bound peptide receptors and appropriately target them to the lysosomes for degradation. They are highly hydrophilic but are found partially associated with the plasma membrane. They are widely expressed but each sorting nexin has its own tissue specificity set. Sorting nexin 2 has shown affinity for tyrosine kinase receptors including EGFR, PDGF-R and insulin-R. It also has activity against the long form only of the lepin receptor.

HALO16, a 176 bp novel gene fragment

The cloned sequence is:

```
  1 gaattcacaa caccgggtgg gtaggaaagc agctaacata gcctaggttg gtgcagaagc  (SEQ ID NO:39)
 61 tcacaagaag tggccaggat gtagaggtgg ctgaccaggt aggtagtaag ggcctctact
121 tgccctcctt aacacacaca cctcactcac ggctttgtac aggagcagcc aatggt
```

Its expression is diminished 8-fold in haloperidol-treated rats. A predicted gene product shows 70% similarity over 31 amino acid residues to *E. coli* putative ATP-dependent RNA helicase RHLB, which was identified in the 85-minute region of the *E. coli* genome. The *E. coli* gene encodes a protein sequence with the "D-E-A-D" box motif. Proteins in this gene family occur in eukaryotes as well as prokaryotes, and, as far as tested, have been found to participate in ATP-dependent RNA helicase or RNA-dependent ATPase activities.

HALO17, a 600 bp novel gene fragment

The cloned sequence is:

Its expression is diminished 10-fold in haloperidol-treated rats. The cloned sequence was assembled into a contig that includes EST H317949, actagttcacaactcatttaacccat-
taaaactattctatgtcngccacatg-
gctggttagttacctttcagtttcata-
catctngcttccatctagagttccctgtccaatttccca
caatctaatcctgcctctagctcactg-
gccattagcttttattgacaggtgat-
gcttccacagaatgcacaagagattgtctgtaca (SEQ ID NO:41)

the sequence fragment:

tctagagttcccnntccnntttccca-
caatctaatcctgcctctnnctcnttgtccgnnancttttnatngncaggt-
gatgcttccacagaatgcacaagagatngtctgnacag nnntcangtc-
ngccnngtaagccngatgnttgntgtggcctcctgtnntggacagctttcn (SEQ ID NO:42)

and the fragment accggtatgtataggtatccactt-
naaanctgtccaacacaggangccacan-
caaccatcaggctaacaaggcagacatgactgctgtan (SEQ ID NO:43)

```
 1 tgtacagaca atctcttgtg cattctgtgg aagcatcacc tgtcaataaa aagctaatgg  (SEQ ID NO:40)
61 ccagtgagct agaggcagga ttagattgtg ggaaattgga cagggaactc taga
``` to provide the consensus sequence:

```
  1 TCACCCCNGTTAATGAGNTGACAGGTACCCCTCGAATCAAGGNCCTACTTTGATGAGCAACTTAAANCCTGNCTTCTTGA  (SEQ ID NO:44)
 81 GAAAGGCCTTCTGAGNCCTGATGGTCAGCCCATGTGGCAGTGCTCTCCACAGACTGGCATCCAGAGAGGAAGTGGACTTG
161 GAATCTCTGGAATGGGACACAAAGAACAGAATTTATTCTTAGGATGAAAGGGCTTTGAGATAAGGCCTTGCTTTCGTCAA
```

```
241 GGGGGAGTAGACCGGTATGTATAGGTATCCACTTGAAAGCTGTCCAACACAGGAGGCCACAGCAACCATCAGGCTAACAA

321 GGCAGACATGACTGCTGTACAGACAATCTCTTGTGCATTCTGTGGAAGCATCACCTGTCAATAAAAAGCTAATGGCCAGT

401 GAGCTAGAGGCAGGATTAGATTGTGGGAAATTGGACAGGGAACTCTAGATGGGAAGCNAGATGTATGAAACTGAAAGGTA

481 ACTAACCAGCCATGTGGCNGACATAGAATAGTTTTAATGGGTTAAATGAGTTGTGAACTAGT
```

In a 36 base portion of this sequence there is a 65% similarity to the 5' region of the human NOF1 gene. The term "NOF" represents "Neighbor of FAU." The human was NOF1 gene was isolated during a chromosomal walk along 11q13 in search of a gene responsible for the translocation breakpoint in a particular clone of B-cell NHL. cDNA clones representing NOF hybridized by a 2.2-kb mRNA present in all tissues tested. The largest open reading frame appears to contain 166 amino acids and is proline rich. The sequence shows no homology with any known gene in the public databases. The NOF gene consists of 4 exons and 3 introns spanning approximately 5 kb, and the boundaries between exons and introns follow the GT/AG rule. The NOF locus is conserved during evolution, with the predicted protein having over 80% identity to three translated mouse and rat ESTs of unknown functions. The NOF1 gene is not the gene responsible for the translocation in the 11q13 chromosomal region.

HALO18, a 561 bp novel gene fragment

The cloned sequence is:

```
  1 aagcttcaga cattatggat ggaccagatc ctggcgcccc cgtgaaattg ccttgtctgc  (SEQ ID NO:45)

61 cagtgaaact gtcgcctccg ctaccccccaa aganagtcct gatctgcatg cctgtagggg 121 gcccagagct ctccctggca ccctacgcag cccagaagag cagccagcag gtgttggccc 181 agcaccacca caccgtcctg ccatcccaga tgnagcacca gctgagttat tcgcagccac 241 ggccagcatc tccgctcctc caccggcacc ttacccatgc accctcggg ctgcaggatg 301 atcgatnagc tgaacaagac ncttgctatg accatgcagn ggctggaaag ctccgagnaa
```

Its expression is diminished 2.5-fold in haloperidol-treated rats. This fragment was assembled into a contig that includes fragment:

acgcgttnctcggagctttccagcctct-gcatggtcatagcaagtgtcttgt-tcagctcatcgatcatcctgcagc-ccgaggggtgcatgggtaaggtgncggtggagga cgggagatgctggccgtggctgccat-actgcagctggtgctgcatctgggatg-gcaggacggtgtggtggtgctgggcca-cagcctgctggctgctcttctgggctgcgtaggatgccag ggagagctctggggcc (SEQ ID NO:46)

the fragment
nnccccagagctctccctggcatc-ctacgcngcccagaagagcanccagcag-gttgtggcccagcaccaccacaccgtc-ctnccatcccanatgcagcaccagctnagtatggcagc cacggccagcatctcccgtcctccaccg-gcaccttacccatgcaccctcgggctg-cagggatgatcgatgagctgaacaaga-cacttgctatgaccatgcagaggctggaaagctccgag caacgnttccctgctccacttcttaccacagctctggttttgcacn (SEQ ID NO:47), the fragment
ncccgttnctcgntgctttccagcctct-gcatggtcatagcaagngtctttttcg-gctcancgatcatcctgcagc-ccgaggggtgcatgggtaaggtgncggtggaggacg ggagatgctggccgtggcgccatact-ncagctggtgctgatctgggatgggcag-gacggtgtggtgntgctgggccacagc-ctgctggctgctcttctgggctgcttaggatgccaggganagctctgggcn (SEQ ID NO:48), and the fragment agatctacgntaaagatggagagctctc-catatcaaatgaagatnactccctca-caaacggccagtccctgagctccagc-cagctctctttgcctgctctgtcggaaatggagcctgtccca tgcccagggacccctgctcatatgaggt-gctccaagcttcagacattatggatggaccagatcctggcgcc (SEQ ID NO:49)

to generate the consensus sequence:

```
  1 NGTGCAAAACCAGAGCTGTGGTAAGAAGTGGAGCAGGGGAACGCGTTGCTCGGAGCTTTCCAGCCTCTGCATGGTCATAG   (SEQ ID NO:50)

81 CAAGTGTCTTGTTCAGCTCATCGATCATCCTGCAGCCCGAGGGGTGCATGGGTAAGGTGCCGGTGGAGGACGGGAGATGC

161 TGGCCGTGGCTGCCATACTGCAGCTGGTGCTGCATCTGGGATGGCAGGACGGTGTGGTGGTGCTGGGCCACAGCCTGCTG

241 GCTGCTCTTCTGGGCTGCGTAGGATGCCAGGGAGAGCTCTGGGGCCCCCTACAGGCATGCAGATCAGGACTNTCTTTGGG

321 GGTAGCGGAGGCGACAGTTTCACTGGCAGACAAGGCAATTTCACGGGGCGCCAGGATCTGGTCCATCCATAATGTCTGA
```

```
-continued
401 AGCTTGGAGCACCTCATATGAGCAGGGGTCCCTGGGCATTGGGACAGGCTCCATTTCCGACAGAGCAGGCAAAGAGAGCT 481 GGCTGGAGCTCAGGGACTGGCCGTTTGTGAGGGAGTNATCTTCATTTGATATGGAGAGCTCTCCATCTTTANCGTAGATC

561 T
```

In a 103 amino acid fragment of a putative gene product there is 80% amino acid identity to human predicted protein DJ257A7.1.

HALO19

HALO19 corresponds to a nucleotides encoding a component of the large ribosomal subunit L18a [X14181]. Its transcription is increased 1.8 fold in haloperidol-treated rats. This sequence includes two zipper-like domains and has been shown to interact with Jun in the zipper region.

HALO20

HALO20 corresponds to a nucleotides encoding inositol 1,4,5, triphosphatase [M29787]. Its expression is increased 2-fold in haloperidol-treated rats. The kinase phosphorylates 1,4,5 inositol triposphate on the 3' position to add a fourth phosphate. The kinase functions in signal transduction.

HALO21

HALO21 corresponds to 2',3' cyclic nucleotide 3' phosphodiesterase (CNPII) [L16532]. Its expression decreases 3.0 folf in haldoperidol-treated reats.

It exiss in multiple isoforms. A larger isoform of phosphodiesterase localizes to CNS. The protein is associated with myelination in the CNS. Its conserved motifs include two leucine repeat heptads, and two consensus motifs for phosphorylation in the N-terminal domain of CNP2.

CNP2 is produced by alternate splicing from the original CNP gene. In central and peripheral nervous system tissues, the enzyme is localized almost exclusively in the two cell types that elaborate myelin, the oligodendrocyte and the Schwann cell, respectively. Nonneural sources of CNPase have also been described, but they all have much lower activities than those found in brain. The freshly isolated brain enzymes appear as closely spaced doublets at approximately 46 and 48 kDa on SDS-PAGE. The primary sequence appears highly conserved between these two proteins, designated CNP1 and CNP2.

HALO22

HALO23 corresponds to NGFI-B [U17254], which is also known as Nur77. Its expression is increased 2.4 fold in haloperidol-treated rats.

NGFI-B was identified by differential hybridization as a gene that is rapidly, but transiently, induced in PC12 cells by NGF. The nucleotide sequence of the NGFI-B gene reveals that it encodes a 61 kd protein with strong homologies to members of the glucocorticoid nuclear receptor gene family. Transcription of NGFI-B itself is induced in an immediate early response and has been documented as a response to various stimuli including fos/jun and TSH.

HALO23

HALO23 corresponds to neurogranin [L09119]. Its expression is increased 1.1 fold in haloperidol-treated rats.

Neurogranin is also known as the C kinase substrate calmodulin binding protein and the rodent cortex protein (RC3), which is 78 amino acids in length. The RC3 protein amino terminus contains a cysteine-rich domain similar to those found in snake venom neurotoxins. The carboxyl terminus contains a collagen-like motif that may function in the assembly of RC3 subunits into a multimeric protein. RC3 and GAP-43 regulate calmodulin availability in dendritic spines and axons, respectively, and calmodulin regulates their ability to amplify the mobilization of Ca2+ in response to metabotropic glutamate receptor stimulation. These molecules release CaM rapidly in response to large influxes of Ca2+ and slowly in response to small increases. This nonlinear response is analogous to the behavior of a capacitor, hence the name calpacitin. The protein may be involved in the process of neuronal long-term potentiation and dendritic spine remodelling.

HALO24

HALO24 corresponds to V-1 protein. Its expression is decreased 2.0-fold in haldoperidol-treated rats. It contains 2.5 contiguous repeats of the cdc10/SWI6 motif, which was originally found in products of cell cycle control. Highest levels of expression of this gene are in the hippocampus and cerebellum, followed by cortical expression. The protein has been implicated in differentiating classes of neurons, including cerebellar granule cells. Abnormal temporal profile of V-1 expression during prenatal cerebellar development has been noted in the staggerer mouse mutant, which fails to establish connections between granule and purkinje cells in the cerebellum.

HALO25

HALO25 corresponds to the 190 kDA ankyrin isoform [FO69525]. Its expression is decreased 2.0-fold in haloperidol-treated rats.

Ankyrins are a family of adapters that mediate linkages between integral membrane proteins and cytoskeletal components. Such interactions are thought to be important to the polarized distribution of membrane proteins in transporting epithelia. This ankyrin isoform has homology to, but is not identical with, the previously identified larger neuronal isoform. The protein has (a) expression at the lateral plasma membrane, (b) functional assembly with the cytoskeleton, and (c) interaction with at least one membrane protein, the Na, K-ATPase. This latter interaction may support its involvement with the regulation of cell polarity.

HALO26

HALO26 corresponds to cathepsin S [LO3201]. Its expression is decreased 1.7-fold in haloperidol treated rats.

Cathepsin S is a cysteine protease with elastase activity. It was initially described in alveolar macrophages and has a broad range of natural pH activity. The gene contains only 2 Spl sites but contains 18 API sites that may be involved in the regulation of the gene.

HALO27

HALO27 corresponds to D-amino acid oxidase [B003400]. Its expression is decreased 2.0-fold in haldoperidol-treated rats.

D-amino acid oxidase is one of the principal and characteristic flavoenzymes of peroxisomes, and is found in liver, kidney and brain. The oxidase on a wide range of D-amino acids but is completely inactive on the natural, useful L-amino acids. It requires FAD as a prosthetic group. Its active site is distinct from D-aspartate oxidase. It is thoughthought that the function of the amino acid is for protection against D amino acids of bacteria, fungi. Alternatively, it is possible that the enzyme is may be an evolutionary relic. Prototypical reaction describes glycine being converted to glycoxylate (HC=OCOOH) with the release of NH3 and the formation of peroxide from $O_2$ and $H_2O$.

HALO28

HALO28 corresponds to stomach nonmuscle Ca+2 ATPase [J04023]. Its expression is increased 2-fold in heloperiodol-treated rats.

Stomach nonmuscle Ca+2 ATPase is also known as sacroplasmic reticulum Ca+2 ATPase. The enzyme is a Ca+2 transporting ATPase of the aspartylphosphate class. This ATPase was characterized in rat stomach, brain and kidney tissue and has homology to the slow-twitch isoform of the Ca+2 ATPase. It is distinguishable in that it has a novel, different C-terminus. It localizedsto ER/SR region and regulates intracellular calcium stores. It possibly a rat homolog for human HK1 channel.

HALO29

HALO29 corresponds to long interspersed reptitive DNA sequence LINE3 [13100_5]. Its expression decreases 5-fold in haloperidol-treated rats.

HALO30

HALO30 corresponds to long interspersed reptitive DNA containing 7 open reading frames (ORF) [53581_2]. Its expression decreases 3.5-fold in haloperidol-treated rats.

HALO31

HALO31 corresponds to L1 to retrotransposon ml vi2-m38 [U87605]. Its expression decreases 5.5-fold in haldoperidol-treated rats.

HALO32

HALO32 corresponds to L1 retrotransposon ORF2 [U82119]. Its expression decreases 3.3fold in haloperidol-treated rats.

HALO33

HALO33 corresponds to NGF1-A [M18146], whose expression has previously been reported to be differentially regulated by haldoperidol. In the present studies, its expression increased 1.6-fold in haloperidol-treated rats.

NGF1-A is also known as EGR-1, krox-24, or zif268. It is an early growth response gene that displays fos-like kinetics following mitogenic stimulation. It includes three DNA-binding zinc fingers and functions as a transcription factor.

HALO34

HALO34 corresponds to JunB [X54686], whose expression has been previously reported to be differentially regulated by haldoperidol. In the present studies, its expression increased 4-fold in haldoperidol-treated rats.

JunB is a transcription factor that is a member of the serum response element family (SRE) as is NGFI-A and NGFI-B.

HALO35

HALO35 corresponds to synaptophysin [X06388], whose expression has previously been reported to be differentially regulated by haldoperidol. In the present studies, its expression varied out 1-fold in haldoperidol-treated rats.

Synaptophysin is an integral membrane protein of small synoptic vesicles in brain and endocrine cells. It is also detected in presynaptic vesicles. Complexes of six synaptophysin molecules in the synaptic vesicle membrane may be part of the fusion pore between the synaptic vesicle and the plasma membrane.

HALO36

HALO36 corresponds to phophatidyl-inositol-3-kinase. Inisotaol monophsphates are reported to decrease 4–6 weeks following administration of heloperiodol in deconoate dosing.

The HALOX nucleic acids and encoded polypeptides can be identified using the information provide above. In some embodiments, the HALOX nucleic acids and polypeptide correspond to nucleic acids or polypeptides which include the various sequences (referenced by SEQ ID NOs) disclosed for each HALOX polypeptide.

Screening for Psychotropic Drugs Lacking Significant Side Effects

In one aspect, the invention provides a method of identifying a psychotropic agent that does not induce a significant motor side effect. A used herein, a "significant motor side effect" is an unintended motor effect which materially impacts a subject's ability to enjoy or perform a life function. Examples of types of motor effects include, e.g., dystonias. Dystonic movements can include slow writhing movements that are transiently sustained. They can affect several distinct areas of the body, such as the limbs, lips, tongue and eyes. Motor side effects can also include tardive dyskinesias. Symptoms of tardive dyskinesia include, e.g., persistent movement disorders, repeated tongue protrusions and lip smacking.

The psychotropic agent can be identified by providing a cell population that includes cells capable of expressing one or more genes homologous to those listed in Table 1 as HALO 1–32. The sequences need not be identical to sequences including HALO1–32, as long as the sequence is sufficiently similar that specific hybridization can be detected. Preferably, the cell includes sequences that are identical, or nearly identical to those identifying the HALOX nucleic acids shown in Table 1.

The cell population exposed to, i.e., contacted with, the test psychotropic agent can be any number of cells, i.e., one or more cells, and can be provided in vitro, in vivo, or ex vivo.

The cell population is preferably obtained from or derived from a human or rodent subject, or is provided in vivo in the mammalian subjected. The cell population can be, e.g., derived from brain tissue or non-brain neuronal tissue. Preferably, the cell population is from striatum brain tissue.

If desired, the cell population can be divided into two or more subpopulations. In some embodiments, various sub populations can be exposed to a control agent, and/or a test psychotropic agent, multiple test psychotropic agents, or, e.g., varying dosages of one or multiple test agents administered together, or in various combinations.

In general expression of the genes or nucleic acids can be measured using any method known in the art, e.g., using northern based hybridization analysis or methods which specifically, and, preferably, quantitatively amplify specific nucleic acid sequences.

Expression of sequences in test and control populations of cells can be compared using any art-recognized method for comprising expression of nucleic acid sequences. For example, expression can be compared using GENECALLING® methods as described in U.S. Pat. No. 5,871,697 and in Shimkets et al., Nat. Biotechnol. 17:798–803.

Expression of the gene or genes in the test cell population is then compared to the expression of the gene in a reference cell population, which is a cell population not exposed to the test psychotropic agent, or, in some embodiments, a cell population exposed to a significantly lower dose (e.g., 10,100,1000 or more lower dose) of the test psychotropic agent. Comparison can be performed on test and control samples measured concurrently or at temporally distinct times. An example of the latter is the use of compiled expression information, e.g., a sequence database, which assembles information about expression levels of known sequences following administration of various agents. For example, alteration of expression levels following administration of test psychotropic agent can be compared to the expression changes observed in the gene following administration of a control agent, such as haloperidol.

An alteration in expression of the gene in the test cell population compared to the expression of the gene in the reference cell population indicates the psychotropic agent does not induce a significant motor side effect. Preferably, the reference cell population, which can be one more cells, has been exposed to a psychotropic agent which induces a motor side effect. For example, the control agent can be a butyrophenone compound, such as droperidol or haloperidol, or can be control agent is a phenothiazine, such as chloropromaine. In some embodiments, the control agent can be a test vehicle.

For some applications it will be desirable to divide a starting cell population into two or more subpopulations of cells. The subpopulations can be created by dividing the first population of cells to create as identical a subpopulation as possible. This will be suitable, in, for example, in vitro or ex vivo screening methods. Alternatively, subpopulations can be created by exposing two matched populations of cells to the test psychotropic agent and control agent. For in vivo studies, for example, the test psychotropic agent and control agent can be administered to two groups of test animals, after which cells are recovered from animals and gene expression measured. Preferably, the test animals are as similar as possible with respect to genetic background, sex, age, weight, nutritional status and other parameters.

While the expression of any number of sequences shown in Table 1 can be compared, it is preferred that the expression of multiple, e.g., 2, 3, 5, 7, 9, 11, 13, 15, 17, 20, 23, 25, 30 or even all 32 sequences be compared. In addition, expression of one or more of sequences SEQ ID NOs;1–32 can be compared with sequences from of HALO33–36, corresponding to NGF1-A, JunB, synaptophysin, phosphatidyl-inositl-3-kinase, which have been previously shown to be response to haloperidol.

For some genes whose expression is measured, an increase in expression of the gene in the first subset of cells compared to the second subset of cells indicates the psychotropic agent does not induce a motor side effect. These genes include those sequences whose expression decreases in haloperidol cells vs. control cells, as shown in Table 1. Examples of such genes include, e.g., HALO 1–8, 10, 11, 14, 16–18, 21, 24–27, 29–32, and HALO33.

For other genes, a decrease in expression of the gene in the first subset of cells compared to the second subset of cells indicates psychotropic agent does not induce a motor side effect. These genes include those sequences whose expression increases in haloperidol cells vs. control cells, as shown in Table 1. Examples of these genes include, e.g., HALO 10, 13, 14, 20, 21, 23, 24, 29, and 35.

The invention also includes a psychotropic agent identified according to this screening method, and a pharmaceutical composition comprising the psychotropic agent so identified.

Also included in the invention is a method of selecting a psychotropic agent appropriate for a particular subject, e.g., a particular human subject. By appropriate is meant that psychotropic agent does not induce a significant motor defect in the subject.

The method is based in part on the observation that different individuals metabolize pharmaceutical agents due to, in part, differences in their genetic backgrounds. Accordingly, the method identifies agents which, for the given individual, do not induce gene expression patterns characteristic of a haloperidol response.

The method includes providing from the subject a cell population comprising a cell capable of expressing one or more genes, wherein the gene is selected from the group consisting of HALO 1–32. A cell population from the subject is then contacted with the psychotropic agent, and expression of the gene is measured and compared to a reference cell population. An alteration in expression of the gene in the test cell population compared to the expression of the gene in the reference cell population indicates the psychotropic agent is appropriate for the subject.

Any cell can be used, as long as it is capable of expressing one or more genes homologous to those listed in Table 1 as HALO 1–32. The sequences need not be identical to sequences including HALO-1–32, as long as the sequence is sufficiently similar that specific hybridization can be detected. Preferably, the cell includes sequences that are identical, or nearly identical to those identifying the HALOX nucleic acids shown in Table 1.

The cell population exposed to, i.e., contacted with, the test psychotropic agent can be any number of cells, i.e., one or more cells, and can be provided in vitro, in vivo, or ex vivo. The cell population is preferably derived from brain tissue or non-brain neuronal tissue. A preferred source for the cell population is striatum brain tissue.

If desired, the cell population can be divided into two or more subpopulations. In some embodiments, various sub populations can be exposed to a control agent, and/or a test psychotropic agent, multiple test psychotropic agents, or, e.g., varying dosages of one or multiple test agents administered together, or in various combinations.

In general expression of the genes or nucleic acids can be measured using any method known in the art, e.g., using northern based hybridization analysis or methods which specifically, and, preferably, quantitatively amplify specific nucleic acid sequences. In some embodiments expression can be measured at the protein level, i.e., by measuring expression levels of the HALOX proteins.

Expression of sequences in test and control populations of cells can be compared using any art-recognized method for comparing expression of nucleic acid sequences. For example, expression can be compared using GENECALL-ING® methods as described in U.S. Pat. No. 5,871,697 and in Shimkets et al., Nat. Biotechnol. 17:798–803.

Expression of the gene or genes in the test cell population is then compared to the expression of the gene in a reference cell population, which is a cell population not expressed to the test psychotropic agent, or, in some embodiments, a cell population exposed to a significantly lower dose (e.g., 10,100,1000 or more lower dose) of the test psychotropic agent. Comparison can be performed on test and control samples measured concurrently or at temporally distinct times. An example of the latter is the use of compiled expression information, e.g., a sequence database, which assembles information about expression levels of known sequences following administration of various agents. For example, alteration of expression levels following administration of test psychotropic agent can be compared to the expression changes observed in the gene following administration of a control agent, such as haloperidol.

An alteration in expression of the gene in the test cell population compared to the expression of the gene in the reference cell population indicates the psychotropic agent does not induce a significant motor side effect and is an appropriate agent for the subject. Preferably, the reference cell population, which can be one or more cells, has been exposed to a psychotropic agent which induces a motor side effect. For example, the control agent can be a butyrophenone compound, such as droperidol or haloperidol, or can be control agent is a phenothiazine, such as chloropromaine. In some embodiments, the control agent can be a test vehicle.

For some applications it will be desirable to divide a starting cell population into two or more subpopulations of cells. The subpopulations can be created by dividing the first population of cells to create as identical a subpopulation as possible. This will be suitable, in, for example, in vitro or ex vivo screening methods. Alternatively, subpopulations can be created by exposing two matched populations of cells to the test psychotropic agent and control agent. For in vivo studies, for example, the test psychotropic agent and control agent can be administered to two groups of test animals, after which cells are recovered from animals and gene expression measured. Preferably, the test animals are as similar as possible with respect to genetic background, sex, age, weight, nutritional status and other parameters.

While the expression of any number of sequences shown in Table 1 can be compared, it is preferred that the expression of multiple, e.g., 2, 3, 5, 7, 9, 11, 13, 15, 17, 20, 23, 25, 30 or even all 32 sequences be compared. In addition, expression of one or more of sequences SEQ ID NOs;1–32 can be compared with sequences from of HALO33–36, corresponding to NGF1-A, JunB, synaptophysin, phosphatidyl-inositl-3-kinase, which have been previously shown to be response to haloperidol.

For some genes whose expression is measured, an increase in expression of the gene in the first subset of cells compared to the second subset of cells indicates the psychotropic agent does not induce a motor side effect. These genes include those sequences whose expression decreases in haloperidol cells vs. control cells, as shown in Table 1. Examples of such genes include, e.g., HALO 1–8, 10, 11, 14, 16–18, 21, 24–27, 29–32, and HALO33.

For other genes, a decrease in expression of the gene in the first subset of cells compared to the second subset of cells indicates psychotropic agent does not induce a motor side effect. These genes include those sequences whose expression increases in haloperidol cells vs. control cells, as shown in Table 1. Examples of these genes include, e.g., HALO 10, 13, 14, 20, 21, 23, 24, 29, and 35.

Methods of Diagnosing Motor Pathologies

Included in the invention is a method of diagnosing, or determining susceptibility to, a movement disorder in a subject, e.g., a human subject.

The method includes providing from the subject a cell population which includes one or more cells capable of expressing one or more HALO genes, e.g., HALO1–36 wherein each gene is selected from the group consisting of HALO 1–32. Expression of the gene is compared to an expression pattern of cells that are indicative of the presence of a movement disorder ("diseased reference group"), or indicative of cells known not to suffer from a movement disorder ("healthy reference group"), or both reference groups. A similar expression level of the gene in the test cell population compared to the expression of the gene in the diseased cell population indicates subject has or is susceptible to a movement disorder. An inverse expression level of the gene in the test cell population compared to the expression of the gene in the healthy reference group similarly indicates the subject has or is susceptible to a movement disorder.

In a specific aspect, the invention includes a method of diagnosing or determining susceptibility to a movement disorder in a subject by providing a cell population from the subject that includes a cell capable of expression one or more genes, wherein each gene is selected from the group consisting of a quaking gene and a gene encoding VI protein and comparing the expression of the gene to the expression of the gene in a reference cell population. The gene can be e.g., a human or mouse quaking gene, e.g., a human Qk5 or Qk7 gene.

In some embodiments, the observed alteration in expression is an increase in expression of the quaking gene or VI gene in the test subject relative to a healthy reference group control sample. In other embodiments, the observed alteration in expression is an decrease in expression of the quaking gene or VI gene in the test subject relative to a healthy reference group control sample.

Methods of Treating motor pathologies

Also included in the invention is a method of preventing or delaying the onset of a motor pathology in a subject, e.g., a human, by administering to the subject an agent which increases the expression or activity of a gene selected from the group consisting of HALO 1–8, 10, 11, 14, 16–18, 21, 24–27, 29–32, and HALO33. In some embodiments, the motor pathology is associated with administration of a psychoactive agent to the subject.

In another aspect, the invention includes a method of preventing or delaying the onset of a motor pathology in a subject by administering to the subject an agent which decreases the expression or activity of a gene selected from the group consisting of HALO 9, 12, 13, 19, 20, 22, 23, 28, and HALO 34.

In some embodiments, the agent increases the expression or activity of a human quaking gene, and can be, e.g., a human Qk5 nucleic acid or protein, or a human Qk7 nucleic acid or protein.

In some embodiments, the motor pathology is associated with administration of a psychoactive agent to the subject. The motor pathology can be any of the motor impairments described herein, e.g., a dystonia.

In some embodiments, the agent increases the expression or activity of a human quaking gene. Thus, the agent can be e.g., a quaking gene, including a human Qk5 nucleic acid or human Qk7 nucleic acid, a human Qk5 or human Qk7 polypeptide, or an agonist of a human Qk5 or Qk7 polypeptide.

The herein described HALO nucleic acids, polypeptides, antibodies, agonists, and antagonists when used therapeutically are referred to herein as "Therapeutics". Methods of administration of Therapeutics include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestional mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. In a specific embodiment, administration may be by direct injection at the site (or former site) of a malignant tumor or neoplastic or pre-neoplastic tissue.

Various delivery systems are known and can be used to administer a Therapeutic of the present invention including, e.g., (i) encapsulation in liposomes, microparticles, microcapsules; (ii) recombinant cells capable of expressing the Therapeutic; (iii) receptor-mediated endocytosis (See, e.g., Wu and Wu, 1987, *J. Biol Chem* 262:4429–4432); (iv) construction of a Therapeutic nucleic acid as part of a retroviral or other vector, and the like. In one embodiment of the present invention, the Therapeutic may be delivered in a vesicle, in particular a liposome. In a liposome, the protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formlation include, without limitation, monoglycerides, diglycerides, sulfatides, lysolecithin, phospholipids, saponin, bile acids, and the like. Preparation of such liposomal formulations is within the level of skill in art, as disclosed, for example, in U.S. Pat. No. 4,837,028; and U.S. Pat. No. 4,737,323, all of which are incorporated herein by reference. In yet another embodiment, the Therapeutic can be delivered in a controlled release system including, e.g.: a delivery pump (See, e.g., Saudek, et al., 1989, *New Engl J Med* 321:574 and a semi-permeable polymeric material (See, e.g., Howard, et al., 1989. *J Neurosurg* 71:105). Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Bocca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intravellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. *Proc Natl Acad Sci USA* 88:1864–1868), and the like. Alternatively, a nucleic acid Therapeutic can be introduced intracellularly and incorporated within host cell DNA for expression, by homologous recombination.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formation will also depend on the route of administration, and the overall seriousness of the disease or disorder, and should be decided according to the judgment of the practitioner and each patient's circumstances. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. However, suitable dosage ranges for intravenous administration of the Therapeutics of the present invention are generally about 20–500 micrograms ($\Box$g) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The duration of intravenous therapy using the pharmaceutical composition of the present invention will vary, depending on the severity of the disease being treated and the condition and potential idosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Polynucleotides of the present invention can also be used for gene therapy. Gene therapy refers to therapy that is performed by the administration of a specific nucleic acid to a subject. Delivery of the Therapeutic nucleic acid into a mammalian subject may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. Polynucleotides of the invention may also be administered by other known methods for introducing of nucleic acid into a cell or organism (including, without limitation, in the form of viral vectors or naked DNA). Any of the methodologies relating to gene therapy available within the art may be used in the practice of the present invention. See e.g., Goldspiel, et al., 1993. *Clin Pharm* 12:488–505.

Cells may also be cultured ex vivo in the presence of therapeutic agents or proteins of the present invention in order to proliferate or to produce a desired effect on or activity in such cells Treated cells can then be introduced in vivo for therapeutic purposes.

HALO Nucleic Acids

Also provided in the invention are novel nucleic acid comprising a nucleic acid sequence selected from the group consisting of HALOs:1–19, or its complement, as well as vectors and cells including these nucleic acids.

Thus, one aspect of the invention pertains to isolated HALO nucleic acid molecules that encode HALO proteins or biologically active portions thereof. Also included are nucleic acid fragments sufficient for use as hybridization probes to identify HALO-encoding nucleic acid (e.g., HALO mRNA) and fragments for use as polymerase chain reaction (PCR) primers for the amplification or mutation of HALO nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt) or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid derived. For example, in various embodiments, the isolated HALO nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of any of HALOS:1–19, or a complement of any of these nucleotide sequences, can be isolated using standard molecular biology techniques and the sequence information provided herein. Using all or a portion of these nucleic acid sequences as a hybridization probe, HALO nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to HALO nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having at least about 10 nt and as many as 50 nt, preferably about 15 nt to 30 nt. They may be chemically synthesized and may be used as probes.

In another embodiment, an isolated nucleic acid molecule of the invention comprises a nucleic acid molecule that is a complement of the nucleotide sequence shown in HALO1–20. In another embodiment, an isolated nucleic acid molecule of the invention comprises a nucleic acid molecule that is a complement of the nucleotide sequence shown in any of these sequences, or a portion of any of these nucleotide sequences. A nucleic acid molecule that is complementary to the nucleotide sequence shown in HALO1–20 is one that is sufficiently complementary to the nucleotide sequence shown, such that it can hydrogen bond with little or no mismatches to the nucleotide sequences shown, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of HALOs1–19 or 20, e.g., a fragment that can be used as a probe or primer or a fragment encoding a biologically active portion of HALO. Fragments provided herein are defined as sequences of at least 6 (contiguous) nucleic acids or at least 4 (contiguous) amino acids, a length sufficient to allow for specific hybridization in the case of nucleic acid or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 45%, 50%, 70%, 80%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley &

Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which in incorporated herein by reference in its entirety).

A "homologous nucleic acid sequence" or "homologous amino acid sequence," or variations thereof, refer to sequence characterized by a homology at the nucleotide level or amino acid level as discussed above. Homologous nucleotide sequences encode those sequences coding for isoforms of a HALO polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a HALO polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding a human HALO protein. Homologous nucleic acid sequence include those nucleic acid sequences the encode conservative amino acid substitutions (see below) in a HALO polypeptide, as well as a polypeptide having a HALO activity. A homologous amino acid sequences does not encode the amino acid sequence of a human HALO polypeptide.

The nucleotide sequence determined from the cloning of human HALO genes allows for the generation of probes and primers designed for use in identifying and/or cloning HALO homologous in other cell types, e.g., from other tissues, as well as HALO homologous from other mammals. The probe/primer typically comprises a substantially purified oligonucleotide. The oligonucleotide typically comprises a region of a nucleotide sequence that hybridizes under stringent conditions to at least about 12, 25, 50, 100, 150, 200, 250, 300, 350, or 400 consecutive sense strand nucleotide sequence of nucleic acid comprising a HALO sequence, or an anti-sense strand nucleotide sequence of a nucleic acid comprising a HALO sequence, or of a naturally occurring mutant of these sequences.

Probes based on human HALO nucleotide sequences can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a HALO protein, such as by measuring a level of a HALO-encoding nucleic acid in a sample of cells from a subject e.g., detecting HALO mRNA levels or determining whether a genomic HALO gene has been mutated or deleted.

"A polypeptide having a biologically active portion of HALO" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of HALO" can be prepared by isolating a portion of HALO1, 3, 5, 7, 9, 11, 13, 15, 17, 19, 21, 23, 25, 27, 29, 31, 33, 35, 37, 39, 41, 43, 45, or 47, that encodes a polypeptide having a HALO biological activity, expressing the encoded portion of HALO protein (e.g., by recombinant expression in vitro) and assessing the activity of the encoded portion of HALO. For example, a nucleic acid fragment encoding a biologically active portion of a HALO polypeptide can optionally include an ATP-binding domain. In another embodiment, a nucleic acid fragment encoding a biologically active portion of HALO includes one or more regions.

HALO variants

The invention further encompasses nucleic acid molecules that differ from the disclosed or referenced HALO nucleotide sequences due to degeneracy of the genetic code. These nucleic acids thus encode the same HALO protein as that encoded by nucleotide sequence comprising a HALO nucleic acid as shown in, e.g., HALO1–19 OR 20.

In addition to the human HALO nucleotide sequence shown in HALO1, 3, 5, 7, 9, 11, 13, 15, 17, 19, 21, 23, 25, 27, 29, 31, 33, 35, 37, 39, 41, 43, 45, or 47, it will be appreciated by those skilled in the art that DNA sequence polymorphisms that lead to changes in the amino acid sequences of a HALO polypeptide may exist within a population (e.g., the human population). Such genetic polymorphism in the HALO gene may exist among individuals within a population due to natural allelic variation. As used herein, the terms "gene" and "recombinant gene" refer to nucleic acid molecules comprising an open reading frame encoding a HALO protein, preferably a mammalian HALO protein. Such natural allelic variations can typically result in 1–5% variance in the nucleotide sequence of the HALO gene. Any and all such nucleotide variations and resulting amino acid polymorphisms in HALO that are the result of natural allelic variation and that do not alter the functional activity of HALO are intended to be within the scope of the invention.

Moreover, nucleic acid molecules encoding HALO proteins from other species, and thus that have nucleotide sequence that differs from the human sequence of HALO1–20, are intended to be within the cope of the invention. Nucleic acid molecules corresponding to natural allelic variants and homologous of the HALO DNAs of the invention can be isolated based on their homology to the human HALO nucleic acids disclosed herein using the human cDNAs, or a portion thereof, as a hybridization probe according to standard hybridization techniques under stringent hybridization conditions. For example, a soluble human HALODNA can be isolated based on its homology to human membrane-bound HALO. Likewise, a membrane-bound human HALODNA can be isolated based on its homology to soluble human HALO.

Accordingly, in another embodiment, an isolated nucleic acid molecule of the invention is at least 6 nucleotides in length and hybridizes under stringent conditions to the nucleic acid molecule comprising the nucleotide sequence of HALOS:1–19, or 20. In another embodiment, the nucleic acid is at least 10, 25, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding HALO proteins derived from species other than human) or other related sequences (e.g., paralogs) can be obtained by low, moderate or high stringency hybridization with all or a portion of the particular human sequence as a probe using methods as well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides |(e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70% 75%, 85%, 90%, 95%, 98%, or 99% homologous to each other typically remain hybridized to each other. A non-limiting example of stringent hybridization conditions is hybridization in a high salt buffer comprising 6× SSC, 50 mM Tris-HCl (pH 7.5), mM EDTA, 0.02% PVP, 0.02% Ficoll, 0.02% BSA, and 500 mg/ml denatured salmon sperm DNA at 65° C. This hybridization is followed by one or more washes in 0.2× SSC, 0.01% BSA at 50° C. An isolated nucleic acid molecule of the invention that hybridizes under stringent conditions to the sequence of HALOS:1–19 or 20 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of HALOS:1–19 or 20, or fragments, analogs or derivatives thereof, under conditions of moderate stringency is provided. A non-limiting example of moderate stringency hybridization conditions are hybridization in 6× SSC, 5× Denhardt's solution, 0.5% SDS and 100 mg/ml denatured salmon sperm DNA at 55° C., followed by one or more washes in 1× SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Krieger, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of HALOS:1–19 or 20, or fragments, analogs or derivatives thereof, under conditions of low stringency, is provided. A non-limiting example of low stringency hybridization conditions are hybridization in 35% formamide, 5× SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2× SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo et al., 1981, *Proc Natl Acad Sci USA* 78: 6789–6792.

Conservative Mutations

In addition to naturally-occurring allelic variants of the HALO sequence that may exist in the population, the skilled artisan will further appreciate the changes can be introduced into a HALO nucleic acid or directly into a HALO polypeptide sequence without altering the functional ability of the HALO protein. In some embodiments, the nucleotide sequence of HALOS:1–19 or 30 will be altered, thereby leading to changes in the amino acid sequence of the encoded HALO protein. For example, nucleotide substitutions that result in amino acid substitutions at various "non-essential" amino acid residues can be made in the sequence of HALOS:1–19 or 20. A "non-essential" amino acid residues that can be altered from the wild-type sequence of HALO without altering the biological activity, whereas an "essential" amino acid residue is required for biological activity. For example, amino acid residues that are conserved among the HALO proteins of the present invention, are predicted to be particularly unamendable to alteration.

In addition, amino acid residues that are conserved among family members of the HALO proteins of the present invention, are also predicted to be particularly unamendable to alteration. As such, these conserved domains are not likely to be amenable to mutation. Other amino acid residues, however, (e.g., those that are not conserved or only semi-conserved among members of the HALO proteins) may not be essential for activity and thus are likely to be amenable to alteration.

Another aspect of the invention pertains to nucleic acid molecules encoding HALO proteins that contain changes in amino acid residues that are not essential for activity. Such HALO proteins differ in amino acid sequence from the amino acid sequences of polypeptides encoded by nucleic acids containing HALOS:1–19 or 20, yet retain biological activity. In one embodiment, the isolated nucleic acid molecule comprises a nucleotide sequence encoding a protein, wherein the protein comprises an amino acid sequence at least about 45% homologous, more preferably 60%, and still more preferably at least about 70%, 80%, 90%, 95%, 98%, and most preferably at least about 99% homologous to the amino acid sequence of the amino acid sequences of polypeptides encoded by nucleic acids comprising HALOS:1–19 or 20.

An isolated nucleic acid molecule encoding a HALO protein homologous to can be created by introducing one or more nucleotide substitutions, additions or deletions into the nucleotide sequence of a nucleic acid comprising HALOS1–19 or 20, such that one or more amino acid substitutions, additions or deletions are introduced into the encoded protein.

Mutations can be introduced into a nucleic acid comprising HALOS:1–19 or 20 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic such side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in HALO is replaced with another amino acid residue from the same side chain family. Alternatively, in another embodiment, mutations can be introduced randomly along all or part of a HALO coding sequence, such as by saturation mutagenesis, and the resultant mutants can be screened for HALO biological activity to identify mutants that retain activity. Following mutagenesis of the nucleic acid, the encoded protein can be expressed by any recombinant technology known in the art and the activity of the protein can be determined.

In one embodiment, a mutant HALO protein can be assayed for (1) the ability to form protein:protein interactions with other HALO proteins, other cell-surface proteins, or biologically active portions thereof, (2) complex formation between a mutant HALO protein and a HALO ligand; (3) the ability of mutant HALO protein to bind to an intracellular target protein or biologically active portion thereof; (e.g., avidin proteins); (4) the ability to bind ATP; or (5) the ability to specifically bind a HALO protein antibody.

In specific embodiments, the invention includes an isolated polynucleotide comprising a sequence chosen from the group consisting of a first sequence, the first sequence being 80% or more identical to a second sequence that encodes a polypeptide whose expression is modulated in a mammal to which haloperidol is administered; a fragment of the first sequence; a complementary polynucleotide sequence comprising a sequence complementary to the first sequence; and a fragment of the complementary polynucleotide sequence.

Preferably, the second sequence is chosen from the group consisting of a polynucleotide encoding splice variant 5 of a human ortholog of murine quaking type I, a polynucleotide encoding splice variant 7 of a human ortholog of murine quaking type I, a sequence having at least 88% identity to the human KIAA0383 gene, a rat polynucleotide having at least 83% identity to a mouse polynucleotide encoding an EGF repeat transmembrane protein, a sequence having at least 80% identity to a polynucleotide encoding human suilisol, a sequence having at least 72% identity to rat repetitive ribosomal DNA II 3' to 45S pre-rRNA, a sequence encoding a polypeptide having at least 70% amino acid identity to E. coli putative ATP-dependent RNA helicase RHLB, a sequence having at least 65% identity to a 5' region of human NOF1, a sequence having at least 91% identity to a polynucleotide encoding mouse phosphatidylinositol-3-kinase 110 kD subunit, a sequence having at least 98% identity to a polynucleotide encoding mouse meis2 subfamily protein, and a sequence having at least 89% identity a polynucleotide encoding a human rab5c-like protein, a polynucleotide encoding a polypeptide having at least 80% amino acid identity to human predicted protein DJ257A7.1, a polynucleotide similar to rat repetitive ribosomal DNA II 3' to 45S pre-rRNA, fragment r0w0__85.8, fragment r0j0__120.6, fragment 10y0 158.5, fragment y0p0__314.6, fragment m1s0__321.4, and fragment gln0__114.5.

In other embodiment, the second sequence is chosen from the group consisting of a polynucleotide encoding splice variant 5 of a human ortholog of murine quaking type I, a polynucleotide encoding splice variant 7 of a human ortholog of murine quaking type I, a sequence having at least 88% identity to the human KIAA0383 gene, a rat polynucleotide having at least 83% identity to a mouse polynucleotide encoding and EGF repeat transmembrane protein, a sequence having at least 80% identity to a polynucleotide encoding human suilisol, a sequence having at least 72% identity to rat repetitive ribosomal DNA II 3' to 45S pre-rRNA, a sequence encoding a polypeptide having at least 70% amino acid identity to E. coli putative ATP-dependent RNA helicase RHLB, and a sequence having at least 65% identity to a 5' region of human NOF1.

In yet other embodiments, the second sequence is chosen from the group consisting of a polynucleotide encoding splice variant 5 of a human ortholog of murine quaking type I and a polynucleotide encoding splice variant 7 of a human ortholog of murine quaking type I.

Preferably, the fragment hybridizes to the sequence complementary to the first sequence.

In other embodiment, the fragment of the complementary polynucleotide sequence described in claim 1 wherein the fragment of the complementary polynucleotide sequence hybridizes to the first sequence.

In other specific embodiments, the nucleic acid is RNA or DNA. The fragment or the fragment of the complementary polynucleotide sequence described in claim 1, wherein the fragment is between about 10 and about 100 nucleotides in length, e.g., between about 10 and about 90 nucleotides in length, or about 10 and about 75 nucleotides in length, about 10 and about 50 bases in length, about 10 and about 40 bases in length, or about 15 and about 30 bases in length.

In specific embodiments, the invention includes an isolated polynucleotide comprising a sequence that encodes a polypeptide chosen from the group consisting of splice variant 5 of a human ortholog of murine quaking type I and splice variant 7 of a human ortholog of murine quaking type I.

Antisense

Another aspect of the invention pertains to isolated antisense nucleic acid molecules that are hybridizable to or complementary to the nucleic acid molecule comprising the nucleotide sequence of a HALO sequence or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire HALO coding strand, or to only a portion thereof. Nucleic acid molecules encoding fragments, homologs, derivatives and analogs of a HALO protein, or antisense nucleic acids complementary to a nucleic acid comprising a HALO nucleic acid sequence are additionally provided.

In one embodiment, an antisense nucleic acid molecule is antisense to a "coding region" of the coding strand of a nucleotide sequence encoding HALO. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding HALO. The term "noncoding region" refers to 5' and 3' sequences which flank the coding region that are not translated into amino acids (i.e., also referred to as 5' and 3' untranslated regions).

Given the coding strand sequences encoding HALO disclosed herein, antisense nucleic acids of the invention can be designed according to the rules of Watson and Crick or Hoogsteen base pairing. The antisense nucleic acid molecule can be complementary to the entire coding region of HALO mRNA, but more preferably is an oligonucleotide that is antisense to only a portion of the coding or noncoding region of HALO mRNA. For example, the antisense oligonucleotide can be complementary to the region surrounding the translation start site of HALO mRNA. An antisense oligonucleotide can be, for example, about 5, 10, 15, 20, 25, 30, 35, 40, 45, or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a HALO protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systematically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res*. 15: 6131–6148) or a chimeric RNA-DNA analogue (Inoue et al. (1987) *FEBS Lett* 215: 327–330).

Ribozymes and PNA moieties

In still another embodiment, an antisense nucleic acid of the invention is a ribozyme.

Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave HALO mRNA transcripts to thereby inhibit translation of HALO mRNA. A ribozyme having specificity for a HALO-encoding nucleic acid can be designated based upon the nucleotide sequence of a HALO DNA disclosed herein. For example, a derivative of a Tetrahymena L-19 IVS RNA can be constructed in which the nucleotide sequence of the active site is complementary to the nucleotide sequence to be cleaved in a HALO-encoding mRNA. See, e.g., Cech et al. U.S. Pat. No. 4,987,071; and Cech et al. U.S. Pat. No. 5,116,742. Alternatively, HALO mRNA can be used to select a catalytic RNA having a specific ribonuclease activity from a pool of RNA molecules. See, e.g., Bartel et al., (1993) *Science* 261:1411–1418.

Alternatively, HALO gene expression can be inhibited by targeting nucleotide sequences complementary to the regulatory region of a HALO nucleic acid (e.g., the HALO promoter and/or enhancers) to form triple helical structures that prevent transcription of the HALO gene in target cells. See generally, Helene. (1991) *Anticancer Drug Des.* 6: 569–84; Helene. et al. (1992) *Ann. N.Y. Acad. Sci.* 660:27–36; and Maher (1992) *Bioassays* 14: 807–15.

In various embodiment, the nucleic acids of HALO can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of HALO can be used in therapeutic and diagnostic applications. For example, PNAs can be used as antisense or antigene agents for sequence-specific modulation of gene expression by, e.g., inducing transcription or translation arrest or inhibiting replication. PNAs of HALO can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers of DNA sequence and hybridization (Hyrup et al. (1996), above, Perry-O'Keefe (1996), above).

In another embodiment, PNAs of HALO can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of HALO can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, Proc. *Natl. Acad. Sci.* 84:648–652; PCT Publication No. W088/09810) or the blood-brain barrier (see, e.g., PCT Publication No. W089/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

HALO polypeptides

One aspect of the invention pertains to isolated HALO proteins, and biologically active portions thereof, or derivatives, fragments, analogs or homologs thereof. Also provided are polypeptide fragments suitable for use as immunogens to raise anti-HALO antibodies. In one embodiment, native HALO proteins can be isolated from cells or tissue sources by an appropriate purification scheme using standard protein purification techniques. In another embodiment, HALO proteins are produced by recombinant DNA techniques. Alternative to recombinant expression, a HALO protein or polypeptide can be synthesized chemically using standard peptide synthesis techniques.

An "isolated" or "purified" protein or biologically active portion thereof is substantially free of cellular material or other contaminating proteins from the cell or tissue source from which the HALO protein is derived, or substantially free from chemical precursors or other chemicals when chemically synthesized. The language "substantially free of cellular material" includes preparations of HALO protein in which the protein is separated from cellular components of the cells from which it is isolated or recombinantly produced. In one embodiment, the language "substantially free of cellular material" includes preparations of HALO protein having less than about 30% (by dry weight) of non-HALO protein (also referred to herein as a "contaminating protein"), more preferably less than about 20% of non-HALO protein, still more preferably less than about 10% of non-HALO protein, and most preferably less than about 5% non-HALO protein. When the HALO protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of HALO protein in which the protein is separated from chemical precursors or other chemicals that are involved in the synthesis of the protein. In one embodiment, the language "substantially free of chemical precursors or other chemicals" includes preparations of HALO protein having less than about 30% (by dry weight) of chemical precursors or non-HALO chemicals, more preferably less than about 20% chemical precursors or non-HALO chemicals, still more preferably less than about 10% chemical precursors or non-HALO chemicals, and most preferably less than about 5% chemical precursors or non-HALO chemicals.

Biologically active portions of a HALO protein include peptides comprising amino acid sequences sufficiently homologous to or derived from the amino acid sequence of the HALO protein, e.g., the amino acid sequence encoded by a nucleic acid comprising HALO 1–20 that include fewer amino acids than the full length HALO proteins, and exhibit at least one activity of a HALO protein. Typically, biologically active portions comprise a domain or motif with at least one activity of the HALO protein. A biologically active portion of a HALO protein can be a polypeptide which is, for example, 10, 25, 50, 100 or more amino acids in length.

A biologically active portion of a HALO protein of the present invention may contain at least one of the above-identified domains conserved between the HALO proteins. An alternative biologically active portion of a HALO protein may contain at least two of the above-identified domains. Another biologically active portion of a HALO protein may contain at least three of the above-identified domains. Yet another biologically active portion of a HALO protein of the present invention may contain at least four of the above-identified domains.

Moreover, other biologically active portions, in which other regions of the protein are deleted, can be prepared by recombinant techniques and evaluated for one or more of the functional activities of a native HALO protein.

In some embodiments, the HALO protein is substantially homologous to one of these HALO proteins and retains its the functional activity, yet differs in amino acid sequence due to natural allelic variation of mutagenesis, as described in detail below.

In specific embodiments, the invention includes an isolated polypeptide comprising an amino acid sequence that is 80% or more identical to the sequence of a polypeptide whose expression is modulated in a mammal to which haloperiodol is administered.

For example, in some embodiments, the polypeptide is expressed by splice variant 5 of a human ortholog of murine quaking type I or the polypeptide expressed by splice variant 7 of a human ortholog of murine quaking type I.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See Needleman and Wunsch 1970 *J Mol Biol* 48: 443–453. Using GCP GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of a DNA sequence comprising HALOS:1–19 or 20.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides HALO chimeric or fusion proteins. As used herein, a HALO "chimeric protein" or "fusion protein" comprises a HALO polypeptide operatively linked to a non-HALO polypeptide. A "HALO polypeptide" refers to a polypeptide having an amino acid sequence corresponding to HALO, whereas a "non-HALO polypeptide" refers to a polypeptide having an amino acid sequence corresponding to a protein that is not substantially homologous to the HALO protein, e.g., a protein that is different from the HALO protein and that is derived from the same or a different organism. Within a HALO fusion protein the HALO polypeptide can correspond to all or a portion of a HALO protein. In one embodiment, a HALO fusion protein comprises at least one biologically active portion of a HALO protein. In another embodiment, a HALO fusion protein comprises at least two biologically active portions of a HALO protein. In yet another embodiment, a HALO fusion protein comprises at least three biologically active portions of a HALO protein. Within the fusion protein, the term "operatively linked" is intended to indicate that the HALO polypeptide and the non-HALO polypeptide are fused in-frame to each other. The non-HALO polypeptide can be fused to the N-terminus or C-terminus of the HALO polypeptide.

For example, in one embodiment a HALO fusion protein comprises a HALO domain operably linked to the extracellular domain of a second protein. Such fusion protein can be further utilized in screening assays for compounds which modulate HALO activity (such assays are described in detail below).

In yet another embodiment, the fusion protein is a GST-HALO fusion protein in which the HALO sequences are fused to the C-terminus of the GST (i.e., glutathione S-transferase) sequences. Such fusion proteins can facilitate the purification of recombinant HALO.

In another embodiment, the fusion protein is a HALO protein containing a heterologous signal sequence at its N-terminus. For example, a native HALO signal sequence can be removed and replaced with a signal sequence from another protein. In certain host cells (e.g., mammalian host cells), expression and/or secretion of HALO can be increased through use of a heterologous signal sequence.

In yet another embodiment, the fusion protein is a HALO-immunoglobulin fusion protein in which the HALO sequences comprising one or more domains are fused to sequences derived from a member of the immunoglobulin protein family. The HALO-immunoglobulin fusion proteins of the invention can be incorporated into pharmaceutical compositions and administered to a subject to inhibit an interaction between a HALO ligand and a HALO protein on the surface of a cell, to thereby suppress HALO-mediated signal transduction in vivo. The HALO-immunoglobulin fusion proteins can be used to affect the bioavailability of a HALO cognate ligand. Inhibition of the HALO ligand/HALO interaction may be useful therapeutically for both the treatment of proliferative and differentiative disorders, as well as modulating (e.g. promoting or inhibiting) cell survival. Moreover, the HALO-immunoglobulin fusion protein of the invention can be used as immunogens to produce anti-HALO antibodies in a subject, to purify HALO ligands, and in screening assays to identify molecules that inhibit the interaction of HALO with a HALO ligand.

A HALO chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion greater gene can be synthesized by conventional techniques including automated DNA synthesizers. Alternatively, PCR amplification of gene fragments can be carried out using anchor primers that give rise to complementary overhands between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A HALO-encoding nucleic acid can be cloned into such an expression vector such that the fusion moiety is linked in-frame to the HALO protein.

HALO Agonists and Antagonists

The present invention also pertains to variants of the HALO proteins that function as either HALO agonists (mimetics) or as HALO antagonists. Variants of the HALO protein can be generated by mutagenesis, e.g., discrete point mutation or truncation of the HALO protein. An agonist of the HALO protein can retain substantially the same, or a subset of, the biological activities of the naturally occurring form of the HALO protein. An antagonist of the HALO protein can inhibit one or more of the activities of the naturally occurring form of the HALO protein by, for example, competitively binding to a downstream or upstream member of a cellular signaling cascade which includes the HALO protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the HALO proteins.

Variants of the HALO protein that function as either HALO agonists (mimetics) or as HALO antagonists can be identified by screening combinatorial libraries of mutants, e.g., truncation mutants, of the HALO protein for HALO protein agonist or antagonist activity. In one embodiment, a variegated library of HALO variants is generated by combinatorial mutagenesis at the nucleic acid level and is encoded by a variegated gene library. A variegated library of HALO variants can be produced by, for example, enzymatically ligating a mixture of synthetic oligonucleotides into gene sequences such that a degenerate set of potential HALO sequences is expressible as individual polypeptides, or alternatively, as a set of larger fusion proteins (e.g., for phage display) containing the set of HALO sequences therein. There are a variety of methods which can be used to produce libraries of potential HALO variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential HALO sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the HALO protein coding sequence can be used to generate a variegated population of HALO fragments for screening and subsequent selection of variants of a HALO protein. In one embodiment, a library of coding sequence fragments can be generated by treating a double stranded PCR fragment of a HALO coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the HALO protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of HALO proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify HALO variants (Arkin and Yourvan (1992) PNAS 89:7811–7815; Delgrave et al. (1993) Protein Engineering 6:327–331).

Anti-HALO Antibodies

An isolated HALO protein, or a portion or fragment thereof, can be used as an immunogen to generate antibodies that bind HALO using standard techniques for polyclonal and monoclonal antibody preparation. The full-length HALO protein can be used or, alternatively, the invention provides antigenic peptide fragments of HALO for use as immunogens. The antigenic peptide of HALO comprises at least 8 amino acid residues of the amino acid sequence encoded by a nucleic acid comprising the nucleic acid sequence shown in HALOS:1–19 or 20 and encompasses an epitope of HALO such that an antibody raised against the peptide forms a specific immune complex with HALO. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of HALO that are located on the surface of the protein, e.g., hydrophilic regions.

HALO polypeptides or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen. Such antibodies include, but are not limited to, polyclonal, monoclonal, chimeric, single chain, $F_{ab}$ and $F_{(ab')2}$ fragments, and an $F_{ab}$ expression library. Various procedures known within the art may be used for the production of polyclonal or monoclonal antibodies to a HALO protein sequence, or derivatives, fragments, analogs or homologs thereof. Some of these proteins are discussed below.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed HALO protein or a chemically synthesized HALO polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmatte-Guerin and *Corynebacterium parvum*, or similar immunostimulatory agents. If desired, the antibody molecules directed against HALO can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of HALO. A monoclonal antibody composition thus typically displays a single binding affinity for a particular HALO protein with which it immuoreacts. For preparation of monoclonal antibodies directed towards a particular HALO protein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 Nature 256: 495–497); the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

According to the invention, techniques can be adapted for the production of single-chain antibodies specific to a HALO protein (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a HALO protein or derivatives, fragments, analogs or homologs thereof. Non-human antibodies can be "humanized" by techniques well known in the art. See e.g., U.S. Pat. No. 5,225,539. Antibody fragments that contain the idiotypes to a HALO protein may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-HALO antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041–1043; Liu et al. (1987) PNAS 84:3439–3443; Liu et al. (1987) J Immunol. 139:3521–3526; Sun et al. (1987) PNAS 84:214–218; Nishimura et al. (1987) Cancer Res 47:999–1005; Wood et al. (1985) Nature 214:446–449; Shaw et al. (1988) J Natl Cancer Inst. 80:1553–1559); Morrison (1985) Science 229:1202–1207; Oi et al. (1986) BioTechniques 4:214; U.S. Pat. No. 5,225,539; Jones et al. (1986) Nature 321:552–525; Verhoeyan et al. (1988) Science 239:1534; and Beidler et al. (1988) J Immunol 141:4053–4060.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a HALO protein is facilitated by generation of hybridomas that bind to the fragment of a HALO protein possessing such a domain. Antibodies that are specific for one or more domains within a HALO protein, e.g., domains spanning the above-identified conserved regions of HALO family proteins, or derivatives, fragments, analogs or homologs thereof, are also provided herein.

Anti-HALO antibodies may be used in methods known within the art relating to the localization and/or quantitation of a HALO protein (e.g., for use in measuring levels of the HALO protein within appropriate physiological samples, for use in diagnostic methods, for use in imaging the protein, and the like). In a given embodiment, antibodies for HALO proteins, or derivatives, fragments, analogs or homologs thereof, that contain the antibody derived binding domain, are utilized as pharmacologically-active compounds [hereinafter "Therapeutics"].

An anti-HALO antibody (e.g., monoclonal antibody) can be used to isolate HALO by standard techniques, such as affinity chromatography or immunoprecipitation. An anti-HALO antibody can facilitate the purification of natural HALO from cells and of recombinantly produced HALO expressed in host cells. Moreover, an anti-HALO antibody can be used to detect HALO protein (e.g., in a cellular lysate or cell supernatant) in order to evaluate the abundance an pattern of expression of the HALO protein. Anti-HALO antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

HALO Recombinant Expression Vectors and Host Cells

Another aspect of the invention pertains to vectors, preferably expression vectors, containing a nuclei acid encoding HALO protein, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used intechangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that isoperatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into hose cells to thereby produce proteins or peptides, including fusion proteins or peptides, encoded by nucleic acids as described herein (e.g., HALO proteins, mutant forms of HALO, fusion proteins, etc.).

The recombinant expression vectors of the invention can be designed for expression of HALO in prokaryotic or eukaryotic cells. For example, HALO can be expressed in bacterial cells such as *E. coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequence of the invention can be carried out by standard DNA synthesis techniques.

In another embodiment, the HALO expression vector is a yeast expression vector. Examples of vectors for expression in yeast *S. cerevisiae* include pYepSec1 (Baldari, et al., (1987) *EMBO J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (In Vitrogen Corp, San Diego, Calif.).

Alternatively, HALO can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (See (1987) *Nature* 329:840) and pMT2PC (Kaumfan et al. (1987) *EMBO J* 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

The invention further provides a recombinant expression vector comprising a DNA molecule of the invention cloned into the expression vector in an antisense orientation. That is, the DNA molecule is operatively linked to a regulatory sequence in manner that allows for expression (by transcription of the DNA molecule) of an RNA molecule that is antisense to HALO mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes are Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, HALO protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance or antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding HALO or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an HALO protein. Accordingly, the invention further provides methods for producing HALO protein using the host cells of the invention. In one embodiment, the method comprises culturing the host cell of invention (into which a recombinant expression vector encoding HALO has been introduced) in a suitable medium such that HALO protein is produced. In another embodiment, the method further comprises isolating HALO from the medium or the host cell.

Kits and Nucleic Acid Collections for Identifying Psychotropic Agents or Movement Disorders In another aspect, the invention provides a kit useful for examining a pathophysiology associated with a PPARα-mediated pathway. The kit can include nucleic acids that detect two or more HALO sequences. In preferred embodiments, the kit includes reagents which detect 3, 4, 5, 6, 8, 10, 12, 15, 20, 25, 30, 35, or all of the HALOX nucleic acid sequences.

The invention also includes an isolated plurality of sequences which can identify one or more HALOX responsive nucleic acid sequences.

The kit or plurality may include, e.g., sequence homologous to HALOX nucleic acid sequences, or sequences which can specifically identify one or more HALOX nucleic acid sequences.

Single Nucleotide Polymorphisms Associated with HALOX Genes

The invention also provides nucleic acid sequences nucleic acids containing polymorphisms associated with HALOX-responsive genes. The term "polymorphism" in this context refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transverse is the replacement of a purine by a pyrimidine or vice versa. Single nucleotide polymorphisms can also arise from a deletion of a nucleotide or an insertion of a nucleotide relative to a reference allele.

Hybridizations are usually performed under stringent conditions, for example, at a salt concentration of no more than 1M and a temperature of at least 25 degree. C. For example, conditions of 5× SSPE (750 mm NaCl, 50 mM NaPhosphate, 5 mM EDTA, pH 7.4) and a temperature of 25.degree.–30 degree. C. are suitable for allele-specific probe hybridizations.

An isolated nucleic acid means an object species invention) that is the predominant species present (i.e., on a molar basis it is more abundant that any other individual species in the composition). Preferably, an isolated nucleic acid comprises at least about 50, 80 or 90 percent (on a molar basis) of all macromolecular species present. Most preferably, the object species is purified to essential homogeneity (contaminant species cannot be detected in the composition by conventional detection methods).

Polymorphisms are detected in a target nucleic acid from an individual being analyzed. For assay of genomic DAN, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an origin in which the target nucleic acid is expressed. Many of the methods described below require amplification of DNA from target samples. This can be accomplished by e.g., PCR. See generally, PCR Technology: Principles and Applications for DNA Amplification (ed. H. A. Erlich, Freeman Press, N.Y., N.Y., 1992); PCR Protocols: A Guide to Methods and Applications (eds. Innis, et al., Academic Press, San Diego, Calif., 1990); Mattila et al., Nucleic Acids Res. 19, 4967 (1991); Ecker et al., PCR Methods and Applications 1, 17 (1991); PCR (eds. McPherson et al., IRL Press, Oxford); and U.S. Pat. No. 4,683,202 (each of which is incorporated by reference for all purposes).

Other suitable amplification methods include the ligase chain reaction (LCR), (See Wu, and Wallace, Genomics 4, 560 (1989), Landegren et al., Science 241, 1077 (1988)), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

There are two distinct types of analysis depending whether a polymorphism in question has already been characterized. The first type of analysis is sometimes referred to as de novo characterization. This analysis compares target sequences in different individuals to identify points of variation, i.e., polymorphic sites. By analyzing a groups of individuals representing the greatest ethnic of diversity among humans and greatest breed and species variety in plants and animals, patterns characteristic of the most common alleles/haplotypes of the locus can be identified, and the frequencies of such populations in the population determined. Additional allelic frequencies can be determined for subpopulations characterized by criteria such as geography, race, or gender. The second type of analysis is determining which form(s) of a characterized polymorphism are present in individuals under test.

OTHER EMBODIMENTS

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

SEQUENCE LISTING

<160> NUMBER OF SEQ ID NOS: 71

<210> SEQ ID NO 1
<211> LENGTH: 86
<212> TYPE: DNA
<213> ORGANISM: Rattus rattus

<400> SEQUENCE: 1
gaattcagcc agggatcgcc cgtgctcaat gacctcactg ccatcctgga cttggcttgc    60
ctagatctcc tgctccagtt gctagc    86

<210> SEQ ID NO 2
<211> LENGTH: 121
<212> TYPE: DNA
<213> ORGANISM: Rattus rattus

<400> SEQUENCE: 2

```
gaattcattg gaaagccaaa cgggtcattt gcagttaccc cctccaaccc accccacag      60 tcttaaagct gtgctcactg ggatagaaca caaatggcta agcacaggga atgtgcgtac    120
g                                                                    121
```

<210> SEQ ID NO 3
<211> LENGTH: 313
<212> TYPE: DNA
<213> ORGANISM: Rattus rattus

<400> SEQUENCE: 3

```
actagtaaaa gcttctaact cttcttgttg ttcattttt ttccttttc ttctttgttt       60 ggattgcagc attctgctct tctgatgatg cgctgtgacc ctgaaagtag cgcaaaggct   120
gcgcaggtta atgcgcattg cgtgcgaatg agcccctgtg aacggttgac tagatgagta   180
atctgattga ctggctctct cagtcctatt ctgtagcctt tttggataaa attgggtttt   240
aacgtacctt gagtccaact aatctcatta agtaaatatt ctctatgggc ctgtctagta   300
gattaatgga tcy                                                      313
```

<210> SEQ ID NO 4
<211> LENGTH: 553
<212> TYPE: DNA
<213> ORGANISM: Rattus rattus
<220> FEATURE:
<221> NAME/KEY: misc_feature
<222> LOCATION: (314)
<223> OTHER INFORMATION: wherein n is A, C, G, or T

<400> SEQUENCE: 4

```
actagtaaaa gcttctaact cttcttgttg ttcattttt ttccttttc ttctttgttt       60 ggattgcagc attctgctct tctgatgatg cgctgtgacc ctgaaagtag cgcaaaggct   120
gcgcagcgtt aatgcgcatt gcgtgcgaat gagcccctgt gaacggttga ctagatgagt   180
aatctgattg actggctctc tcagtcctat tctgtagcct tttggataa aattgggttt    240 taacgtacct tgagtccaac taatctcatt aagtaaatat tctctatggg cctgtctagt   300
agattaatgg atcntggttg ccgtttgct gcgtctaggg gtgttctatg tagcgcagca    360
gttcgcagcg attgcgcagt gcgatgctgt taggtggcgc cagcgatgtt tgcgctcgca   420
ttacagggac atcaacctag gtgcaatcct gtcatgtgag gttttatttt cttcctcctc   480
agaagagaag tgttatgaat ctgaaactta agcctaaag gataatgacc gacttggcag    540
aaagattttt tta                                                      553
```

<210> SEQ ID NO 5
<211> LENGTH: 316
<212> TYPE: DNA
<213> ORGANISM: Rattus rattus
<220> FEATURE:
<221> NAME/KEY: misc_feature
<222> LOCATION: (161)
<223> OTHER INFORMATION: wherein n is A, C, G, or T
<220> FEATURE:
<221> NAME/KEY: misc_feature
<222> LOCATION: (234)
<223> OTHER INFORMATION: wherein n is A, C, G, or T
<220> FEATURE:
<221> NAME/KEY: misc_feature
<222> LOCATION: (239)
<223> OTHER INFORMATION: wherein n is A, C, G, or T
<220> FEATURE:
<221> NAME/KEY: misc_feature

```
<222> LOCATION: (284)
<223> OTHER INFORMATION: wherein n is A, C, G, or T

<400> SEQUENCE: 5
aagcttgtca gtgcacacat agatggtcgg catgtttagc aaactttgtg aaatttaaat    60
aagtttgtag ttacatgtga aactctaaat gcatggtaac cgttgatgtc ataacagttt   120
agttatttcg ttctgttctg tcatgtgcca caaaataagt ntcttttttca cctttttttt   180 gttttttttgg ttttttgttt ttttggtttt tcctgttttt tttgcccttt gtanattant   240
tgaggttaaa actggttcat cctgaaaaaa acgacgaaaa aaancgaaaa agtccattca   300
tattttttaa caattg                                                    316

<210> SEQ ID NO 6
<211> LENGTH: 296
<212> TYPE: DNA
<213> ORGANISM: Rattus rattus
<220> FEATURE:
<221> NAME/KEY: misc_feature
<222> LOCATION: (14)
<223> OTHER INFORMATION: wherein n is A, C, G, or T
<220> FEATURE:
<221> NAME/KEY: misc_feature
<222> LOCATION: (39)
<223> OTHER INFORMATION: wherein n is A, C, G, or T
<220> FEATURE:
<221> NAME/KEY: misc_feature
<222> LOCATION: (47)
<223> OTHER INFORMATION: wherein n is A, C, G, or T

<400> SEQUENCE: 6
caattgtata agtncccaag tcattcacta caccctcang ccttgcnttt gtaatttgac    60
ttctgaaatg tcggcgatca aagcatgcac ctgtaccaat gacaaaagaa aaagcatttt   120
atattactac tcaataaaat gtgcatgaac ttaaagaatg ctcatccttt cactgagtct   180
gctgaaggga atgccatgcg caccaccacg gtgtcctctg ggtgctggcc cttccccacc   240
ctgcacactt aggataggct gcttcccagg gacctcacga tataaggagc ggtacc       296

<210> SEQ ID NO 7
<211> LENGTH: 649
<212> TYPE: DNA
<213> ORGANISM: Rattus rattus

<400> SEQUENCE: 7
ggtaccgctc cttatatcgt gaggtccctg ggaagcagcc tatcctaagt gtgcagggtg    60
gggaagggcc agcacccaga ggacaccgtg gtggtgcgca tggcattccc ttcagcagac   120
tcagtgaaag gatgagcatt ttttttttctt taagttcatg cacattttat tgagtagtaa   180
tataaaatgc ttttctttt gtcattggta caggtgcatg ctttgatcgc cgacatttca   240
gaagtcaaat tacaaaggca aggcttgagg gtgtagtgaa tgacttgggc acttatacaa   300
ttgttaaaaa atatgaatgg acttttctgc tgtttgtcgt cgttgttttc agaatgaacc   360
agttgtaacc tcaactaata tacaaagggc aaaaaaaaca aaaaaaaaca aaaaaaaaca   420
aaaaaacaaa aaaccaaaaa aacaaaaaaa aaggtgaaaa aagtacgta ttttgtggca    480 catgacagaa cagaacgaaa taactaaact gttatgacat caacgttac catgcattta   540 gagtttcaca tgtaactaca aacttaatta aatttcacaa agtttgctaa acatgccgac   600
catctatgtg tgcactgaca agcttatgtt aaaaactttt aagaatact                649

<210> SEQ ID NO 8
```

<211> LENGTH: 648
<212> TYPE: DNA
<213> ORGANISM: Rattus rattus

<400> SEQUENCE: 8

```
ggtaccgctc cttatatcgt gaggtccctg ggaagcagcc tatcctaagt gtgcagggtg      60
gggaagggcc agcacccaga ggacaccgtg gtggtgcgca tggcattccc ttcagcagac     120
tcagtgaaag gatgagcatt tttttttctt taagttcatg cacattttat tgagtagtaa     180
tataaaatgc ttttctttt gtcattggta caggtgcatg ctttgatcgc cgacatttca     240
gaagtcaaat tacaaaggca aggcttgagg gtgtagtgaa tgacttgggc acttatacaa     300
ttgttaaaaa atatgaatgg acttttctgc tgtttgtcgt cgttgttttc agaatgaacc     360
agttgtaacc tcaactaata tacaaagggc aaaaaaaaca aaaaaaaaca aaaaaaaca     420
aaaaaacaaa aaaccaaaaa aacaaaaaaa aggtgaaaaa aagtacgtat tttgtggcac     480
atgacagaac agaacgaaat aactaaactg ttatgacatc aacggttacc atgcatttag     540
agtttcacat gtaactacaa acttatttaa atttcacaaa gtttgctaaa catgccgacc     600
atctatgtgt gcactgacaa gcttatgtta aaaactttta agaatact                  648
```

<210> SEQ ID NO 9
<211> LENGTH: 113
<212> TYPE: DNA
<213> ORGANISM: Rattus rattus

<400> SEQUENCE: 9

```
tctagattgt ctgggctgga gtattctgta tggcctggta gacgggaatg ttctgcacgt      60
aaatcatgta tcttcagatg ggacatctct taagtattaa tgttgtgtgt aca            113
```

<210> SEQ ID NO 10
<211> LENGTH: 354
<212> TYPE: DNA
<213> ORGANISM: Rattus rattus
<220> FEATURE:
<221> NAME/KEY: misc_feature
<222> LOCATION: (60)
<223> OTHER INFORMATION: wherein n is A, C, G, or T
<220> FEATURE:
<221> NAME/KEY: misc_feature
<222> LOCATION: (61)
<223> OTHER INFORMATION: wherein n is A, C, G, or T
<220> FEATURE:
<221> NAME/KEY: misc_feature
<222> LOCATION: (81)
<223> OTHER INFORMATION: wherein n is A, C, G, or T
<220> FEATURE:
<221> NAME/KEY: misc_feature
<222> LOCATION: (86)
<223> OTHER INFORMATION: wherein n is A, C, G, or T
<220> FEATURE:
<221> NAME/KEY: misc_feature
<222> LOCATION: (104)
<223> OTHER INFORMATION: wherein n is A, C, G, or T
<220> FEATURE:
<221> NAME/KEY: misc_feature
<222> LOCATION: (115)
<223> OTHER INFORMATION: wherein n is A, C, G, or T
<220> FEATURE:
<221> NAME/KEY: misc_feature
<222> LOCATION: (121)
<223> OTHER INFORMATION: wherein n is A, C, G, or T
<220> FEATURE:
<221> NAME/KEY: misc_feature
<222> LOCATION: (129)
<223> OTHER INFORMATION: wherein n is A, C, G, or T
<220> FEATURE:
<221> NAME/KEY: misc_feature

```
<222> LOCATION: (210)
<223> OTHER INFORMATION: wherein n is A, C, G, or T

<400> SEQUENCE: 10
caattgggtt tgcctctatt ttggctcctc cttctttta tccctcatgg agcctttgcn      60
ncggaccatt attttacatc ngtttncgac taaagttgtt tagngtaagt accanaggtc    120
naggattana cccaaaaaat taaaatcagg gtattctttt acaggcacat aaagtttctc    180
ttgtaactga acaatgggtc ccaccgcgtn acgcaattct gcactccttt tctctgtact    240
gccatttaat gtgtcattgt acatgtcttt ccgtactctc taatttctt cgtccagcag     300 ccgctcgagg tggttgaaga tcccgcagaa gttgggcagg ctgctcataa gctt          354

<210> SEQ ID NO 11
<211> LENGTH: 314
<212> TYPE: DNA
<213> ORGANISM: Rattus rattus
<220> FEATURE:
<221> NAME/KEY: misc_feature
<222> LOCATION: (40)
<223> OTHER INFORMATION: wherein n is A, C, G, or T
<220> FEATURE:
<221> NAME/KEY: misc_feature
<222> LOCATION: (50)
<223> OTHER INFORMATION: wherein n is A, C, G, or T
<220> FEATURE:
<221> NAME/KEY: misc_feature
<222> LOCATION: (125)
<223> OTHER INFORMATION: wherein n is A, C, G, or T
<220> FEATURE:
<221> NAME/KEY: misc_feature
<222> LOCATION: (142)
<223> OTHER INFORMATION: wherein n is A, C, G, or T

<400> SEQUENCE: 11
ctcgagcggc tgctggacga agaaattagc agagtacggn aagacatgtn caatgacaca     60
ttaaatggca gtacagagaa aaggagtgca gaattgcctg actcggtggg acccattgtt    120
cagtnacaag agaaactta tntgcctgta aagaatacc ctggatttta attttgttgg      180
gagaatcctt ggacctagag ggacttacag ctaaacaact tgaagcagaa acaggatgta    240
aaataatggt ccgaggcaaa ggctccatga gggataaaaa gaaggaggag caaaatagag    300
ggcaaaccca attg                                                     314

<210> SEQ ID NO 12
<211> LENGTH: 363
<212> TYPE: DNA
<213> ORGANISM: Rattus rattus
<220> FEATURE:
<221> NAME/KEY: misc_feature
<222> LOCATION: (88)
<223> OTHER INFORMATION: wherein n is A, C, G, or T

<400> SEQUENCE: 12
caattgggtt tgccctctat tttggctcct ccttcttttt atccctcatg gagcctttgc     60
ctcggaccat tattttacat cctgtttnct gactacaagt tgtttagctg taagtaccac    120
taggtccaag gattataccc aacaaaatta aaatccaggg tattcttta caggcacata     180 aagtttctct tgtaactgaa caatgggtcc caccgagtca cgcaattctg cactccttt    240 ctctgtactg ccatttaatg tgtcattgta catgtctttc cgtactctgc taatttcttc    300
gtccagcagc cgctcgaggt ggttgaagat cccgcagaag ttgggcaggc tgctcataag    360
ctt                                                                  363
```

<210> SEQ ID NO 13
<211> LENGTH: 2092
<212> TYPE: DNA
<213> ORGANISM: Homo sapiens

<400> SEQUENCE: 13

| | | | | | |
|---|---|---|---|---|---|
| ggcggagtga | gctgcggagc | ctggaatatg | gtcggggaaa | tggaaacgaa | ggagaagccg | 60 |
| aagcccaccc | cagattacct | gatgcagctg | atgaacgaca | agaagctcat | gagcagcctg | 120 |
| cccaacttct | gcgggatctt | caaccacctc | gagcggctgc | tggacgaaga | aattagcaga | 180 |
| gtacggaaag | acatgtacaa | tgacacatta | aatggcagta | cagagaaaag | gagtgcagaa | 240 |
| ttgcctgatg | ctgtgggacc | tattgttaag | ttacaagaga | aactttatgt | gcctgtaaaa | 300 |
| gaatacccag | attttaattt | tgttgggaga | atccttggac | ctagaggact | tacagccaaa | 360 |
| caacttgaag | cagaaaccgg | atgtaaaatc | atggtccgag | gcaaaggctc | aatgagggat | 420 |
| aaaaaaaagg | aggagcaaaa | tagaggcaag | cccaattggg | agcatctaaa | tgaagattta | 480 |
| catgtactaa | tcactgtgga | agatgctcag | aacagagcag | aaatcaaatt | gaagagagca | 540 |
| gttgaagaag | tgaagaaatt | attggtacct | gcagcagaag | gagaagacag | cctgaagaag | 600 |
| atgcagctga | tggagcttgc | gattctgaat | ggcacctaca | gagatgccaa | cattaaatca | 660 |
| ccagcccttg | cctttctctc | tgcagcaaca | gcccaggctg | ctccaaggat | cattactggg | 720 |
| cctgcgccgg | ttctcccacc | agctgccctg | cgtactccta | cgccagctgg | ccctaccata | 780 |
| atgcctttga | tcagacaaat | acagaccgct | gtcatgccaa | acggaactcc | tcacccaact | 840 |
| gctgcaatag | ttcctccagg | gcccgaagct | ggtttaatct | atacacccta | tgagtacccc | 900 |
| tacacattgg | caccagctac | atcaatcctt | gagtatccta | ttgaacctag | tggtgtatta | 960 |
| ggtgcggtgg | ctactaaagt | tcgaaggcac | gatatgcgtg | tccatcctta | ccaaaggatt | 1020 |
| gtgaccgcag | accgagccgc | caccggcaac | taacctatga | ccttctgacc | tctgaactct | 1080 |
| tcacccaatg | atgacctgac | catgcctgcc | tgctgatcag | ttaactggta | atcgcctttg | 1140 |
| cttgcctgtc | gtcagtgcag | cgagctgagg | cacttgtccg | ttcgtcttac | catctaacca | 1200 |
| aacaaaagac | aaagaaattg | ttgtcctcca | actcagcttt | tttttttttt | ttcctgtttg | 1260 |
| ggtgaaagtg | gttctagaaa | ctgcactgaa | tagtagtaaa | gcaataaggc | ccaattcatc | 1320 |
| ccacagcact | gatcatcttt | taatatccca | ccctaagcga | acggtaagaa | ggcctctctt | 1380 |
| aagaagggga | gacagatggt | ccttaactac | tcaatgacag | aggcagttac | tgtgagagac | 1440 |
| ttctaggaat | ctttttcttc | tcatagcgaa | gtcaaagctc | tctctgaatg | tactgtgtga | 1500 |
| tgatgcatca | tgcatgaacc | ttcggtcagg | gatatcattg | gtgaagtgat | ttcaaaaagt | 1560 |
| attcaaaatt | tgatatgctg | tttagtcact | acagtgccct | caagggcag | aagttgcagc | 1620 |
| cttttttata | ttgcctgcca | aaatttgaag | tattagaaga | agtgtgcca | tgagagaaaa | 1680 |
| acttaaggag | ttttgaaaag | taatgcaaat | aacaaaactg | caacactatt | tttaaaaga | 1740 |
| taaatatctg | agttaaaatt | actgaatctt | tattttacac | ctaaaaaaat | atgagaacaa | 1800 |
| ggtacatgca | ttatgtgtca | cattactggg | caaactgttc | aagtatttt | ttttaaacct | 1860 |
| ccctgtatag | aaaaaaatca | ttaaggatgt | aaaagccatg | cttgcctatt | tgctgtatac | 1920 |
| atgtaatgaa | attgtagata | aagtgtagtg | cattgaaaca | aatgaaccaa | aagtagatac | 1980 |
| ttttactata | caagggtgct | ggtgcagaaa | aaatatatat | attttgggaa | atgtagcatt | 2040 |
| ttatactttc | aagtgttata | gaaaaaaaaa | aaaaaaaaaa | aaaaaaaaaa | aa | 2092 |

<210> SEQ ID NO 14
<211> LENGTH: 341
<212> TYPE: PRT
<213> ORGANISM: Homo sapiens

<400> SEQUENCE: 14

```
Met Val Gly Glu Met Glu Thr Lys Glu Lys Pro Lys Pro Thr Pro Asp
 1               5                  10                  15

Tyr Leu Met Gln Leu Met Asn Asp Lys Lys Leu Met Ser Ser Leu Pro
                20                  25                  30

Asn Phe Cys Gly Ile Phe Asn His Leu Glu Arg Leu Leu Asp Glu Glu
            35                  40                  45

Ile Ser Arg Val Arg Lys Asp Met Tyr Asn Asp Thr Leu Asn Gly Ser
        50                  55                  60

Thr Glu Lys Arg Ser Ala Glu Leu Pro Asp Ala Val Gly Pro Ile Val
 65                  70                  75                  80

Lys Leu Gln Glu Lys Leu Tyr Val Pro Val Lys Glu Tyr Pro Asp Phe
                85                  90                  95

Asn Phe Val Gly Arg Ile Leu Gly Pro Arg Gly Leu Thr Ala Lys Gln
            100                 105                 110

Leu Glu Ala Glu Thr Gly Cys Lys Ile Met Val Arg Gly Lys Gly Ser
        115                 120                 125

Met Arg Asp Lys Lys Glu Glu Gln Asn Arg Gly Lys Pro Asn Trp
130                 135                 140

Glu His Leu Asn Glu Asp Leu His Val Leu Ile Thr Val Glu Asp Ala
145                 150                 155                 160

Gln Asn Arg Ala Glu Ile Lys Leu Lys Arg Ala Val Glu Glu Val Lys
                165                 170                 175

Lys Leu Leu Val Pro Ala Ala Glu Gly Glu Asp Ser Leu Lys Lys Met
            180                 185                 190

Gln Leu Met Glu Leu Ala Ile Leu Asn Gly Thr Tyr Arg Asp Ala Asn
        195                 200                 205

Ile Lys Ser Pro Ala Leu Ala Phe Ser Leu Ala Ala Thr Ala Gln Ala
    210                 215                 220

Ala Pro Arg Ile Ile Thr Gly Pro Ala Pro Val Leu Pro Pro Ala Ala
225                 230                 235                 240

Leu Arg Thr Pro Thr Pro Ala Gly Pro Thr Ile Met Pro Leu Ile Arg
                245                 250                 255

Gln Ile Gln Thr Ala Val Met Pro Asn Gly Thr Pro His Pro Thr Ala
            260                 265                 270

Ala Ile Val Pro Pro Gly Pro Glu Ala Gly Leu Ile Tyr Thr Pro Tyr
        275                 280                 285

Glu Tyr Pro Tyr Thr Leu Ala Pro Ala Thr Ser Ile Leu Glu Tyr Pro
    290                 295                 300

Ile Glu Pro Ser Gly Val Leu Gly Ala Val Ala Thr Lys Val Arg Arg
305                 310                 315                 320

His Asp Met Arg Val His Pro Tyr Gln Arg Ile Val Thr Ala Asp Arg
                325                 330                 335

Ala Ala Thr Gly Asn
            340
```

<210> SEQ ID NO 15
<211> LENGTH: 2473
<212> TYPE: DNA
<213> ORGANISM: Homo sapiens

```
<400> SEQUENCE: 15
ggaatatggt cggggaaatg gaaacgaagg agaagccgaa gcccacccca gattacctga      60
tgcagctgat gaacgacaag aagctcatga gcagcctgcc caacttctgc gggatcttca     120
accacctcga gcggctgctg gacgaagaaa ttagcagagt acggaaagac atgtacaatg     180
acacattaaa tggcagtaca gagaaaagga gtgcagaatt gcctgatgct gtgggaccta     240
ttgttcagtt acaagagaaa ctttatgtgc ctgtaaaaga atacccagat tttaattttg     300
ttgggagaat ccttggacct agaggactta cagccaaaca acttgaagca gaaaccggat     360
gtaaaatcat ggtccgaggc aaaggctcaa tgagggataa aaaaaaggag gagcaaaata     420
gaggcaagcc caattgggag catctaaatg aagatttaca tgtactaatc actgtggaag     480
atgctcagaa cagagcagaa atcaaattga agagagcagt tgaagaagtg aagaaattat     540
tggtacctgc agcagaagga gaagacagcc tgaagaagat gcagctgatg gagcttgcga     600
ttctgaatgg cacctacaga gatgccaaca ttaaatcacc agcccttgcc tttctcttg      660
cagcaacagc ccaggctgct ccaaggatca ttactgggcc tgcgccggtt ctcccaccag     720
ctgccctgcg tactcctacg ccagctggcc ctaccataat gcctttgatc agacaaatac     780
agaccgctgt catgccaaac ggaactcctc acccaactgc tgcaatagtt cctccagggc     840
ccgaagctgg tttaatctat acaccctatg agtacccccta cacattggca ccagctacat     900
caatccttga gtatcctatt gaacctagtg gtgtattaga gtggattgaa atgccagtca     960
tgcctgatat ttcagcccat tgacttgctg atgaaggac tagaatacag cagctgttat    1020
aacacgacca gtcaatgtgg aacaaactgt tctgtgcaa ccccttttgtt ttaccagaca    1080
aaatttgaat acttttttc ctgaattgta tatgaccttg gtgctgcatg catgctgttg    1140
acttttagga ctttgatctt ttaaggtttt tttccccagc attaatattg atttataaag    1200
atttgaaaat cttttaatga actggagaac actaagattt aaactcgaaa attcgttgtt    1260
caagtaaaga aagccatgat gctctgtatg ttatctgtgt gtgtgcatgc actcaggtgc    1320
cctttgtttc atgaacaaat acatttcatt gtacatgttt tctgttttaa tcattgtata    1380
aagtaattgc aggtcagaat tataccacag aactgtttat gagaggcttg tgtctgttgc    1440
acatttcttg aagcattttt aaaataacat gtaacctgta accttgttgt ttaagttttc    1500
ttttctatta atactctgtc ctgtggtccc gtgcatgctc cttttcccag aactcctctc    1560
tgctgcaccc acagcatctg ttcccgagga gttatgactc ttgacttcct gcagggctgg    1620
ggctcttagc caccagctgc tgttccagca cttttcagcgc aagatctccc tgattttgcc    1680
acgtggaatt gtacttgtat atgattacct tatctaaaat gaataagagg tgatggacca    1740
gtttactgct tagaaatagc aagaggcact gcagtaaaac ttgtttctca ttgtaaagct    1800
tcatgtcttt tgtttgttgg aaaatttta cttatagaaa cttaattatt agactggtaa    1860
aataaagacc aaaatatgca gatttctaat tggcattcat aaggtgaata ataataagtg    1920
cccaatgaaa aaatctatta tggttaattt catttcttgc tttgccacct aagcagtaaa    1980
acatgatatt gaccacttgg agaactcaga aaattatttt aaatttctaa gttataataa    2040
atttgcacac agataaacatg catgctattt atgtcacatc tcacattaaa ttattttaaa    2100
ataagcagtg cccttcaaaa cagatgcaga catgtgtgtt ggtagtagtg aggagattgg    2160
tattagcatc aagtcttcat tgatgactaa ttttaattc ccttcctttt atctttaggt    2220
atggctttcc caacgaaagg ctaagaattc aagaacggtt ttaactgaac cctcatcaga    2280
tctgaattta acaaatgctt agtctcagca gcctccgggg gaaaaaagct tagcctagca    2340
```

-continued

```
gtcagtgact tacttgcact ttttgcacat agatataaag taaaattatg ttattaattt    2400
ggtttagtct gtaatattac acagtaatgg taatttataa aggagtgtat agtagtatac    2460
tgactgctaa gtg                                                        2473
```

<210> SEQ ID NO 16
<211> LENGTH: 325
<212> TYPE: PRT
<213> ORGANISM: Homo sapiens

<400> SEQUENCE: 16

```
Met Val Gly Glu Met Glu Thr Lys Glu Lys Pro Lys Pro Thr Pro Asp
  1               5                  10                  15

Tyr Leu Met Gln Leu Met Asn Asp Lys Lys Leu Met Ser Ser Leu Pro
                 20                  25                  30

Asn Phe Cys Gly Ile Phe Asn His Leu Glu Arg Leu Leu Asp Glu Glu
             35                  40                  45

Ile Ser Arg Val Arg Lys Asp Met Tyr Asn Asp Thr Leu Asn Gly Ser
         50                  55                  60

Thr Glu Lys Arg Ser Ala Glu Leu Pro Asp Ala Val Gly Pro Ile Val
 65                  70                  75                  80

Gln Leu Gln Glu Lys Leu Tyr Val Pro Val Lys Glu Tyr Pro Asp Phe
                 85                  90                  95

Asn Phe Val Gly Arg Ile Leu Gly Pro Arg Gly Leu Thr Ala Lys Gln
            100                 105                 110

Leu Glu Ala Glu Thr Gly Cys Lys Ile Met Val Arg Gly Lys Gly Ser
            115                 120                 125

Met Arg Asp Lys Lys Lys Glu Glu Gln Asn Arg Gly Lys Pro Asn Trp
130                 135                 140

Glu His Leu Asn Glu Asp Leu His Val Leu Ile Thr Val Glu Asp Ala
145                 150                 155                 160

Gln Asn Arg Ala Glu Ile Lys Leu Lys Arg Ala Val Glu Glu Val Lys
                165                 170                 175

Lys Leu Leu Val Pro Ala Ala Glu Gly Glu Asp Ser Leu Lys Lys Met
            180                 185                 190

Gln Leu Met Glu Leu Ala Ile Leu Asn Gly Thr Tyr Arg Asp Ala Asn
            195                 200                 205

Ile Lys Ser Pro Ala Leu Ala Phe Ser Leu Ala Ala Thr Ala Gln Ala
        210                 215                 220

Ala Pro Arg Ile Ile Thr Gly Pro Ala Pro Val Leu Pro Pro Ala Ala
225                 230                 235                 240

Leu Arg Thr Pro Thr Pro Ala Gly Pro Thr Ile Met Pro Leu Ile Arg
                245                 250                 255

Gln Ile Gln Thr Ala Val Met Pro Asn Gly Thr Pro His Pro Thr Ala
            260                 265                 270

Ala Ile Val Pro Pro Gly Pro Glu Ala Gly Leu Ile Tyr Thr Pro Tyr
        275                 280                 285

Glu Tyr Pro Tyr Thr Leu Ala Pro Ala Thr Ser Ile Leu Glu Tyr Pro
    290                 295                 300

Ile Glu Pro Ser Gly Val Leu Glu Trp Ile Glu Met Pro Val Met Pro
305                 310                 315                 320

Asp Ile Ser Ala His
                325
```

```
<210> SEQ ID NO 17
<211> LENGTH: 331
<212> TYPE: DNA
<213> ORGANISM: Rattus rattus
<220> FEATURE:
<221> NAME/KEY: misc_feature
<222> LOCATION: (234)
<223> OTHER INFORMATION: wherein n is A, C, G, or T

<400> SEQUENCE: 17
actagtggga gggcacatgg aatcgagatg gagaacctga ccctagtatt gagtgctggg     60
cctgtaccta gtgaaggtga ttgaggcagt ggtgagcagt aggtgttttt gaggccttga    120
ggccactgtt taggttgggc aggatagata gacccaggtc tcccagccca ggtgcaaatc    180
atccctcaga ttctgaggct cccttttttc cttcatccat gtgtttctag atgntgcggg    240
aaatgtagtc tttccctctc agggttccct gtagctttag ttgccctaat ggtggtgggt    300
gtggggtctg tatgagtact caggtaagct t                                   331

<210> SEQ ID NO 18
<211> LENGTH: 66
<212> TYPE: DNA
<213> ORGANISM: Rattus rattus

<400> SEQUENCE: 18
tccctgtagc tttagttgcc ctaatggtgg tgggtgtggg gtctgtatga gtactcaggt     60
aagctt                                                                66

<210> SEQ ID NO 19
<211> LENGTH: 195
<212> TYPE: DNA
<213> ORGANISM: Rattus rattus
<220> FEATURE:
<221> NAME/KEY: misc_feature
<222> LOCATION: (126)
<223> OTHER INFORMATION: wherein n is A, C, G, or T
<220> FEATURE:
<221> NAME/KEY: misc_feature
<222> LOCATION: (127)
<223> OTHER INFORMATION: wherein n is A, C, G, or T

<400> SEQUENCE: 19
gccggcaact cctgggggcc tgcgaggag gcgggcttcc cggggggtggg gtaggggttg     60 ggacacggga ctgcttacct ggagacccca agcttacctg agtactcata cagaccccac   120
acccannacc attagggcaa ctaaagctac agggaaccct gagagggaaa gactacattt   180
cccacatcat ctaga                                                     195

<210> SEQ ID NO 20
<211> LENGTH: 420
<212> TYPE: DNA
<213> ORGANISM: Rattus rattus

<400> SEQUENCE: 20
actagtggga gggcacatgg aatcgagatg gagaacctga ccctagtatt gagtgctggg     60
cctgtaccta gtgaaggtga ttgaggcagt ggtgagcagt aggtgttttt gaggccttga    120
ggccactgtt taggttgggc aggatagata gacccaggtc tcccagccca ggtgcaaatc    180
atccctcaga ttctgaggct cccttttttc cttcatccat gtgtttctag atgatgcggg    240
aaatgtagtc tttccctctc agggttccct gtagctttag ttgccctaat ggtggtgggt    300
gtggggtctg tatgagtact caggtaagct tggggtctcc aggtaagcag tcccgtgtcc    360
```

```
caaccoctac ccacccccg ggaagcccgc ctcctcgcca ggcccccagg agttgccggc        420
```

<210> SEQ ID NO 21
<211> LENGTH: 179
<212> TYPE: DNA
<213> ORGANISM: Rattus rattus
<220> FEATURE:
<221> NAME/KEY: misc_feature
<222> LOCATION: (95)
<223> OTHER INFORMATION: wherein n is A, C, G, or T

<400> SEQUENCE: 21

```
acgcgtgccg tttgttttga cgcaggattt cttaatagtg attagtaaag gagcacaaga         60
gtacacaaag accagagagt ttgagaggtt tcagngaatg tgttacaagg cgtacctagc        120
aattcggcag catgccaatt ctcttcatca acctttctc catgatgctt ggctccgga         179
```

<210> SEQ ID NO 22
<211> LENGTH: 94
<212> TYPE: DNA
<213> ORGANISM: Rattus rattus

<400> SEQUENCE: 22

```
agatctgctg tggaattggt attgtatgtc catgggatcc tcttttctca gcacgtgttc         60
ctcactagaa gaaaatgctg ttacctttaa gctt                                     94
```

<210> SEQ ID NO 23
<211> LENGTH: 230
<212> TYPE: DNA
<213> ORGANISM: Rattus rattus

<400> SEQUENCE: 23

```
tcatgatgga cccttcccct gcccccagtg gtggcccgag ttgttaagtg cgattggtta         60
gagtagattc cagtcaggtc attctgctgg aggagtgggg gcagtggcag gtaagggggct       120 cagttgctgc agcactggct ccggttggct gggttgctct cctgcagatc cacacctctg       180
tttcggcctg gagcaccagc tgcattctgg ggctcaatct tgggaagctt                  230
```

<210> SEQ ID NO 24
<211> LENGTH: 256
<212> TYPE: DNA
<213> ORGANISM: Rattus rattus
<220> FEATURE:
<221> NAME/KEY: misc_feature
<222> LOCATION: (45)
<223> OTHER INFORMATION: wherein n is A, C, G, or T
<220> FEATURE:
<221> NAME/KEY: misc_feature
<222> LOCATION: (202)
<223> OTHER INFORMATION: wherein n is A, C, G, or T

<400> SEQUENCE: 24

```
aagcttccca agaatgagcc ccagaatgca gctggtgctc caggncgaaa cagaggtgtg         60
gatctgcagg agagcaaccc agccagccgg agccagtgct gcagcaactg agccccttac       120
ctgccactgc ccccactcct ccagcagaat gacctgactg gaatctactc taaccaatca       180
cacttaacaa ctcggaccac cnctgggggc aggggaaggg tccatcatga attctccgca       240
taactttgat cctagg                                                        256
```

<210> SEQ ID NO 25
<211> LENGTH: 234
<212> TYPE: DNA
<213> ORGANISM: Rattus rattus

```
<220> FEATURE:
<221> NAME/KEY: misc_feature
<222> LOCATION: (134)
<223> OTHER INFORMATION: wherein n is A, C, G, or T
<220> FEATURE:
<221> NAME/KEY: misc_feature
<222> LOCATION: (135)
<223> OTHER INFORMATION: wherein n is A, C, G, or T

<400> SEQUENCE: 25
aagcttccca agaatgagcc ccagaatgca gctggtgctc caggccgaaa cagaggtgtg      60
gatctgcagg agagcaaccc agccagccgg agccagtgct gcagcaactg agccccttac    120
ctgccactgc cccnnctcct ccagcagaat ggcctgactg gaatctactc taaccaatcg    180
cacttaacaa ctcgggccac cattgggggc aggggaaggg tccatcatga attc          234

<210> SEQ ID NO 26
<211> LENGTH: 88
<212> TYPE: DNA
<213> ORGANISM: Rattus rattus
<220> FEATURE:
<221> NAME/KEY: misc_feature
<222> LOCATION: (20)
<223> OTHER INFORMATION: wherein n is A, C, G, or T
<220> FEATURE:
<221> NAME/KEY: misc_feature
<222> LOCATION: (21)
<223> OTHER INFORMATION: wherein n is A, C, G, or T

<400> SEQUENCE: 26
ggatccacac ctctgtttcn ncctggagca ccagctgcat tctggggctc attcttggga     60
agcttcttag ctatcgccat gaaaattt                                        88

<210> SEQ ID NO 27
<211> LENGTH: 279
<212> TYPE: DNA
<213> ORGANISM: Rattus rattus

<400> SEQUENCE: 27
cctaggatca aagttatgcg gagaattcat gatggaccct tccctgccc ccagtggtgg      60 cccgagttgt taagtgcgat tggttagagt agattccagt caggtcattc tgctggagga   120
gtgggggcag tggcaggtaa ggggctcagt tgctgcagca ctggctccgg ctggctgggt   180
tgctctcctg cagatccaca cctctgtttc ggcctggagc accagctgca ttctggggct   240
cattcttggg aagcttctta gctatcgcca tgaaaattt                           279

<210> SEQ ID NO 28
<211> LENGTH: 243
<212> TYPE: DNA
<213> ORGANISM: Rattus rattus

<400> SEQUENCE: 28
agatctctct aactttacat tttcattcca tctgtagatt tttctatctt tataaaatat     60
tggagttatt ttttaaggaa aaatagaaaa gtagcttgtg aatagctcaa accaagctta   120
cacatcgccg catgtaaaaa gcaggaaagt tatttgtgtc tgtttatgtt gcttcctttt   180
gtagcctttg taccctggac gggtgacagt aagggccgag caggagaggc gcgaccttgt   240
aca                                                                  243

<210> SEQ ID NO 29
<211> LENGTH: 516
<212> TYPE: DNA
```

<213> ORGANISM: Rattus rattus

<400> SEQUENCE: 29

| | | | | | |
|---|---|---|---|---|---|
| gaagtaactg | actaaaaaga | gaacgagata | cacacaagag | tgctgctggc | tcctgttttg | 60 |
| tacaaggtcg | cgcctctcct | gctcggccct | tactgtcacc | cgtccagggt | acaaaggcta | 120 |
| caaaaggaag | caacataaac | agacacaaat | aactttcctg | cttttacat | gcggcgatgt | 180 |
| gtaagcttgg | tttgagctat | tcacaagcta | cttttctatt | tttccttaaa | aaataactcc | 240 |
| aatatttat | aaagatagaa | aaatctacag | atggaatgaa | aatgtaaagt | tagagagatc | 300 |
| tccataaaat | agggacttca | caccacactc | actgttcctt | gaatcctgct | gcgtgttccg | 360 |
| acatgtatga | aatgcttcag | aacctgacag | gcaaacactg | agatatgctc | attcaataaa | 420 |
| cacaagtgtg | cgcttataaa | acagaaagct | gcctctcccc | aaaggagcct | gtcgccaaaa | 480 |
| tggaaaaggg | tcttctcaac | tttacaccaa | acattt | | | 516 |

<210> SEQ ID NO 30
<211> LENGTH: 216
<212> TYPE: DNA
<213> ORGANISM: Rattus rattus

<400> SEQUENCE: 30

| | | | | | |
|---|---|---|---|---|---|
| aagcttttat | cacgtaacca | gctgaacaac | acaccaaaag | cagcctaggg | atgagcaccg | 60 |
| cgctttggta | gcgattaggt | tttattcacc | tggtattaaa | actattcact | atttcaaaaa | 120 |
| tccggaactt | ttaagaattc | atttgcaagg | cagcatcaaa | aactgaaaag | gaagggaaaa | 180 |
| aaaaacaaca | gctaataatc | ggcttctccg | cacgct | | | 216 |

<210> SEQ ID NO 31
<211> LENGTH: 859
<212> TYPE: DNA
<213> ORGANISM: Rattus rattus

<400> SEQUENCE: 31

| | | | | | |
|---|---|---|---|---|---|
| cgttttataa | atttaatcat | ttgctaatgg | aaattttacc | acctcccatt | tgtgttacaa | 60 |
| atcttagctc | ctggagcggc | actacaattc | aggagttgtt | ttttctcacc | tcctctgtca | 120 |
| tttgtcacag | gaggtccctg | cttggcaatg | acatttgtga | gttaggataa | tgacgttcct | 180 |
| tctctccttt | ttttttcctt | tcatacttca | gatttaggag | aaaaagattc | tgtttccacg | 240 |
| tgagaggaac | tgtaagcttt | tatcacgtaa | ccagctgaac | aacacaccaa | aagcagccta | 300 |
| gggatgagca | ccgcgctttg | gtagcgatta | ggttttattc | acctggtatt | aaaactattc | 360 |
| actatttcaa | aaatccggaa | cttttaagaa | ttcatttcaa | aggcagcatc | aaaaactgaa | 420 |
| aaggaaggaa | aaaaaaaaca | acagctaata | atcggcttct | ccgcacgcgt | ggagctcgcg | 480 |
| aaactggagc | cccggagaag | tggctctgct | cagccgcccg | cccacgccgc | ggcggtcctt | 540 |
| gctttccccg | catgcgcccg | caggcagcgt | gcagtcctaa | gcccggctgt | ggagaagctc | 600 |
| actctctctc | ttgttctgaa | tggtgtttgt | gtcggtctgc | ctctgtgtat | ggtattatgt | 660 |
| cttataatcc | tgcatcactt | ccatcctatc | cagtcatatc | taatgtagaa | aaattagttt | 720 |
| ccagtgaaag | taatatgtag | tgcttttatg | gtatttgtgt | gcaatatccc | ctcttctatt | 780 |
| gaggatattt | gatgtaaagg | aaaaaaaaaa | agaaaaaaga | aactgagttc | cacaataaaa | 840 |
| tacaaagtgg | caaaagttc | | | | | 859 |

<210> SEQ ID NO 32
<211> LENGTH: 92

```
<212> TYPE: DNA
<213> ORGANISM: Rattus rattus

<400> SEQUENCE: 32
aagcttggta tttgttccct tgtcgtaagt ttaactgata ccaggctggc cttacccttc      60
atgtttcaac atcccttggc taggagagat ct                                    92

<210> SEQ ID NO 33
<211> LENGTH: 472
<212> TYPE: DNA
<213> ORGANISM: Rattus rattus

<400> SEQUENCE: 33
cacagtcccc agccctagaa gagtgtcacc atttgaacag cccaggtgac tgagagtatg      60
ggtaactgcc ccagctatat cattagagtt gagtctctct ggctgtaaaa agaacccttg     120
gtgtctgacc aggtaggcag aatccagaaa gggctacctt tccagagaag tcatggacat     180
tagctcacca ccagggcagt cttttttagg cagatctctc ctagccaagg gatgttgaaa     240
catgaagggt aaggccagcc tggtatcagt taaacttacg acaagggaac aaataccaag     300
ctggtgctgt tggtcttatg gctagctata aaggcttcaa cacaatacaa gccactgccc     360
agtgccatgt gaaggaacaa actggtcttt tggttttctt ttcccttcca gttttaatgt     420
tatgtaatgt atttaaatcc ttatttaaat aaagcttgtt ttcagaaata at             472

<210> SEQ ID NO 34
<211> LENGTH: 369
<212> TYPE: DNA
<213> ORGANISM: Rattus rattus
<220> FEATURE:
<221> NAME/KEY: misc_feature
<222> LOCATION: (253)
<223> OTHER INFORMATION: wherein n is A, C, G, or T
<220> FEATURE:
<221> NAME/KEY: misc_feature
<222> LOCATION: (326)
<223> OTHER INFORMATION: wherein n is A, C, G, or T
<220> FEATURE:
<221> NAME/KEY: misc_feature
<222> LOCATION: (327)
<223> OTHER INFORMATION: wherein n is A, C, G, or T
<220> FEATURE:
<221> NAME/KEY: misc_feature
<222> LOCATION: (329)
<223> OTHER INFORMATION: wherein n is A, C, G, or T
<220> FEATURE:
<221> NAME/KEY: misc_feature
<222> LOCATION: (354)
<223> OTHER INFORMATION: wherein n is A, C, G, or T
<220> FEATURE:
<221> NAME/KEY: misc_feature
<222> LOCATION: (366)
<223> OTHER INFORMATION: wherein n is A, C, G, or T

<400> SEQUENCE: 34
gctagctgag aggggtgggg gtgggcggg gctggagaat atgcaggttc ctgaaggtca       60
gtcggggaag tactgctgct gccctagcac gcttcagtgc ctctttagag tttagagttt     120
tctaaagttt tctgcctgaa atcagcgagt gatgatttca ctgtgaaatg atgtctgatc     180
atcgctctcg ctgtcctgtc agggctccgg ctcctggcaa atgtctgact gaaggaaacc     240
ttagttagac tcncacccag ctgtttggaa atggtaatgg agttgatagc acaccctggg     300
ggaaaaaggc aaactccctt tttgcnnant ctcaattccc agcctcgcct gcanctcggg     360 gatttnaag                                                             369
```

<210> SEQ ID NO 35
<211> LENGTH: 408
<212> TYPE: DNA
<213> ORGANISM: Rattus rattus
<220> FEATURE:
<221> NAME/KEY: misc_feature
<222> LOCATION: (392)
<223> OTHER INFORMATION: wherein n is A, C, G, or T

<400> SEQUENCE: 35

```
gctagctgag aggggtggg gtggggcggg gctggagaat atgcaggtcc ctgaaggtca    60
gtcggggaag tactgctgct gccctagcac gcttcagtgc ctctttagag tttagagttt   120
tctaaagttt tctgcctgaa atcagcgagt gatgatttca ctgtgaaatg atgtctgatc   180
atcgctctcg ctgtcctgtc agggctccgg ctcctggcaa atgtctgact gaaggaaacc   240
ttagttagac tcacacccag ctgtttggaa atggtaatgg agttgatagc acaccctggg   300
ggaaagaggc agactccctt tttgctcact ctcaattccc agcctcgccc tgccagttcg   360
gggatttcta agtaagggtg aatctggacc anatatgtac ttcggaga                408
```

<210> SEQ ID NO 36
<211> LENGTH: 181
<212> TYPE: DNA
<213> ORGANISM: Rattus rattus
<220> FEATURE:
<221> NAME/KEY: misc_feature
<222> LOCATION: (12)
<223> OTHER INFORMATION: wherein n is A, C, G, or T

<400> SEQUENCE: 36

```
gctagctgag angggtggg gtggggcggg gctggagaat atgcaggttc ctgaaggtca    60
gtcggggaag tactgctgct gccctagcac gcttcagtgc ctctttagag tttagagttt   120
tctaaagttt tctgcctgaa atcagcgagt gatgatttca ctgtgaaatg atgtctgatc   180
a                                                                   181
```

<210> SEQ ID NO 37
<211> LENGTH: 226
<212> TYPE: DNA
<213> ORGANISM: Rattus rattus
<220> FEATURE:
<221> NAME/KEY: misc_feature
<222> LOCATION: (49)
<223> OTHER INFORMATION: wherein n is A, C, G, or T

<400> SEQUENCE: 37

```
tgatcatcgc tctcgctgtc ctgtcagggc tccggctcct ggcaaatgng tgactgaagg    60
aaaccttagt tagactcaca cccagctgtt tggaaatggt aatggagttg atagcacacc   120
ctggggaaa gaggcagact ccctttttgc tcactctcaa ttcccagcct cgccctgcca    180
gctcggggat ttctaagtaa gggtgaatct ggaccatata tgtaca                   226
```

<210> SEQ ID NO 38
<211> LENGTH: 409
<212> TYPE: DNA
<213> ORGANISM: Rattus rattus

<400> SEQUENCE: 38

```
gctagctgag aggggtggg gtggggcggg gctggagaat atgcaggtcc ctgaaggtca    60
gtcggggaag tactgctgct gccctagcac gcttcagtgc ctctttagag tttagagttt   120
tctaaagttt tctgcctgaa atcagcgagt gatgatttca ctgtgaaatg atgtctgatc   180
```

```
atcgctctcg ctgtcctgtc agggctccgg ctcctggcaa atgtctgact gaaggaaacc      240
ttagttagac tcacacccag ctgtttggaa atggtaatgg agttgatagc acaccctggg      300
ggaaagaggc agactccctt tttgctcact ctcaattccc agcctcgccc tgccagctcg      360
gggatttcta agtaagggtg aatctggacc atatatgtac attcggaga                 409
```

<210> SEQ ID NO 39
<211> LENGTH: 176
<212> TYPE: DNA
<213> ORGANISM: Rattus rattus

<400> SEQUENCE: 39

```
gaattcacaa caccgggtgg gtaggaaagc agctaacata gcctaggttg gtgcagaagc       60
tcacaagaag tggccaggat gtagaggtgg ctgaccaggt aggtagtaag ggcctctact      120
tgccctcctt aacacacaca cctcactcac ggctttgtac aggagcagcc aatggt         176
```

<210> SEQ ID NO 40
<211> LENGTH: 114
<212> TYPE: DNA
<213> ORGANISM: Rattus rattus

<400> SEQUENCE: 40

```
tgtacagaca atctcttgtg cattctgtgg aagcatcacc tgtcaataaa agctaatgg        60 ccagtgagct agaggcagga ttagattgtg ggaaattgga cagggaactc taga           114
```

<210> SEQ ID NO 41
<211> LENGTH: 207
<212> TYPE: DNA
<213> ORGANISM: Rattus rattus
<220> FEATURE:
<221> NAME/KEY: misc_feature
<222> LOCATION: (44)
<223> OTHER INFORMATION: wherein n is A, C, G, or T
<220> FEATURE:
<221> NAME/KEY: misc_feature
<222> LOCATION: (85)
<223> OTHER INFORMATION: wherein n is A, C, G, or T

<400> SEQUENCE: 41

```
actagttcac aactcattta acccattaaa actattctat gtcngccaca tggctggtta       60
gttacctttc agtttcatac atctngcttc ccatctagag ttccctgtcc aatttcccac      120
aatctaatcc tgcctctagc tcactggcca ttagcttttt attgacaggt gatgcttcca      180
cagaatgcac aagagattgt ctgtaca                                          207
```

<210> SEQ ID NO 42
<211> LENGTH: 176
<212> TYPE: DNA
<213> ORGANISM: Rattus rattus
<220> FEATURE:
<221> NAME/KEY: misc_feature
<222> LOCATION: (13)
<223> OTHER INFORMATION: wherein n is A, C, G, or T
<220> FEATURE:
<221> NAME/KEY: misc_feature
<222> LOCATION: (14)
<223> OTHER INFORMATION: wherein n is A, C, G, or T
<220> FEATURE:
<221> NAME/KEY: misc_feature
<222> LOCATION: (18)
<223> OTHER INFORMATION: wherein n is A, C, G, or T
<220> FEATURE:
<221> NAME/KEY: misc_feature
<222> LOCATION: (19)

```
<223> OTHER INFORMATION: wherein n is A, C, G, or T
<220> FEATURE:
<221> NAME/KEY: misc_feature
<222> LOCATION: (45)
<223> OTHER INFORMATION: wherein n is A, C, G, or T
<220> FEATURE:
<221> NAME/KEY: misc_feature
<222> LOCATION: (46)
<223> OTHER INFORMATION: wherein n is A, C, G, or T
<220> FEATURE:
<221> NAME/KEY: misc_feature
<222> LOCATION: (50)
<223> OTHER INFORMATION: wherein n is A, C, G, or T
<220> FEATURE:
<221> NAME/KEY: misc_feature
<222> LOCATION: (58)
<223> OTHER INFORMATION: wherein n is A, C, G, or T
<220> FEATURE:
<221> NAME/KEY: misc_feature
<222> LOCATION: (59)
<223> OTHER INFORMATION: wherein n is A, C, G, or T
<220> FEATURE:
<221> NAME/KEY: misc_feature
<222> LOCATION: (61)
<223> OTHER INFORMATION: wherein n is A, C, G, or T
<220> FEATURE:
<221> NAME/KEY: misc_feature
<222> LOCATION: (67)
<223> OTHER INFORMATION: wherein n is A, C, G, or T
<220> FEATURE:
<221> NAME/KEY: misc_feature
<222> LOCATION: (70)
<223> OTHER INFORMATION: wherein n is A, C, G, or T
<220> FEATURE:
<221> NAME/KEY: misc_feature
<222> LOCATION: (72)
<223> OTHER INFORMATION: wherein n is A, C, G, or T
<220> FEATURE:
<221> NAME/KEY: misc_feature
<222> LOCATION: (105)
<223> OTHER INFORMATION: wherein n is A, C, G, or T
<220> FEATURE:
<221> NAME/KEY: misc_feature
<222> LOCATION: (111)
<223> OTHER INFORMATION: wherein n is A, C, G, or t
<220> FEATURE:
<221> NAME/KEY: misc_feature
<222> LOCATION: (116)
<223> OTHER INFORMATION: wherein n is A, C, G, or T
<220> FEATURE:
<221> NAME/KEY: misc_feature
<222> LOCATION: (117)
<223> OTHER INFORMATION: wherein n is A, C, G, or T
<220> FEATURE:
<221> NAME/KEY: misc_feature
<222> LOCATION: (118)
<223> OTHER INFORMATION: wherein n is A, C, G, or T
<220> FEATURE:
<221> NAME/KEY: misc_feature
<222> LOCATION: (122)
<223> OTHER INFORMATION: wherein n is A, C, G, or T
<220> FEATURE:
<221> NAME/KEY: misc_feature
<222> LOCATION: (126)
<223> OTHER INFORMATION: wherein n is A, C, G, or T
<220> FEATURE:
<221> NAME/KEY: misc_feature
<222> LOCATION: (130)
<223> OTHER INFORMATION: wherein n is A, C, G, or T
<220> FEATURE:
<221> NAME/KEY: misc_feature
<222> LOCATION: (131)
<223> OTHER INFORMATION: wherein n is A, C, G, or T
<220> FEATURE:
<221> NAME/KEY: misc_feature
<222> LOCATION: (139)
<223> OTHER INFORMATION: wherein n is A, C, G, or T
<220> FEATURE:
<221> NAME/KEY: misc_feature
```

```
<222> LOCATION: (144)
<223> OTHER INFORMATION: wherein n is A, C, G, or T
<220> FEATURE:
<221> NAME/KEY: misc_feature
<222> LOCATION: (148)
<223> OTHER INFORMATION: wherein n is A, C, G, or T
<220> FEATURE:
<221> NAME/KEY: misc_feature
<222> LOCATION: (162)
<223> OTHER INFORMATION: wherein n is A, C, G, or T
<220> FEATURE:
<221> NAME/KEY: misc_feature
<222> LOCATION: (163)
<223> OTHER INFORMATION: wherein n is A, C, G, or T
<220> FEATURE:
<221> NAME/KEY: misc_feature
<222> LOCATION: (176)
<223> OTHER INFORMATION: wherein n is A, C, G, or T

<400> SEQUENCE: 42
tctagagttc ccnntccnnt ttcccacaat ctaatcctgc ctctnnctcn ttgtccgnna      60
ncttttnatn gncaggtgat gcttccacag aatgcacaag agatngtctg nacagnnntc    120
angtcngccn ngtaagccng atgnttgntg tggcctcctg tnntggacag ctttcn        176

<210> SEQ ID NO 43
<211> LENGTH: 90
<212> TYPE: DNA
<213> ORGANISM: Rattus rattus
<220> FEATURE:
<221> NAME/KEY: misc_feature
<222> LOCATION: (25)
<223> OTHER INFORMATION: wherein n is A, C, G, or T
<220> FEATURE:
<221> NAME/KEY: misc_feature
<222> LOCATION: (29)
<223> OTHER INFORMATION: wherein n is A, C, G, or T
<220> FEATURE:
<221> NAME/KEY: misc_feature
<222> LOCATION: (45)
<223> OTHER INFORMATION: wherein n is A, C, G, or T
<220> FEATURE:
<221> NAME/KEY: misc_feature
<222> LOCATION: (52)
<223> OTHER INFORMATION: wherein n is A, C, G, or T
<220> FEATURE:
<221> NAME/KEY: misc_feature
<222> LOCATION: (90)
<223> OTHER INFORMATION: wherein n is A, C, G, or T

<400> SEQUENCE: 43
accggtatgt ataggtatcc acttnaaanc tgtccaacac aggangccac ancaaccatc     60
aggctaacaa ggcagacatg actgctgtan                                     90

<210> SEQ ID NO 44
<211> LENGTH: 542
<212> TYPE: DNA
<213> ORGANISM: Rattus rattus
<220> FEATURE:
<221> NAME/KEY: misc_feature
<222> LOCATION: (8)
<223> OTHER INFORMATION: wherein n is A, C, G, or T
<220> FEATURE:
<221> NAME/KEY: misc_feature
<222> LOCATION: (18)
<223> OTHER INFORMATION: wherein n is A, C, G, or T
<220> FEATURE:
<221> NAME/KEY: misc_feature
<222> LOCATION: (43)
<223> OTHER INFORMATION: wherein n is A, C, G, or T
<220> FEATURE:
<221> NAME/KEY: misc_feature
<222> LOCATION: (67)
```

```
<223> OTHER INFORMATION: wherein n is A, C, G, or T
<220> FEATURE:
<221> NAME/KEY: misc_feature
<222> LOCATION: (72)
<223> OTHER INFORMATION: wherein n is A, C, G, or T
<220> FEATURE:
<221> NAME/KEY: misc_feature
<222> LOCATION: (96)
<223> OTHER INFORMATION: wherein n is A, C, G, or T
<220> FEATURE:
<221> NAME/KEY: misc_feature
<222> LOCATION: (458)
<223> OTHER INFORMATION: wherein n is A, C, G, or T
<220> FEATURE:
<221> NAME/KEY: misc_feature
<222> LOCATION: (499)
<223> OTHER INFORMATION: wherein n is A, C, G, or T

<400> SEQUENCE: 44
tcaccccngt taatgagntg acaggtaccc ctcgaatcaa ggncctactt tgatgagcaa      60
cttaaancct gncttcttga gaaaggcctt ctgagncctg atggtcagcc catgtggcag    120
tgctctccac agactggcat ccagagagga agtggacttg gaatctctgg aatgggacac    180
aaagaacaga atttattctt aggatgaaag ggctttgaga taaggccttg ctttcgtcaa    240
gggggagtag accggtatgt ataggtatcc acttgaaagc tgtccaacac aggaggccac    300
agcaaccatc aggctaacaa ggcagacatg actgctgtac agacaatctc ttgtgcattc    360
tgtggaagca tcacctgtca ataaaaagct aatggccagt gagctagagg caggattaga    420
ttgtgggaaa ttggacaggg aactctagat gggaagcnag atgtatgaaa ctgaaaggta    480
actaaccagc catgtggcng acatagaata gttttaatgg gttaaatgag ttgtgaacta    540
gt                                                                   542

<210> SEQ ID NO 45
<211> LENGTH: 360
<212> TYPE: DNA
<213> ORGANISM: Rattus rattus
<220> FEATURE:
<221> NAME/KEY: misc_feature
<222> LOCATION: (94)
<223> OTHER INFORMATION: wherein n is A, C, G, or T
<220> FEATURE:
<221> NAME/KEY: misc_feature
<222> LOCATION: (213)
<223> OTHER INFORMATION: wherein n is A, C, G, or T
<220> FEATURE:
<221> NAME/KEY: misc_feature
<222> LOCATION: (307)
<223> OTHER INFORMATION: wherein n is A, C, G, or T
<220> FEATURE:
<221> NAME/KEY: misc_feature
<222> LOCATION: (321)
<223> OTHER INFORMATION: wherein n is A, C, G, or T
<220> FEATURE:
<221> NAME/KEY: misc_feature
<222> LOCATION: (340)
<223> OTHER INFORMATION: wherein n is A, C, G, or T
<220> FEATURE:
<221> NAME/KEY: misc_feature
<222> LOCATION: (358)
<223> OTHER INFORMATION: wherein n is A, C, G, or T

<400> SEQUENCE: 45
aagcttcaga cattatggat ggaccagatc ctggcgcccc cgtgaaattg ccttgtctgc      60
cagtgaaact gtcgcctccg ctaccccaa aganagtcct gatctgcatg cctgtagggg    120
gcccagagct ctccctggca ccctacgcag cccagaagag cagccagcag gtgttggccc    180
agcaccacca caccgtcctg ccatcccaga tgnagcacca gctgagttat tcgcagccac    240
```

```
ggccagcatc tcccgtcctc caccggcacc ttacccatgc acccctcggg ctgcaggatg    300
atcgatnagc tgaacaagac ncttgctatg accatgcagn ggctggaaag ctccgagnaa    360
```

<210> SEQ ID NO 46
<211> LENGTH: 247
<212> TYPE: DNA
<213> ORGANISM: Rattus rattus
<220> FEATURE:
<221> NAME/KEY: misc_feature
<222> LOCATION: (8)
<223> OTHER INFORMATION: wherein n is A, C, G, or T
<220> FEATURE:
<221> NAME/KEY: misc_feature
<222> LOCATION: (100)
<223> OTHER INFORMATION: wherein n is A, C, G, or T

<400> SEQUENCE: 46

```
acgcgttnct cggagctttc cagcctctgc atggtcatag caagtgtctt gttcagctca     60
tcgatcatcc tgcagcccga ggggtgcatg ggtaaggtgn cggtggagga cgggagatgc    120
tggccgtggc tgccatactg cagctggtgc tgcatctggg atggcaggac ggtgtggtgg    180
tgctgggcca cagcctgctg gctgctcttc tgggctgcgt aggatgccag ggagagctct    240
ggggccc                                                               247
```

<210> SEQ ID NO 47
<211> LENGTH: 284
<212> TYPE: DNA
<213> ORGANISM: Rattus rattus
<220> FEATURE:
<221> NAME/KEY: misc_feature
<222> LOCATION: (1)
<223> OTHER INFORMATION: wherein n is A, C, G, or T
<220> FEATURE:
<221> NAME/KEY: misc_feature
<222> LOCATION: (2)
<223> OTHER INFORMATION: wherein n is A, C, G, or T
<220> FEATURE:
<221> NAME/KEY: misc_feature
<222> LOCATION: (30)
<223> OTHER INFORMATION: wherein n is A, C, G, or T
<220> FEATURE:
<221> NAME/KEY: misc_feature
<222> LOCATION: (44)
<223> OTHER INFORMATION: wherein n is A, C, G, or T
<220> FEATURE:
<221> NAME/KEY: misc_feature
<222> LOCATION: (81)
<223> OTHER INFORMATION: wherein n is A, C, G, or T
<220> FEATURE:
<221> NAME/KEY: misc_feature
<222> LOCATION: (90)
<223> OTHER INFORMATION: wherein n is A, C, G, or T
<220> FEATURE:
<221> NAME/KEY: misc_feature
<222> LOCATION: (105)
<223> OTHER INFORMATION: wherein n is A, C, G, or T
<220> FEATURE:
<221> NAME/KEY: misc_feature
<222> LOCATION: (243)
<223> OTHER INFORMATION: wherein n is A, C, G, or T
<220> FEATURE:
<221> NAME/KEY: misc_feature
<222> LOCATION: (284)
<223> OTHER INFORMATION: wherein n is A, C, G, or T

<400> SEQUENCE: 47

```
nncccagagc tctccctggc atcctacgcn gcccagaaga gcanccagca ggttgtggcc     60
cagcaccacc acaccgtcct nccatcccan atgcagcacc agctnagtat ggcagccacg    120
```

| | |
|---|---|
| gccagcatct cccgtcctcc accggcacct tacccatgca cccctcgggc tgcagggatg | 180 |
| atcgatgagc tgaacaagac acttgctatg accatgcaga ggctggaaag ctccgagcaa | 240 |
| cgnttcccct gctccacttc ttaccacagc tctggttttg cacn | 284 |

<210> SEQ ID NO 48
<211> LENGTH: 244
<212> TYPE: DNA
<213> ORGANISM: Rattus rattus
<220> FEATURE:
<221> NAME/KEY: misc_feature
<222> LOCATION: (1)
<223> OTHER INFORMATION: wherein n is A, C, G, or T
<220> FEATURE:
<221> NAME/KEY: misc_feature
<222> LOCATION: (8)
<223> OTHER INFORMATION: wherein n is A, C, G, or T
<220> FEATURE:
<221> NAME/KEY: misc_feature
<222> LOCATION: (13)
<223> OTHER INFORMATION: wherein n is A, C, G, or T
<220> FEATURE:
<221> NAME/KEY: misc_feature
<222> LOCATION: (45)
<223> OTHER INFORMATION: wherein n is A, C, G, or T
<220> FEATURE:
<221> NAME/KEY: misc_feature
<222> LOCATION: (61)
<223> OTHER INFORMATION: wherein n is A, C, G, or T
<220> FEATURE:
<221> NAME/KEY: misc_feature
<222> LOCATION: (100)
<223> OTHER INFORMATION: wherein n is A, C, G, or T
<220> FEATURE:
<221> NAME/KEY: misc_feature
<222> LOCATION: (139)
<223> OTHER INFORMATION: wherein n is A, C, G, or T
<220> FEATURE:
<221> NAME/KEY: misc_feature
<222> LOCATION: (179)
<223> OTHER INFORMATION: wherein n is A, C, G, or T
<220> FEATURE:
<221> NAME/KEY: misc_feature
<222> LOCATION: (233)
<223> OTHER INFORMATION: wherein n is A, C, G, or T
<220> FEATURE:
<221> NAME/KEY: misc_feature
<222> LOCATION: (244)
<223> OTHER INFORMATION: wherein n is A, C, G, or T

<400> SEQUENCE: 48

| | |
|---|---|
| ncccgttnct cgntgctttc cagcctctgc atggtcatag caagngtctt tttcggctca | 60 |
| ncgatcatcc tgcagcccga ggggtgcatg ggtaaggtgn cggtggagga cgggagatgc | 120 |
| tggccgtggc gccatactnc agctggtgct gatctgggat gggcaggacg gtgtggtgnt | 180 |
| gctgggccac agcctgctgg ctgctcttct gggctgctta ggatgccagg ganagctctg | 240 |
| ggcn | 244 |

<210> SEQ ID NO 49
<211> LENGTH: 194
<212> TYPE: DNA
<213> ORGANISM: Rattus rattus
<220> FEATURE:
<221> NAME/KEY: misc_feature
<222> LOCATION: (10)
<220> FEATURE:
<221> NAME/KEY: misc_feature
<222> LOCATION: (45)
<223> OTHER INFORMATION: wherein n is A, C, G, or T

<400> SEQUENCE: 49

```
agatctacgn taaagatgga gagctctcca tatcaaatga agatnactcc ctcacaaacg    60
gccagtccct gagctccagc cagctctctt tgcctgctct gtcggaaatg gagcctgtcc   120
caatgcccag ggacccctgc tcatatgagg tgctccaagc ttcagacatt atggatggac   180
cagatcctgg cgcc                                                    194
```

<210> SEQ ID NO 50
<211> LENGTH: 561
<212> TYPE: DNA
<213> ORGANISM: Rattus rattus
<220> FEATURE:
<221> NAME/KEY: misc_feature
<222> LOCATION: (1)
<223> OTHER INFORMATION: wherein n is A, C, G, or T
<220> FEATURE:
<221> NAME/KEY: misc_feature
<222> LOCATION: (312)
<223> OTHER INFORMATION: wherein n is A, C, G, or T
<220> FEATURE:
<221> NAME/KEY: misc_feature
<222> LOCATION: (517)
<223> OTHER INFORMATION: wherein n is A, C, G, or T
<220> FEATURE:
<221> NAME/KEY: misc_feature
<222> LOCATION: (552)
<223> OTHER INFORMATION: wherein n is A, C, G, or T

<400> SEQUENCE: 50

```
ngtgcaaaac cagagctgtg gtaagaagtg gagcagggga acgcgttgct cggagctttc    60
cagcctctgc atggtcatag caagtgtctt gttcagctca tcgatcatcc tgcagcccga   120
ggggtgcatg ggtaaggtgc cggtggagga cgggagatgc tggccgtggc tgccatactg   180
cagctggtgc tgcatctggg atggcaggac ggtgtggtgg tgctgggcca cagcctgctg   240
gctgctcttc tgggctgcgt aggatgccag ggagagctct ggggccccct acaggcatgc   300
agatcaggac tntctttggg ggtagcggag gcgacagttt cactggcaga caaggcaatt   360 tcacggggc gccaggatct ggtccatcca taatgtctga agcttggagc acctcatatg    420 agcagggtc cctgggcatt gggacaggct ccatttccga cagagcaggc aaagagagct    480
ggctggagct cagggactgg ccgtttgtga gggagtnatc ttcatttgat atggagagct   540
ctccatcttt ancgtagatc t                                            561
```

<210> SEQ ID NO 51
<211> LENGTH: 1005
<212> TYPE: DNA
<213> ORGANISM: Homo sapiens

<400> SEQUENCE: 51

```
ggcggagtga gctgcggagc ctggaatatg gtcggggaaa tggaaacgaa ggagaagccg    60
aagcccaccc cagattacct gatgcagctg atgaacgaca agaagctcat gagcagcctg   120
cccaacttct gcgggatctt caaccacctc gagcggctgc tggacgaaga aattagcaga   180
gtacggaaag acatgtacaa tgacacatta atggcagta cagagaaaag gagtgcagaa    240
ttgcctgatg ctgtgggacc tattgttaag ttacaagaga actttatgt gcctgtaaaa    300 gaatacccag attttaattt tgttgggaga tccttggac ctagaggact tacagccaaa    360
caacttgaag cagaaaccgg atgtaaaatc atggtccgag gcaaaggctc aatgagggat   420
aaaaaaaagg aggagcaaaa tagaggcaag cccaattggg agcatctaaa tgaagattta   480
catgtactaa tcactgtgga agatgctcag aacagagcag aaatcaaatt gaagagagca   540
gttgaagaag tgaagaaatt attggtacct gcagcagaag gagaagacag cctgaagaag   600
```

```
atgcagctga tggagcttgc gattctgaat ggcacctaca gagatgccaa cattaaatca      660
ccagcccttg cctttctct tgcagcaaca gcccaggctg ctccaaggat cattactggg      720
cctgcgccgg ttctcccacc agctgccctg cgtactccta cgccagctgg ccctaccata      780
atgcctttga tcagacaaat acagaccgct gtcatgccaa acggaactcc tcacccaact      840
gctgcaatag ttcctccagg gcccgaagct ggtttaatct atacacccta tgagtacccc      900
tacacattgg caccagctac atcaatcctt gagtatccta ttgaacctag tggtgtatta      960
ggtgcggtgg ctactaaagt tcgaaggcac gatatgcgtg tccat                     1005
```

<210> SEQ ID NO 52
<211> LENGTH: 947
<212> TYPE: DNA
<213> ORGANISM: Artificial Sequence
<220> FEATURE:
<223> OTHER INFORMATION: Description of Artificial Sequence:Consensus
      sequence

<400> SEQUENCE: 52

```
ggcggagtga gctgcggagc ctggaatatg gtcggggaaa tggaaacgaa ggagaagccg       60
aagcccaccc cagattatga tgcagctgat gaacgacaag aagctcatga gcagcctgcc      120
caacttctgc gggatcttca accacctcga gcggctgctg gacgaagaaa ttagcagagt      180
acggaaagac atgtacaatg acacttaaat ggcagtacag agaaaagagt gcagaattgc      240
ctgagcgtgg gaccattgtt agttacaaga gaaactttat gtgcctgtaa agaataccc      300 gattttaatt ttgttgggag aatccttgga cctagaggac ttacagcaaa caacttgaag      360
cagaaacgga tgtaaaatat ggtccgaggc aaaggctcaa tgagggataa aaaaggagg      420 agcaaaatag aggcaagccc aattgggagc atctaaatga agattacatg tactaatcac      480
tgtggaagat gctcagaaca gagcagaaat caatgaagag agcgttgaag aagtgaagaa      540
ttatggtacc tgcgcgaagg gaagacagcc tgaagaagat gcagctgatg gagcttgcat      600
tctgaatggc acctacagag agccaacatt aaatcaccag cccttgcctt ttctcttgca      660
gcaacgccca ggctgctcca aggatcatac tgggcctgcg ccgtctccca ccagctgcct      720
gcgtacccta cgccagctgg ccctaccata atgcctttga tcagacaaat acagaccgct      780
gtcatgccaa acggaactcc tcacccaact gctgcaatag tcctccaggg ccgaagctgg      840
ttaatctaac ccctatgat acccctacac attggcacca gctacatcaa tccttgagta      900
cctattgaac cagtggtgtt taggtggtga agtcagcgat atgccat                    947
```

<210> SEQ ID NO 53
<211> LENGTH: 1002
<212> TYPE: DNA
<213> ORGANISM: Mus musculus

<400> SEQUENCE: 53

```
ggcggagtga gctgcggagc ctggaatatg gtcggggaaa tggaaacgaa ggagaagccg       60
aagcccaccc cagattattt gatgcagctg atgaacgaca agaagctcat gagcagcctg      120
cccaacttct gcgggatctt caaccacctc gagcggctgc tggacgaaga attagcaga      180 gtacggaaag acatgtacaa tgacacgtta aatggcagta cagagaaaag aagtgcagaa      240
ttgcctgacg cggtgggacc cattgttcag ttacaagaga actttatgt gcctgtaaaa      300 gaataccctg atttaattt tgttgggaga atccttggac ctagaggact tacagctaaa      360
caacttgaag cagaaacggg atgtaaaata atggtccgag gcaaaggctc aatgagggat      420
```

| | |
|---|---|
| aaaaagaagg aggagcaaaa tagaggcaag cccaattggg agcatctaaa tgaagactta | 480 |
| catgtactaa tcactgtgga agatgctcag aacagagcag aaatcaagct gaagagagcg | 540 |
| gttgaagaag tgaagaagtt actggtacct gcggctgaag gtgaagacag cctgaagaag | 600 |
| atgcagctga tggagcttgc aattctgaat ggcacctaca gagacgccaa cattaaatca | 660 |
| ccagcccttg cctttctct tgcagcaact gcccaggctg ctccaaggat catcactggg | 720 |
| cctgcgcctg tcctcccacc agctgctctg cgtacaccta cgccagctgg ccctaccata | 780 |
| atgcctttga tcagacaaat acagaccgct gtcatgccaa acggaactcc tcacccaact | 840 |
| gctgcaatag tccctccagg gcctgaagct gggttaatct acacaccta tgaatacccc | 900 |
| tacacattgg caccagctac atcaatcctt gagtacccta ttgaacccag tggtgtgtta | 960 |
| gagtggattg aaatgccagt catgcctgat atttcagccc at | 1002 |

<210> SEQ ID NO 54
<211> LENGTH: 80
<212> TYPE: DNA
<213> ORGANISM: Homo sapiens

<400> SEQUENCE: 54

| | |
|---|---|
| attaggtgcg gtggctacta aagttcgaag gcacgatatg cgtgtccatc cttaccaaag | 60 |
| gattgtgacc gcagaccgag | 80 |

<210> SEQ ID NO 55
<211> LENGTH: 80
<212> TYPE: DNA
<213> ORGANISM: Mus musculus

<400> SEQUENCE: 55

| | |
|---|---|
| actaggtgcg gtggctacta aagttcgaag gcacgatatg cgtgtccatc cttaccaaag | 60 |
| gattgtgacc gcagaccgag | 80 |

<210> SEQ ID NO 56
<211> LENGTH: 78
<212> TYPE: DNA
<213> ORGANISM: Homo sapiens

<400> SEQUENCE: 56

| | |
|---|---|
| aaaaaatata tatattttgg gaaatgtagc attttatact ttcaagtgtt atagaaaaaa | 60 |
| aaaaaaaaaa aaaaaaaa | 78 |

<210> SEQ ID NO 57
<211> LENGTH: 56
<212> TYPE: DNA
<213> ORGANISM: Artificial Sequence
<220> FEATURE:
<223> OTHER INFORMATION: Description of Artificial Sequence:Consensus
    sequence

<400> SEQUENCE: 57

| | |
|---|---|
| aaaaattatt tttgaaatga attaactaat tatgaaaaaa aaaaaaaaaa aaaaaa | 56 |

<210> SEQ ID NO 58
<211> LENGTH: 81
<212> TYPE: DNA
<213> ORGANISM: Mus musculus

<400> SEQUENCE: 58

| | |
|---|---|
| aagaaattcc atgttgtttg taaatagaat aattgaaaaa gcaataaaca tttattgaac | 60 |

```
aaaagaaaaa aaaaaaaaaa a                                          81
```

<210> SEQ ID NO 59
<211> LENGTH: 336
<212> TYPE: PRT
<213> ORGANISM: Artificial Sequence
<220> FEATURE:
<223> OTHER INFORMATION: Description of Artificial Sequence:Consensus
      sequence

<400> SEQUENCE: 59

Met Val Gly Glu Met Glu Lys Glu Lys Pro Lys Pro Asp Tyr Leu
 1               5                  10                  15

Met Gln Leu Met Asn Asp Lys Lys Leu Met Ser Ser Leu Pro Asn Phe
                20                  25                  30

Cys Gly Ile Phe Asn His Leu Glu Arg Leu Leu Asp Glu Glu Ile Ser
                35                  40                  45

Arg Val Arg Lys Asp Met Tyr Asn Asp Thr Leu Asn Gly Ser Thr Glu
        50                  55                  60

Lys Arg Ser Ala Glu Leu Pro Asp Ala Val Gly Pro Ile Val Leu Gln
65                  70                  75                  80

Glu Lys Leu Tyr Val Pro Val Lys Glu Tyr Pro Asp Phe Asn Phe Val
                    85                  90                  95

Gly Arg Ile Leu Gly Pro Arg Gly Leu Thr Ala Lys Gln Leu Glu Ala
                100                 105                 110

Glu Thr Gly Cys Lys Ile Met Val Arg Gly Lys Gly Ser Met Arg Asp
            115                 120                 125

Lys Lys Lys Glu Glu Gln Asn Arg Gly Lys Pro Asn Trp Glu His Leu
130                 135                 140

Asn Glu Asp Leu His Val Leu Ile Thr Val Glu Asp Ala Gln Asn Arg
145                 150                 155                 160

Ala Glu Ile Lys Leu Lys Arg Ala Val Glu Glu Val Lys Lys Leu Leu
                165                 170                 175

Pro Ala Ala Glu Gly Glu Asp Ser Leu Lys Lys Met Gln Leu Met Glu
                180                 185                 190

Leu Ala Ile Leu Asn Gly Thr Tyr Arg Asp Ala Asn Ile Lys Ser Pro
            195                 200                 205

Ala Leu Ala Phe Ser Leu Ala Ala Thr Ala Gln Ala Pro Arg Ile Ile
        210                 215                 220

Thr Gly Pro Ala Pro Val Leu Pro Pro Ala Ala Leu Arg Thr Pro Thr
225                 230                 235                 240

Pro Ala Gly Pro Thr Ile Met Pro Leu Ile Arg Gln Ile Gln Thr Ala
                245                 250                 255

Val Met Pro Asn Gly Thr Pro His Pro Thr Ala Ala Ile Val Pro Pro
                260                 265                 270

Gly Pro Glu Ala Gly Leu Ile Tyr Thr Pro Tyr Glu Tyr Pro Tyr Thr
            275                 280                 285

Leu Ala Pro Ala Thr Ser Ile Leu Glu Tyr Pro Ile Glu Pro Ser Gly
        290                 295                 300

Val Leu Gly Ala Val Ala Thr Lys Val Arg Arg His Asp Met Arg Val
305                 310                 315                 320

His Pro Tyr Gln Arg Ile Val Thr Ala Asp Arg Ala Ala Thr Gly Asn
                325                 330                 335

<210> SEQ ID NO 60

<211> LENGTH: 340
<212> TYPE: PRT
<213> ORGANISM: Gallus gallus

<400> SEQUENCE: 60

```
Met Val Gly Glu Met Glu Ala Lys Glu Lys Pro Lys Pro Ser Pro Asp
  1               5                  10                  15

Tyr Leu Met Gln Leu Met Asn Asp Lys Lys Leu Met Ser Ser Leu Pro
                 20                  25                  30

Asn Phe Cys Gly Ile Phe Asn His Leu Glu Arg Leu Leu Asp Glu Glu
             35                  40                  45

Ile Ser Arg Val Arg Lys Asp Met Tyr Asn Asp Thr Leu Asn Gly Ser
         50                  55                  60

Thr Glu Lys Arg Ser Ala Glu Leu Pro Asp Ala Val Gly Pro Ile Val
 65                  70                  75                  80

Gln Leu Gln Glu Lys Leu Tyr Val Pro Val Lys Glu Tyr Pro Asp Phe
                 85                  90                  95

Asn Phe Val Gly Arg Ile Leu Gly Pro Arg Gly Leu Thr Ala Lys Gln
            100                 105                 110

Leu Glu Ala Glu Thr Gly Cys Lys Ile Met Val Arg Gly Lys Gly Ser
            115                 120                 125

Met Arg Asp Lys Lys Glu Glu Gln Asn Arg Gly Lys Pro Asn Trp
            130                 135                 140

Glu His Leu Asn Glu Asp Leu His Val Leu Ile Thr Val Glu Asp Ala
145                 150                 155                 160

Gln Asn Arg Ala Glu Ile Lys Leu Lys Arg Ala Val Glu Glu Val Lys
                165                 170                 175

Lys Leu Leu Ile Pro Ala Ala Glu Gly Glu Asp Ser Leu Lys Lys Met
            180                 185                 190

Gln Leu Met Glu Leu Ala Ile Leu Asn Gly Thr Tyr Arg Asp Ala Asn
            195                 200                 205

Ile Lys Ser Pro Ala Leu Ala Phe Ser Leu Ala Ala Thr Ala Gln Ala
        210                 215                 220

Pro Arg Ile Ile Thr Gly Pro Ala Pro Val Leu Pro Pro Ala Ala Leu
225                 230                 235                 240

Arg Thr Pro Thr Pro Ala Gly Pro Thr Ile Met Pro Leu Ile Arg Gln
                245                 250                 255

Ile Gln Thr Ala Val Met Pro Asn Gly Thr Pro His Pro Thr Ala Ala
            260                 265                 270

Ile Val Pro Pro Gly Pro Glu Ala Gly Leu Ile Tyr Thr Pro Tyr Glu
        275                 280                 285

Tyr Pro Tyr Thr Leu Ala Pro Ala Thr Ser Ile Leu Glu Tyr Pro Ile
    290                 295                 300

Glu Pro Ser Gly Val Leu Gly Ala Val Ala Thr Lys Val Arg Arg His
305                 310                 315                 320

Asp Met Arg Val His Pro Tyr Gln Arg Ile Val Thr Ala Asp Arg Ala
                325                 330                 335

Ala Thr Gly Asn
            340
```

<210> SEQ ID NO 61
<211> LENGTH: 1047
<212> TYPE: DNA
<213> ORGANISM: Homo sapiens

<400> SEQUENCE: 61

```
ggaatatggt cgggaaatg gaaacgaagg agaagccgaa gcccacccca gattacctga    60
tgcagctgat gaacgacaag aagctcatga gcagcctgcc caacttctgc gggatcttca   120
accacctcga gcggctgctg gacgaagaaa ttagcagagt acggaaagac atgtacaatg   180
acacattaaa tggcagtaca gagaaaagga gtgcagaatt gcctgatgct gtgggaccta   240
ttgttcagtt acaagagaaa ctttatgtgc ctgtaaaaga atacccagat tttaattttg   300
ttgggagaat ccttggacct agaggactta cagccaaaca acttgaagca gaaaccggat   360
gtaaaatcat ggtccgaggc aaaggctcaa tgagggataa aaaaaggag gagcaaaata   420 gaggcaagcc caattgggag catctaaatg aagatttaca tgtactaatc actgtggaag   480
atgctcagaa cagagcagaa atcaaattga gagagcagt tgaagaagtg aagaaattat   540
tggtacctgc agcagaagga aagacagcc tgaagaagat gcagctgatg gagcttgcga   600
ttctgaatgg cacctacaga gatgccaaca ttaaatcacc agcccttgcc ttttctcttg   660
cagcaacagc ccaggctgct ccaaggatca ttactgggcc tgcgccggtt ctcccaccag   720
ctgccctgcg tactcctacg ccagctggcc taccataat gcctttgatc agacaaatac   780
agaccgctgt catgccaaac ggaactcctc acccaactgc tgcaatagtt cctccagggc   840
ccgaagctgg tttaatctat acaccctatg agtaccccta cacattggca ccagctacat   900
caatccttga gtatcctatt gaacctagtg gtgtattaga gtggattgaa atgccagtca   960
tgcctgatat ttcagcccat tgacttgctg gatgaaggac tagaatacag cagctgttat  1020
aacacgacca gtcaatgtgg aacaaac                                      1047
```

<210> SEQ ID NO 62
<211> LENGTH: 1047
<212> TYPE: DNA
<213> ORGANISM: Mus musculus

<400> SEQUENCE: 62

```
ggaatatggt cgggaaatg gaaacgaagg agaagccgaa gcccacccca gattatttga    60
tgcagctgat gaacgacaag aagctcatga gcagcctgcc caacttctgc gggatcttca   120
accacctcga gcggctgctg gacgaagaaa ttagcagagt acggaaagac atgtacaatg   180
acacgttaaa tggcagtaca gagaaaagaa gtgcagaatt gcctgacgcg gtgggaccca   240
ttgttcagtt acaagagaaa ctttatgtgc ctgtaaaaga atacctgat tttaattttg    300 ttgggagaat ccttggacct agaggactta cagctaaaca acttgaagca gaaacgggat   360
gtaaaataat ggtccgaggc aaaggctcaa tgagggataa aaagaaggag gagcaaaata   420
gaggcaagcc caattgggag catctaaatg aagacttaca tgtactaatc actgtggaag   480
atgctcagaa cagagcagaa atcaagctga gagagcggt tgaagaagtg aagaagttac   540
tggtacctgc ggctgaaggt gaagacagcc tgaagaagat gcagctgatg gagcttgcaa   600
ttctgaatgg cacctacaga gacgccaaca ttaaatcacc agcccttgcc ttttctcttg   660
cagcaactgc ccaggctgct ccaaggatca tcactgggcc tgcgcctgtc ctcccaccag   720
ctgctctgcg tacacctacg ccagctggcc taccataat gcctttgatc agacaaatac    780
agaccgctgt catgccaaac ggaactcctc acccaactgc tgcaatagtc cctccagggc   840
ctgaagctgg gttaatctac acaccctatg aataccccta cacattggca ccagctacat   900
caatccttga gtaccctatt gaaccagtg gtgtgttaga gtggattgaa atgccagtca    960
tgcctgatat ttcagcccat tgacttgctg gatgaaggac tagaatacag cagctgttat  1020
```

```
aacacgacca gtcaatgtgg aaaaaac                                        1047
```

<210> SEQ ID NO 63
<211> LENGTH: 1156
<212> TYPE: DNA
<213> ORGANISM: Homo sapiens

<400> SEQUENCE: 63

```
tgcccttgt ttcatgaaca aatacatttc attgtacatg ttttctgttt aaatcattgt      60
ataaagtaat tgcaggtcag aattatacca cagaactgtt tatgagaggc ttgtgtctgt    120
tgcacatttc ttgaagcatt tttaaaataa catgtaacct gtaaccttgt tgtttaagtt    180
ttcttttcta ttaatactct gtcctgtggt cccgtgcatg ctccttttcc cagaactcct    240
ctctgctgca cccacagcat ctgttcccga ggagttatga ctcttgactt cctgcagggc    300
tggggctctt agccaccagc tgctgttcca gcactttcag cgcaagatct ccctgatttt    360
gccacgtgga attgtacttg tatatgatta ccttatctaa aatgaataag aggtgatgga    420
ccagtttact gcttagaaat agcaagaggc actgcagtaa aacttgtttc tcattgtaaa    480
gcttcatgtc ttttgtttgt tggaaaattt ttacttatag aaacttaatt attagactgg    540
taaaataaag accaaaatat gcagatttct aattggcatt cataaggtga ataataataa    600
gtgcccaatg aaaaaatcta ttatggttaa tttcatttct tgctttgcca cctaagcagt    660
aaaacatgat attgaccact tggagaactc agaaaattat tttaaatttc taagttataa    720
taaatttgca cacagataac atgcatgcta tttatgtcac atctcacatt aaattatttt    780
aaaataagca gtgcccttca aaacagatgc agacatgtgt gttggtagta gtgaggagat    840
tggtattagc atcaagtctt cattgatgac taattttaa ttcccttcct tttatcttta     900
ggtatggctt tcccaacgaa aggctaagaa ttcaagaacg gtcttaactg aaccctcatc    960
agatctgaat ttaacaaatg cttagtctca gcagcctccg ggggaaaaaa gcttagccta   1020
gcagtcagtg acttacttgc acttttgca catagatata aagtaaaatt atgttattaa    1080
tttggtttag tctgtaatat tacacagtaa tggtaattta taaggagtg tatagtagta    1140
tactgactgc taagtg                                                   1156
```

<210> SEQ ID NO 64
<211> LENGTH: 838
<212> TYPE: DNA
<213> ORGANISM: Artificial Sequence
<220> FEATURE:
<223> OTHER INFORMATION: Description of Artificial Sequence:Consensus
      sequence

<400> SEQUENCE: 64

```
tgccttgtct gaaacattta ttgtacatgt tttctgttaa tttaaaatta gaatacaagt     60
ttaaaggtgt tttcatttat tttaaaaaaa taactgtaac cttttaattt tttttctttc    120
ttgtccgtgg ccctcgctcc ttccgacccc tctgccaagc tcttgttcct gagggtgggc    180
tctagcccag ctgctgtccg acttaggcag ttccatacga ttctttaat atattaaata     240
gtagaccaga ctgcttaaaa tcaatagtaa atgttttgta gcttattttg ttgtgaaaac    300
tataacaata tagataaata accaatcaat caattgatat aatatatata taaatcatat    360
tatatttctt gctttgccac ctaagcagta aaacatgata ttgccttgga gaactagaaa    420
ttatttaaat tcaagttaat aaatttgcac acagataaca tgcatgtatt atcattcaca    480
ttatttaaa ataagcagtg ccttcaaaac agatgcagac attgtgttgg tgtagtgagg     540
```

-continued

```
agattggtat tagcatcaat cttcattgat gactaatttt aattcccttc cttttatctt      600
taggtatggc tttcccaacg aaaggctaag aattcaagaa cggtcttaac gaaccctcat      660
cagatctgaa tttaacaaat cttagtctca gcagctccgg gaaaaactta gcctagcagt      720
cagtgactta cttgcacttt ttgcacatag atataaagta aaatattatt aatttggtta      780
gtctgtaata tcaagaagta atttataaag gagtgataga gtaactgact gctaagtg       838
```

```
<210> SEQ ID NO 65
<211> LENGTH: 1147
<212> TYPE: DNA
<213> ORGANISM: Mus musculus
<220> FEATURE:
<221> NAME/KEY: misc_feature
<222> LOCATION: (989)
<223> OTHER INFORMATION: wherein n is A, C, G, or T
<220> FEATURE:
<221> NAME/KEY: misc_feature
<222> LOCATION: (1122)
<223> OTHER INFORMATION: wherein n is A, C, G, or T

<400> SEQUENCE: 65
```

```
tgcacttagg tgcctttgtt tataaacatt ttattgtaca tgttttctgt cttaagtcat       60
tgtataaaat aattataagt cagaattata caacagaagt gttagtaaga ggctgtattc      120
tattgcacat tacttgaagc attttaaaaa aaaaataaca tgtaacctat atataaccttt     180 atttaagttt tcctttctat taattctctg tcctgtggcc cccgtgcatg ctccttcccc      240
agaactcctc tctgccgcac tcacagaagc tcttgttcct gaggagttag ggctctcagc      300
ttccagctgc tgctcctgac tgttagtgcc tagttttgcc aaatagaatt actatgcagt      360
ctgcttatct aaaatgaaaa ataggttttc aaccagttta ctgcttagag acagcaagag      420
gcactgctgt aaaatttctc cattataaag taacatgtcg tttggtttgg ttaggacatt      480
tatatatata aagaattgat tgaaaccaac actattaaca aaatatgcag ataccaaatt      540
aacatcgtca aggttctcaa taagtaccaa gttagaaatt attatcatta tcatcattat      600
tattattatt attattatca tcatcatcat cattatttct tgctttgcca cctaagcagt      660
aaaacaatga tattagtcct ttggagaact gaggaaatta ctttaaattc ccaagttaca      720
gtaaatttgc acacagataa catgcatgtt atgtatcaag tttcacatta ttttaaaata      780
agcagtgcct ttcaaaacag atgcagacat atgtgttggt ggtagtgagg agattggtat      840
tagcatcaaa tcttcattga tgactaatgt ttaattccct tccttttatc tttaggtatg      900
gctttcccaa cgaaaggcta agaattcaag aacggtctta accgaaccct catcagatct      960
gaatttaaca aatrcttagt ctcagcagnc tccggaaaa accttagcct agcagtcagt     1020
gacttacttg cacttttgc acatagatat aaagtaaaat gatactatta atttggatta     1080
gtctgtaata ctgcaaagca acagtaattt ataaggagt gnatagaagt aaactgactg     1140
ctaagtg                                                                1147
```

```
<210> SEQ ID NO 66
<211> LENGTH: 988
<212> TYPE: DNA
<213> ORGANISM: Homo sapiens

<400> SEQUENCE: 66
```

```
ttgtatatga ccttggtgct gcatgcatgc tgttgacttt taggactttg atcttttaag       60 gttttttttcc ccagcattaa tattgattta taaagatttg aaaatctttt aatgaactgg     120
```

-continued

| | |
|---|---|
| agaacactaa gatttaaact cgaaaattcg ttgttcaagt aaagaaagcc atgatgctct | 180 |
| gtatgttatc tgtgtgtgtg catgcactca ggtgcccttt gtttcatgaa caaatacatt | 240 |
| tcattgtaca tgttttctgt ttaaatcatt gtataaagta attgcaggtc agaattatac | 300 |
| cacagaactg tttatgagag cttgtgtct gttgcacatt tcttgaagca ttttaaaat | 360 |
| aacatgtaac ctgtaacctt gttgtttaag ttttcttttc tattaatact ctgtcctgtg | 420 |
| gtcccgtgca tgctcctttt cccagaactc ctctctgctg cacccacagc atctgttccc | 480 |
| gaggagttat gactcttgac ttcctgcagg gctggggctc ttagccacca gctgctgttc | 540 |
| cagcactttc agcgcaagat ctccctgatt tgccacgtg gaattgtact tgtatatgat | 600 |
| taccttatct aaaatgaata gaggtgatg gaccagttta ctgcttagaa atagcaagag | 660 |
| gcactgcagt aaaacttgtt tctcattgta aagcttcatg tcttttgttt gttggaaaat | 720 |
| ttttacttat agaacttaa ttattagact ggtaaaataa agaccaaaat atgcagattt | 780 |
| ctaattggca ttcataaggt gaataataat aagtgcccaa tgaaaaatc tattatggtt | 840 |
| aatttcattt cttgctttgc cacctaagca gtaaaacatg atattgacca cttggagaac | 900 |
| tcagaaaatt atttttaaatt tctaagttat aataaatttg cacacagata acatgcatgc | 960 |
| tatttatgtc acatctcaca ttaaatta | 988 |

<210> SEQ ID NO 67
<211> LENGTH: 687
<212> TYPE: DNA
<213> ORGANISM: Artificial Sequence
<220> FEATURE:
<223> OTHER INFORMATION: Description of Artificial Sequence:Consensus
    sequence

<400> SEQUENCE: 67

| | |
|---|---|
| ttgttatgac cttggtgctg tgctgctgtt gacttaggac tttgatcttt taaggtttcc | 60 |
| ccactattat ttaatttgaa atctttatga actggacata agatttaaac tgaaaattct | 120 |
| tgttcataaa gaaagccgct ctgtatgtta tctgtgtgtg tgcatgcact aggtgccttt | 180 |
| gtttataaca ttttattgta catgttttct gtttaatcat tgtataaata attagtcaga | 240 |
| attatacaca gaatgtttag aggctgttct ttgcacattc ttgaagcatt ttaaataac | 300 |
| atgtaaccct aattttaag ttttctttct attaatctct gtcctgtggc ccgtgcatgc | 360 |
| tccttcccag aactcctctc tgcgcaccac agatctgttc cgaggagtta gctctcttcc | 420 |
| gcggctgctt tagcagttga attcgcagtc tctattagaa tgttagttac tttaaaaaga | 480 |
| ggtgtgaatt tctcttaaaa tacaggggta acttttatta aagttatgtt taaattcata | 540 |
| aattaaatgc ggtaataaac caatagattt tattcatcat aatatatatc ataaatcatt | 600 |
| attttttcttc ctgcaaacat aaatttgaac tggaataaat taattagtaa attcacaaaa | 660 |
| catgatgtat attcacatta ttaaata | 687 |

<210> SEQ ID NO 68
<211> LENGTH: 976
<212> TYPE: DNA
<213> ORGANISM: Mus musculus

<400> SEQUENCE: 68

| | |
|---|---|
| ttgtgtatga ccttggtgct gtgtgcctgc tgttgactcc taggactttg atcttttaaa | 60 |
| ggttccctcc cccatcctcc acttaatatt aattttgaaa gtcttagtg aacttggaca | 120 |
| ttaagattta aacttgaaaa ttcattgttc atttaaagaa agccgcagcg ctctgtatgt | 180 |

-continued

| | |
|---|---|
| tatctgtgtg tgtgcatgca cttaggtgcc tttgtttata acatttttat tgtacatgtt | 240 |
| ttctgtctta agtcattgta taaataatt ataagtcaga attatacaac agaagtgtta | 300 |
| gtaagaggct gtattctatt gcacattact tgaagcattt taaaaaaaaa ataacatgta | 360 |
| acctatatat aaccttattt aagttttcct ttctattaat tctctgtcct gtggccccg | 420 |
| tgcatgctcc ttccccagaa ctcctctctg ccgcactcac agaagctctt gttcctgagg | 480 |
| agttagggct ctcagcttcc agctgctgct cctgactgtt agtgcctagt tttgccaaat | 540 |
| agaattacta tgcagtctgc ttatctaaaa tgaaaaatag gttttcaacc agtttactgc | 600 |
| ttagagacag caagaggcac tgctgtaaaa tttctccatt ataaagtaac atgtcgtttg | 660 |
| gtttggttag gacatttata tatataaaga attgattgaa accaacacta ttaacaaaat | 720 |
| atgcagatac caaattaaca tcgtcaaggt tctcaataag taccaagtta gaaattatta | 780 |
| tcattatcat cattattatt attattatta ttatcatcat catcatcatt atttcttgct | 840 |
| ttgccaccta agcagtaaaa caatgatatt agtcctttgg agaactgagg aaattacttt | 900 |
| aaattcccaa gttacagtaa atttgcacac agataacatg catgttatgt atcaagtttc | 960 |
| acattatttt aaaata | 976 |

<210> SEQ ID NO 69
<211> LENGTH: 201
<212> TYPE: DNA
<213> ORGANISM: Homo sapiens

<400> SEQUENCE: 69

| | |
|---|---|
| aacaaactgt ttctgtgcaa cccctttgtt ttaccagaca aaatttgaat acttttttc | 60 |
| ctgaattgta tatgaccttg gtgctgcatg catgctgttg acttttagga ctttgatctt | 120 |
| ttaaggtttt tttccccagc attaatattg atttataaag atttgaaaat cttttaatga | 180 |
| actggagaac actaagattt a | 201 |

<210> SEQ ID NO 70
<211> LENGTH: 137
<212> TYPE: DNA
<213> ORGANISM: Artificial Sequence
<220> FEATURE:
<223> OTHER INFORMATION: Description of Artificial Sequence:Consensus
      sequence

<400> SEQUENCE: 70

| | |
|---|---|
| aaaaactgtt tctgtgcaac ccctgtttta ccagacaaat tgaaactttt tttgattgc | 60 |
| tgtgctgctg tgcttgactt tactttattt ccccacttaa tattatttaa agtttgaact | 120 |
| taataataaa caaatta | 137 |

<210> SEQ ID NO 71
<211> LENGTH: 199
<212> TYPE: DNA
<213> ORGANISM: Mus musculus

<400> SEQUENCE: 71

| | |
|---|---|
| aaaaaactgt ttctgtgcaa ccccactgtt ttaccagaca gaatttgaaa cttttttgtg | 60 |
| tatgaccttg gtgctgtgtg cctgctgttg actcctagga ctttgatctt ttaaggttc | 120 |
| cctcccccat cctccactta atattaattt tgaaagtctt tagtgaactt ggacattaag | 180 |
| atttaaactt gaaaattca | 199 |

What is claimed is:

1. A method of identifying a psychotropic agent that does not induce a significant motor side effect, the method comprising:
   (a) providing a test cell population comprising a cell capable of expressing a gene, wherein the gene is HALO6 (SEQ ID NO:10);
   (b) contacting said test cell population with said psychotropic agent; and
   (c) comparing the expression of said gene in said test cell population to the expression of said gene in a reference cell population that has been exposed to a control agent;
   wherein an increase in expression of said gene in the test cell population compared to the expression of said gene in the reference cell population indicates the psychotropic agent does not induce a significant motor side effect.

2. The method of claim 1, wherein said reference cell population is treated with a psychotropic agent which induces a motor side effect.

3. The method of claim 1, wherein said cell population is provided in vitro.

4. The method of claim 1, wherein said cell population is provided ex vivo from a mammalian subject.

5. The method of claim 1, wherein said cell population is derived from a human or rodent subject.

6. The method of claim 1, wherein said cell is provided in vivo in a mammalian subject.

7. The method of claim 1, wherein said cell is a neuronal cell.

8. The method of claim 1, wherein said cell is from brain tissue.

9. The method of claim 8, wherein said cell is from striatum brain tissue.

10. The method of claim 1, wherein said cell is a human cell.

11. The method of claim 1, wherein said control agent is a butyrophenone compound.

12. The method of claim 1, wherein said control agent is selected from the group consisting of droperidol and haloperidol.

13. The method of claim 1, wherein said control agent is haloperidol.

14. The method of claim 1, wherein said control agent is a phenothiazine.

15. The method of claim 1, wherein said control agent is chorpromaine.

16. The method of claim 1, wherein said motor side effect is an extrapyramidal motor pathology.

17. The method of claim 16, wherein said motor side effect is a dystonia.

18. A method of selecting a psychotropic agent appropriate for a particular subject, the method comprising:
   (a) providing from said subject a test cell population comprising a cell capable of expressing a gene, wherein the gene is HALO6 (SEQ ID NO:10);
   (b) contacting said test cell population with said psychotropic agent; and
   (c) comparing the expression of said gene from the test cell population of said subject to the expression of said gene in a reference cell population that has been exposed to a control agent causing motor side effects;
   wherein an increase in expression of said gene in the cell population compared to the expression of said gene in the reference cell population indicates the psychotropic gent is appropriate for said subject.

19. The method of claim 18, wherein said subject is a human.

20. The method of claim 18, wherein said appropriate psychotropic agent does not induce a significant motor defect in said subject.

* * * * *